(12) United States Patent  (10) Patent No.: US 7,511,133 B2
Baraldi et al.  (45) Date of Patent: Mar. 31, 2009

(54) ADENOSINE $A_3$ RECEPTOR AGONISTS

(75) Inventors: Pier Giovanni Baraldi, Ferrara (IT); Allan R. Moorman, Durham, NC (US); Pier A. Borea, Ferrara (IT)

(73) Assignee: King Pharmaceuticals Research and Development, Inc., Cary, NC (US)

( * ) Notice: Subject to any disclaimer, the term of this patent is extended or adjusted under 35 U.S.C. 154(b) by 397 days.

(21) Appl. No.: 10/944,245

(22) Filed: Sep. 17, 2004

(65) Prior Publication Data

US 2005/0250729 A1    Nov. 10, 2005

Related U.S. Application Data

(60) Provisional application No. 60/504,579, filed on Sep. 18, 2003.

(51) Int. Cl.
| | |
|---|---|
| C07H 19/00 | (2006.01) |
| C07H 19/16 | (2006.01) |
| C07H 19/22 | (2006.01) |
| C07H 19/167 | (2006.01) |
| C07H 19/173 | (2006.01) |

(52) U.S. Cl. .............. 536/27.62; 536/27.1; 536/27.13; 536/27.2; 536/27.22; 536/27.6

(58) Field of Classification Search .............. None
See application file for complete search history.

(56) References Cited

U.S. PATENT DOCUMENTS 6,048,865 A * 4/2000 Baraldi ................ 514/46

OTHER PUBLICATIONS

Baraldi et al., "Novel $N^6$-(Substituted-phenylcarbamoyl)adenosine-5'-uronamides as Potent Agonists for $A_3$ Adenosine Receptors", *Journal of Medicinal Chemistry* 1996, 39(3), 802-806.
Baraldi et al., "Synthesis and Biological Activity of a New Series of $N^6$-Arylcarbamoyl, 2-(Ar)alkynyl-$N^6$-arylcarbamoyl, and $N^6$-Carboxamido Derivatives of Adenosine-5'-N-ethyluronamide as $A_1$ and $A_3$ Adenosine Receptor Agonists", *Journal of Medicinal Chemistry* 1998, 41(17), 3174-3185.

* cited by examiner

*Primary Examiner*—Traviss C McIntosh, III
(74) *Attorney, Agent, or Firm*—Paivi Kukkola

(57) ABSTRACT

The compounds of the following formula:

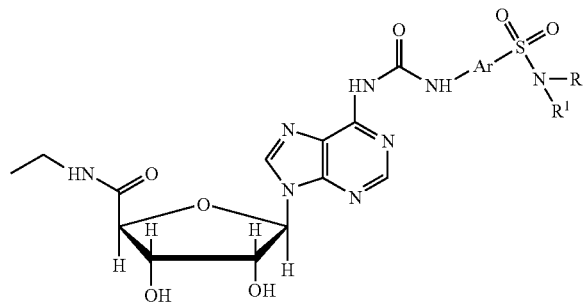

wherein Ar, R and $R^1$ have the meanings given in the specification. This series of sulfonamido derivatives with a conserved uronamide group at the 5' position provide superior A3 receptor affinity as well as selectivity. These new adenosine agonists are sulfonamido derivatives N-substituted with aliphatic groups (cyclic or linear) or aromatic radicals.

1 Claim, 5 Drawing Sheets

ADENOSINE A₃ RECEPTOR AGONISTS

RELATED APPLICATIONS

This application claims priority to U.S. Provisional Application 60/504,579 filed Sep. 18, 2003, which application is hereby incorporated by reference in its entirety.

BACKGROUND OF THE INVENTION

1. Field of the Invention

This invention pertains to new adenosine receptor agonists and methods of their use. More particularly, this invention provides a genus of sulfonamido derivatives with a conserved ethyl uronamide group.

2. Background

Adenosine exerts a number of physiological functions through activation of four cell membrane receptors classified as $A_1$, $A_{2A}$, $A_{2B}$ and $A_3$. The most recently discovered $A_3$ subtype has been the subject of intensive pharmacological characterization. Although all adenosine subclasses belong to the G protein-coupled receptors they are associated with different second messenger systems. The $A_3$ subtype is believed to have a characteristic second messenger profile, in that it has been shown to mediate adenylyl cyclase inhibition and phospholipase C activation.

It is also believed that the adenosine $A_3$ receptor may play a basic role in modulation of cerebral ischemia, inflammation, hypotension, ischemic heart pre-conditioning and asthma. This has made the $A_3$ receptor a therapeutic target on cell growth, on apoptosis, malignant cell growth, on leukemic Jurkat T cells, on human malignant melanoma A375 cell line and on human neutrophils. The human cloned $A_3$ adenosine receptor was first characterized with $N^6$-(4-amino-3-[$^{125}$I]iodobenzyl)adenosine.

It is believed that the presence of an $N^6$ benzyl moiety in the adenosine structure provides a significant increase in $A_3$ receptor affinity and selectivity. It is also believed that a methyl or ethyl uronamide moiety confers better affinity and selectivity at the $A_3$ adenosine receptor. This combination of substitutions is present in $N^6$-(3-iodo-benzyl)-adenosine-5'-N-methyl-uronamide (IB-MECA). IB-MECA is 50 fold selective for the $A_3$ receptor versus either the $A_1$ or $A_{2A}$ receptors. A selective radioligand, the [$^{125}$I]-$N^6$-(4 amino-3-iodobenzyl)-adenosine-5'-N-methyl-uronamide ([$^{125}$I]-AB-MECA) has also been developed. This compound has a high affinity, although less selectivity, but is still considered to be a standard agonist for the $A_3$ adenosine receptor.

It is also thought that substitutions at the 2-position on the benzyl group with halogen, methylamino or thiomethyl groups increase both affinity and selectivity at the $A_3$ receptor subtype. Substituents at the 3-position on the benzyl group also appear to be well tolerated. Both affinity and selectivity for the $A_3$ receptor subtype seems to be related more to the type of substitution on the phenyl ring than to the position of the substituent.

Purine and ribose-modified adenosine analogs have been studied for their affinity at rat $A_3$ adenosine receptors, but these compounds have typically not shown a better profile with respect to reference compounds. Several modifications utilized have suggested that: i) deaza derivatives are well tolerated at the $A_3$ receptor; ii) substitutions at the 8 position are detrimental in terms of affinity; iii) carbocyclic nucleosides exhibit, in general, weak affinity at all receptor subtypes; iv) replacement of 6-NHCH$_2$ linkage with hydroxylamino or hydrazino moieties is well tolerated; v) substitution of 4' hydrogen with a methyl group retains agonist activity and selectivity at rat $A_3$ adenosine receptors.

BRIEF SUMMARY OF THE INVENTION

This invention realizes that a series of sulfonamido derivatives with a conserved uronamide group at the 5' position provide superior $A_3$ receptor affinity as well as selectivity. These new adenosine agonists are sulfonamido derivatives N-substituted with aliphatic groups (cyclic or linear) or aromatic radicals.

The compounds of this invention can be described by the general formula:

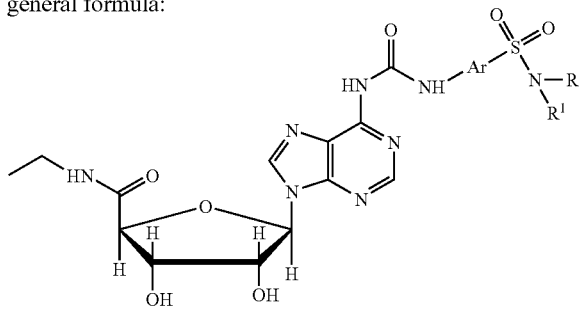

wherein Ar is an aryl group, and R and $R^1$ are independently H, alkyl, aryl, substituted alkyl, substituted aryl, heteroaryl, alkenyl, substituted alkenyl, cycloalkenyl, substituted cycloalkenyl, cycloalkyl, substituted cycloalkyl, alkynyl, or substituted alkynyl, or R and $R^1$ together with the nitrogen atom to which they are attached form a substituted or unsubstituted saturated or unsaturated 3 to 20-membered ring system having a single ring or multiple condensed rings which may optionally contain 1 to 4 additional heteroatoms selected from O, S and N.

This invention also provides methods for the treatment of diseases in which mediation of the $A_3$ receptor plays a role. The invention also encompasses pharmaceutical salts and pharmaceutical compositions of the disclosed compounds as well.

DETAILED DESCRIPTION OF THE INVENTION

Figure 1:
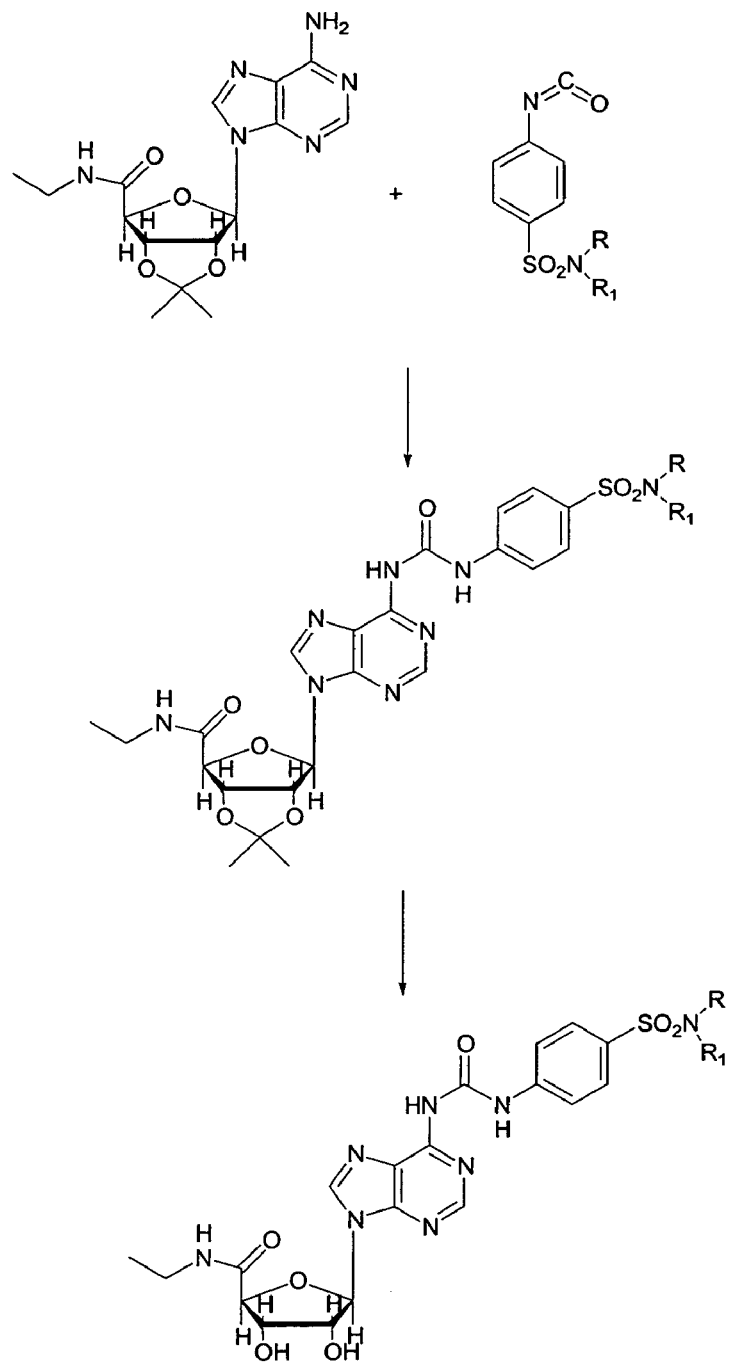
FIG. 1 shows a general synthetic strategy used for the preparation of compounds 83 through 102.

Chemical and pharmaceutical compositions. The compounds of this invention can be described by the general formula:

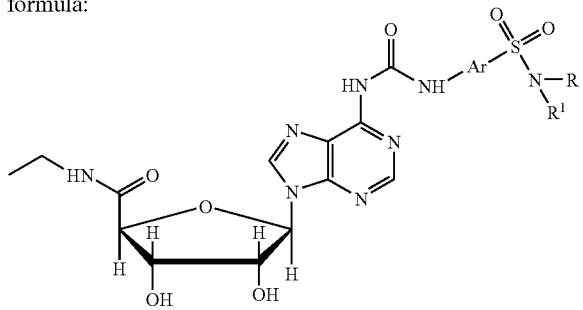

wherein Ar is an aryl group, which may be ortho, meta or para substituted, and R and $R^1$ are independently H, alkyl, aryl, substituted alkyl, substituted aryl, heteroaryl, alkenyl, substituted alkenyl, cycloalkenyl, substituted cycloalkenyl, cycloalkyl, substituted cycloalkyl, alkynyl, or substituted alkynyl, or R and $R^1$ together with the nitrogen atom to which they are attached form a substituted or unsubstituted saturated or unsaturated 3 to 20-membered ring system having a single ring or multiple condensed rings which may optionally contain 1 to 4 additional heteroatoms selected from O, S and N.

As used herein, the term "alkyl" refers to monovalent straight, branched or cyclic paraffinic hydrocarbon groups that may be derived from an alkane by dropping one hydrogen from the formula.

Alkyl groups typically have from about 1 to 20 carbon atoms, and preferably from about 1 to 10 carbon atoms ("lower alkyl") and most preferably about 1 to 6 carbon atoms. This term is exemplified by groups such as methyl, ethyl, n-propyl, iso-propyl, n-butyl, iso-butyl, n-hexyl, and the like.

The terms "alkylene" and "lower alkylene" refer to divalent radicals of the corresponding alkane. Further, as used herein, other moieties having names derived from alkanes, such as alkoxy, alkanoyl, alkenyl, cycloalkenyl, etc., when modified by "lower," have carbon chains of about ten or fewer carbon atoms. In those cases where the minimum number of carbons required are greater than one, e.g., alkenyl and alkynyl (minimum of two carbons) and cycloalkyl (minimum of three carbon atoms), it is to be understood that the term "lower" means at least the minimum number of carbon atoms.

As used herein, the term "substituted alkyl" refers to an alkyl group, typically having from about 1 to 5 substituents, and preferably about 1 to 3 substituents. Preferred substituents include alkoxy, substituted alkoxy, cycloalkoxy, substituted cycloalkoxy, cycloalkyl, substituted cycloalkyl, cycloalkenyl, substituted cycloalkenyl, alkynyl, acyl, acylamino, acyloxy, amino, aralkyl, substituted aralkyl, aryl, substituted aryl, carboxyl, carboxyalkyl, cyano, halogen, hydroxyl, aryloxy, substituted aryloxy, heteroaryl, heteroaryloxy, heterocyclyl, hydroxylamino, alkoxyamino, nitro, alkylthio, substituted alkylthio, arylthio, substituted arylthio, and mono- and di-alkylamino, mono- and di-(substituted alkyl) amino, mono- and di-arylamino, mono- and di-heteroarylamino, and unsymmetric di-substituted amines having different substituents selected from alkyl, aryl, aralkyl, and heteroaryl. As used herein, other moieties having the prefix "substituted" are intended to include one or more of the substituents listed above.

As used herein, the term "alkoxy" refers to the group "alkyl-O—", where alkyl is as defined above. Preferred alkoxy groups include methoxy, ethoxy, n-propoxy, iso-propoxy, n-butoxy, tert-butoxy, sec-butoxy, n-pentoxy, n-hexoxy, 1,2-dimethylbutoxy, and the like.

As used herein, the term "alkenyl" refers to unsaturated aliphatic hydrocarbon groups having one or more double bonds, typically having from about 2 to 10 carbon atoms, and preferably from about 2 to 6 carbon atoms. This term is exemplified by such groups as ethenyl, n-propenyl, iso-propenyl, and the like.

As used herein, the term "alkynyl" refers to alkynyl groups typically having from about 2 to 10 carbon atoms, and preferably about 2 to 6 carbon atoms and having one or more sites of alkynyl unsaturation.

As used herein, the term "aryl" refers to an unsaturated aromatic carbocyclic group typically from 6 to 14 carbon atoms having a single ring (e.g., phenyl) or multiple condensed (fused) rings (e.g., naphthyl or anthryl). Preferred aryls include phenyl, naphthyl and the like. Phenyl is highly preferred.

Unless otherwise constrained by the definition for the aryl substituent, such aryl groups can optionally be substituted with from about 1 to 5 substituents and preferably about 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, acyloxy, acylamino, alkaryl, aryl, aryloxy, azido, carboxyl, carboxylalkyl, cyano, halo, nitro, heteroaryl, heteroaryloxy, trihalomethyl. Preferred substituents include alkyl, alkoxy, halo, cyano, and trihalomethyl.

As used herein, the term "aralkyl" refers to an aryl or substituted aryl group attached to an alkylene group of substituted alkylene group, where aryl, substituted aryl, alkylene, and substituted alkylene are as defined herein.

As used herein, the term "cycloalkyl" refers to cyclic alkyl groups typically of from about 3 to 12 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

As used herein, the terms "halo" or "halogen" refer to fluoro, chloro, bromo and iodo.

As used herein, the term "heterocyclic" refers to a monovalent saturated or unsaturated carbocyclic group having a single ring or multiple condensed rings.

Typically, a heterocyclic has from about 1 to 15 carbon atoms, with from about 1 to 5 heteroatoms within the ring or rings, preferably from about 1 to 9 carbon atoms and from about 1 to 4 heteroatoms within the ring or rings, selected from the group of heteroatoms consisting of nitrogen, sulfur, and oxygen. This term is exemplified by groups such as tetrahydrofur-anyl, pyrrolinyl, pyrrolidinyl, oxazolidinyl, thiazolidinyl, imidazolinyl, imida-zolidinyl, piperidinyl, piperazinyl, quinuclidinyl, thiomorpholinyl, morpholinyl, dioxolanyl, and the like.

As used herein, the term "heteroaryl" refers to an aromatic carbocyclic group typically of from about 1 to 15 carbon atoms and about 1 to 4 heteroatoms selected from the group consisting of oxygen, nitrogen and sulfur within at least one ring (if there is more than one ring).

Unless otherwise constrained by the definition for the heteroaryl substituent, such heteroaryl groups can be optionally substituted with from about 1 to 5 substituents and preferably about 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, acyloxy, acylamino, aryl, aryloxy, azido, carboxyl, carboxylalkyl, cyano, halo, nitro, heteroaryl, heteroaryloxy, and trihalomethyl. Preferred substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl).

"Pharmaceutically acceptable salts" refers to pharmaceutically acceptable salts of a compound, which salts can be derived from a variety of organic and inorganic counter ions well known in the art and include, by way of example, sodium, potassium, calcium, magnesium, ammonium, tetraalkylammonium, and the like. When the molecule contains a basic functionality, salts of organic or inorganic acids, such as hydrochloride, hydrobromide, tartrate, mesylate, acetate, maleate, oxalate, and the like, can be used as the pharmaceutically acceptable salt.

This invention also encompasses compounds which are labeled with radioactive isotopes, such as, but not limited to tritium ($^3H$), carbon ($^{14}C$), iodine ($^{125}I$), phosphorus ($^{31}P$, $^{32}P$, $^{33}P$), and sulfur ($^{35}S$). The compounds may also be labeled in other ways, e.g. fluorescently or with PET (Positron Emission Tomography) or SPECT (Single Photon Emission Tomography) labels. For example, the 2 or 8 position on the purine moiety may be labeled with tritium.

Also known is the use of stable isotopes, such as deuterium ($^2$H) and $^{13}$C that are detected by magnetic resonance imaging or mass spectrometry. The compounds of this invention may also be labeled or derivatized, for example, for kinetic binding experiments, for further elucidating metabolic pathways and enzymatic mechanisms, or for characterization by methods known in the art of analytical chemistry.

As used herein, the term "labeled" includes the use of any of the forms herein described.

As used herein, the term "therapeutically effective amount" is a dosage at which beneficial effects are obtained in the patient.

This invention also encompasses the use of the disclosed compounds in screening assays to determine the effectiveness of other compounds for binding to the A3 adenosine receptor through competitive inhibition as determined by various binding assays. Such a screening assay would make use of a labeled form of one of the compounds, preferably tritiated. Such screening assays are described in Jacobson and Van Rhee, Purinergic approaches to experimental therapy, Jacobson and Jarvis, ed., Wiley, New York, 1997, pp. 101-128; Mathot et al., Brit. J. Pharmacol., 116:1957-1964 (1995); van der Wenden et al., J. Med. Chem., 38:4000-4006 (1995); and van Calenbergh, J. Med. Chem., 40:3765-3772 (1997), the contents of which are hereby incorporated by reference.

Preferred compounds of this invention are listed in Table 1.

TABLE 1

| Compound # | Structure | Name |
|---|---|---|
| 83 | 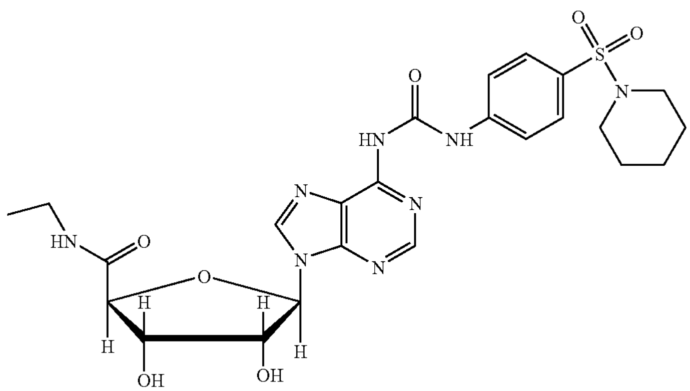 | 1-Deoxy-1-[6-[[[[4-[(piperidin-1-yl)sulfonyl]phenyl]amino]carbonyl]amino]-9H-purin-9-yl]-N-ethyl-β-D-ribofuranuronamide |
| 84 | 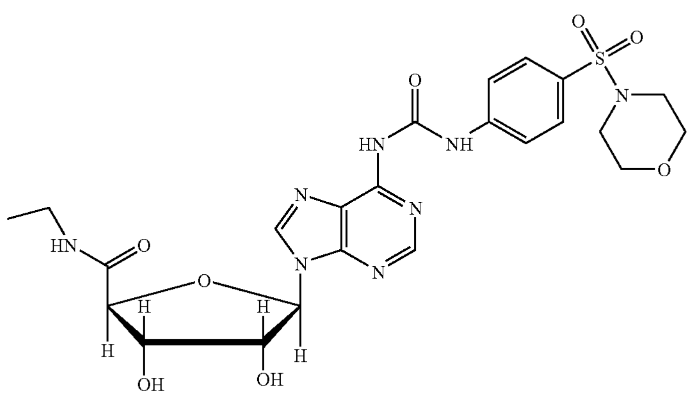 | 1-Deoxy-1-[6-[[[[4-[(morpholine-1-yl)sulfonyl]phenyl]amino]carbonyl]amino]-9H-purin-9-yl]-N-ethyl-β-D-ribofuranuronamide |
| 85 | 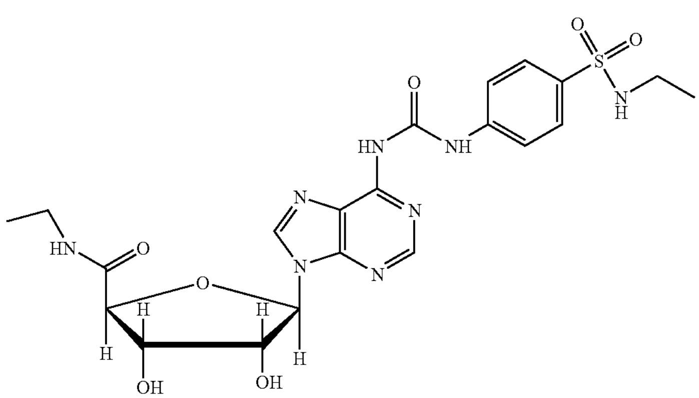 | 1-Deoxy-1-[6-[[[[4-[N-(ethyl)aminosulfonyl]phenyl]amino]-carbonyl]amino]-9H-purin-9-yl]-N-ethyl-β-D-ribofuranuronamide |

TABLE 1-continued

| Compound # | Structure | Name |
|---|---|---|
| 86 | 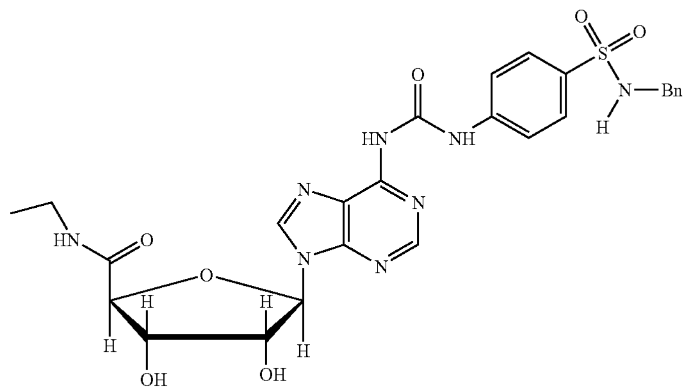 | 1-Deoxy-1-[6-[[[[4-[N-(benzyl)aminosulfonyl]phenyl]amino]-carbonyl]amino]-9H-purin-9-yl]-N-ethyl-β-D-ribofuranuronamide |
| 87 | 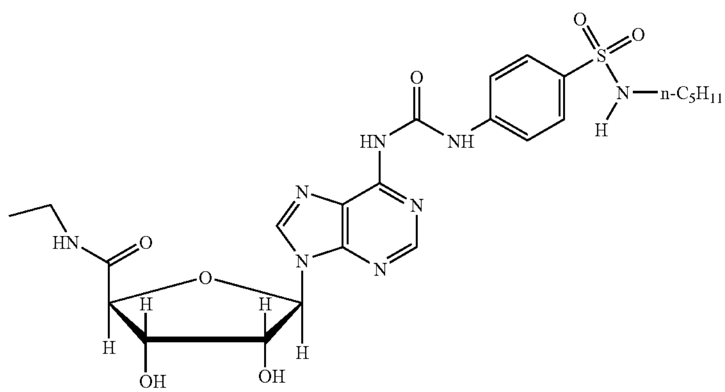 | 1-Deoxy-1-[6-[[[[4-[N-(pentyl)aminosulfonyl]phenyl]-amino]carbonyl]amino]-9H-purin-9-yl]-N-ethyl-β-D-ribofuranuronamide |
| 88 | 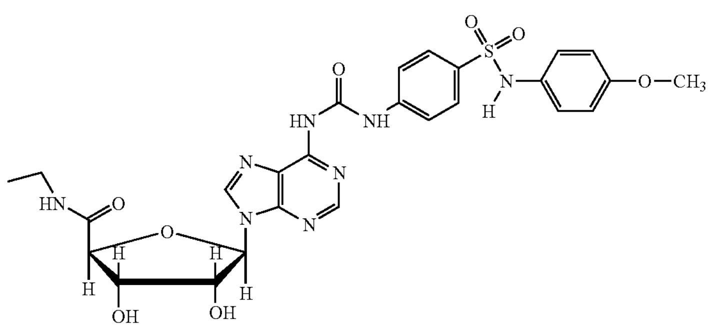 | 1-Deoxy-1-[6-[[[[4-[N-(4-methoxyphenyl)aminosulfonyl]phenyl]-amino]carbo-nyl]amino]-9H-purin-9-yl]-N-ethyl-β-D-ribofuranuronamide |
| 89 | 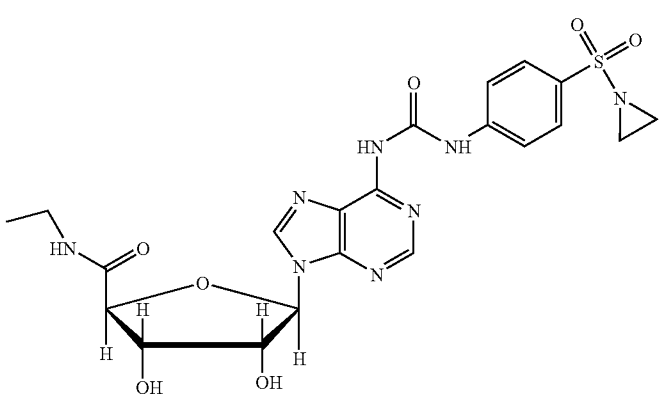 | 1-Deoxy-1-[6-[[[[4-[N-(cyclopropyl)aminosulfonyl]phenyl]amino]-carbonyl]-amino]-9H-purin-9-yl]-N-ethyl-β-D-ribofuranuronamide |

TABLE 1-continued

| Compound # | Structure | Name |
|---|---|---|
| 90 | 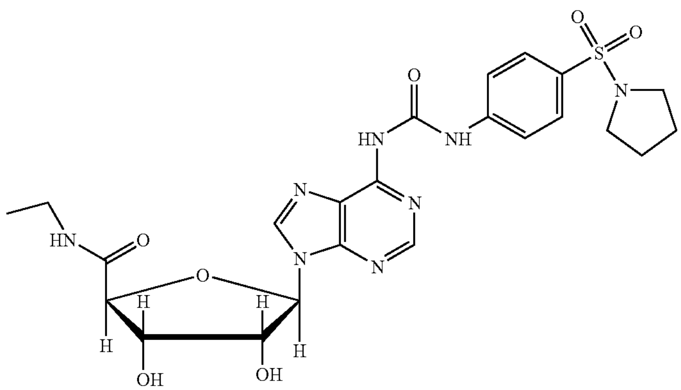 | 1-Deoxy-1-[6-[[[[4-[(pyrrolidin-1-yl)sulfonyl]phenyl]amino]carbonyl]amino]-9H-purin-9-yl]-N-ethyl-β-D-ribofuranuronamide |
| 91 | 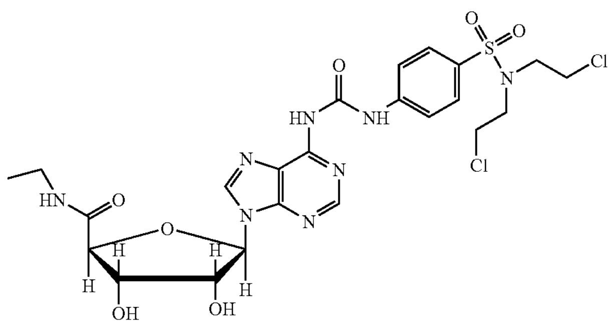 | 1-Deoxy-1-[6-[[[[4-[N,N-bis(2-chloroethyl)aminosulfonyl]phenyl]-amino]carbonyl]amino]-9H-purin-9-yl]-N-ethyl-β-D-ribofuranuronamide |
| 92 | 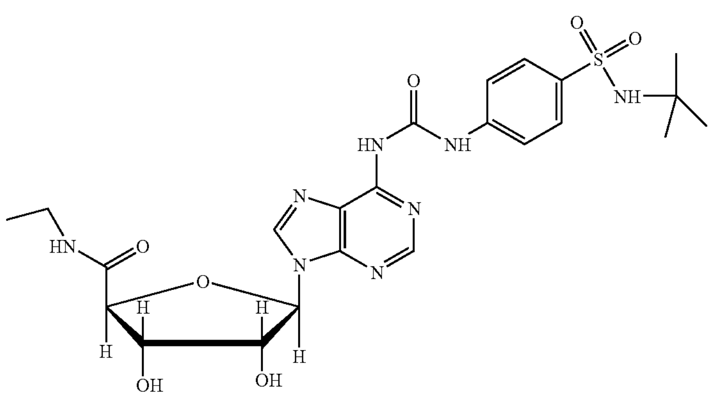 | 1-Deoxy-1-[6-[[[[4-[N-(1,1-dimethylethyl)aminosulfonyl]phenyl]amino]-carbonyl]amino]-9H-purin-9-yl]-N-ethyl-β-D-ribofuranuronamide |
| 93 | 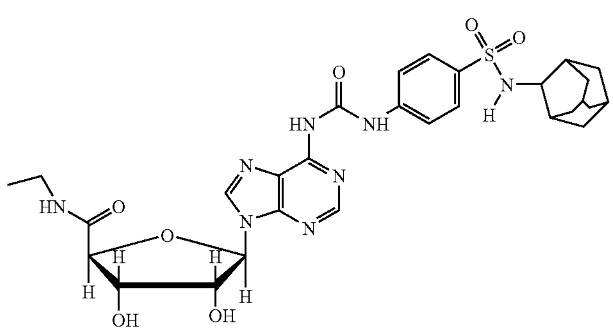 | 1-Deoxy-1-[6-[[[[4-[N-(adamantan-1-yl)sulfonyl]phenyl]amino]carbonyl]-amino]-9H-purin-9-yl]-N-ethyl-β-D-ribofuranuronamide |

TABLE 1-continued

| Compound # | Structure | Name |
|---|---|---|
| 94 | 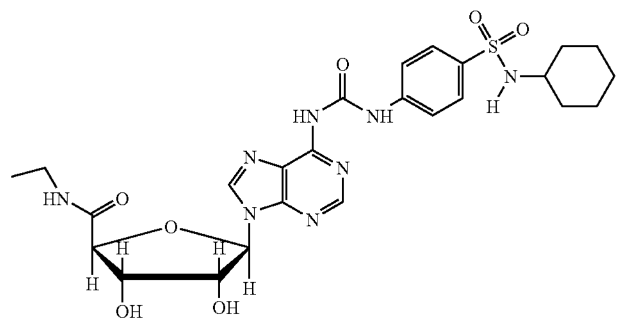 | 1-Deoxy-1-[6-[[[[4-[N-(cyclohexyl)aminosulfonyl]phenyl]-amino]carbonyl]amino]-9H-purin-9-yl]-N-ethyl-β-D-ribofuranuronamide |
| 95 | 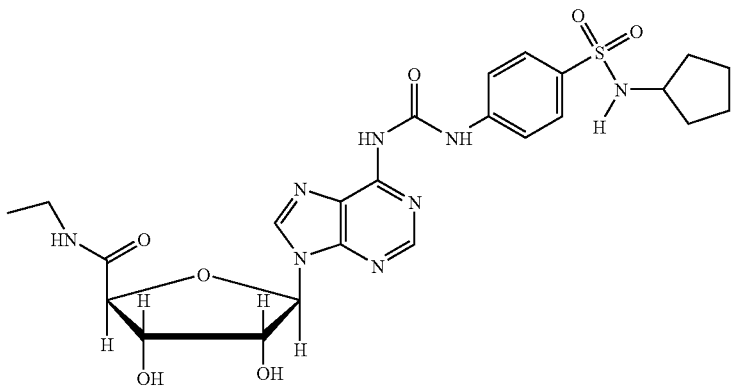 | 1-Deoxy-1-[6-[[[[4-[N-(cyclopentyl)aminosulfonyl]phenyl]-amino]carbonyl]amino]-9H-purin-9-yl]-N-ethyl-β-D-ribofuranuronamide |
| 96 | 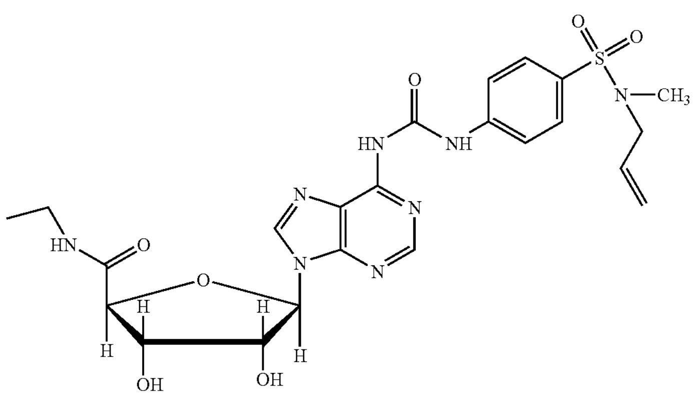 | 1-Deoxy-1-[6-[[[[4-[N-(allyl)-N-(methyl)amino-sulfonyl]phenyl]amino]carbonyl]amino]-9H-purin-9-yl]-N-ethyl-β-D-ribofuranuronamide |
| 97 | 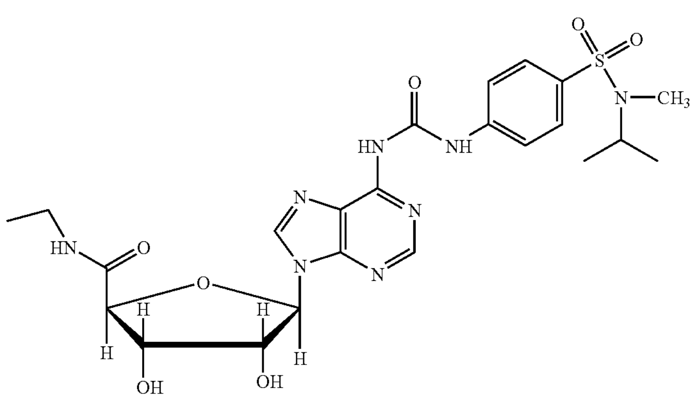 | 1-Deoxy-1-[6-[[[[4-[N-(1-methylethyl)-N-(methyl)-aminosulfonyl]phenyl]amino]carbonyl]amino]-9H-purin-9-yl]-N-ethyl-β-D-ribofuranuronamide |

TABLE 1-continued

| Compound # | Structure | Name |
|---|---|---|
| 98 | 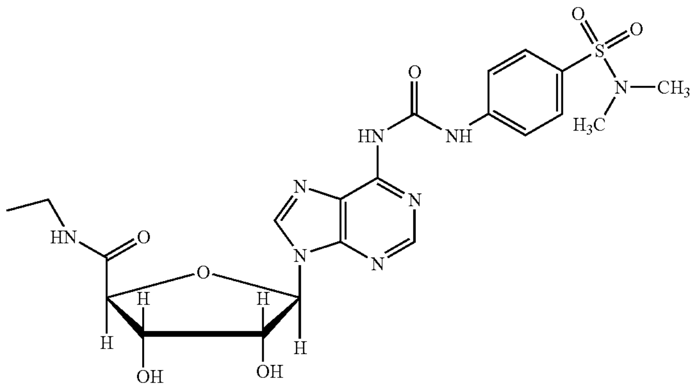 | 1-Deoxy-1-[6-[[[[4-[N,N-(dimethyl)amino-sulfonyl]phenyl]amino]carbonyl]amino]-9H-purin-9-yl]-N-ethyl-β-D-ribofuranuronamide |
| 99 | 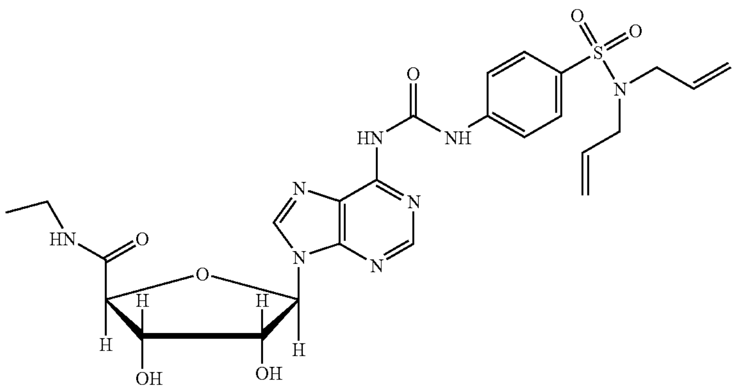 | 1-Deoxy-1-[6-[[[[4-[N,N-bis(allyl)amino-sulfonyl]phenyl]amino]carbonyl]amino]-9H-purin-9-yl]-N-ethyl-β-D-ribofuranuronamide |
| 100 | 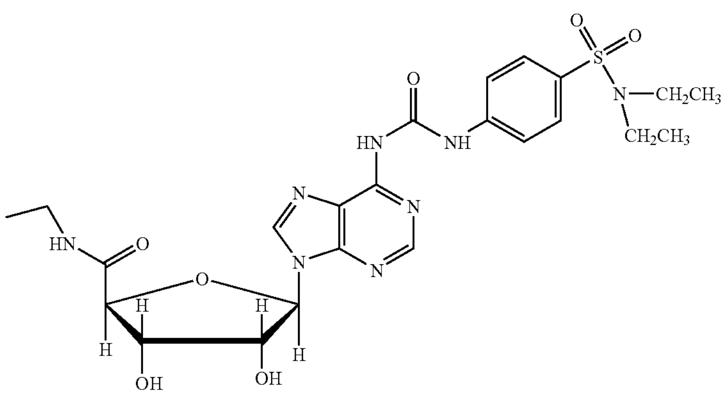 | 1-Deoxy-1-[6-[[[[4-[N,N-bis(ethyl)amino-sulfonyl]phenyl]amino]carbonyl]amino]-9H-purin-9-yl]-N-ethyl-β-D-ribofuranuronamide |
| 101 | 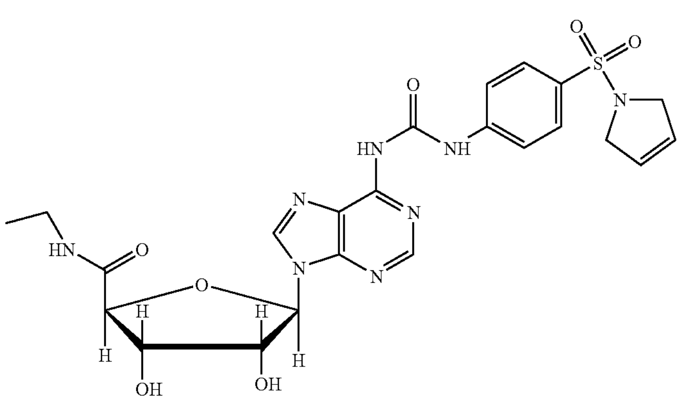 | 1-Deoxy-1-[6-[[[[4-[N-(allyl)-N-(methyl)aminosulfonyl]phenyl]amino]carbonyl]amino]-9H-purin-9-yl]-N-ethyl-β-D-ribofuranuronamide |

TABLE 1-continued

| Compound # | Structure | Name |
|---|---|---|
| 102 | 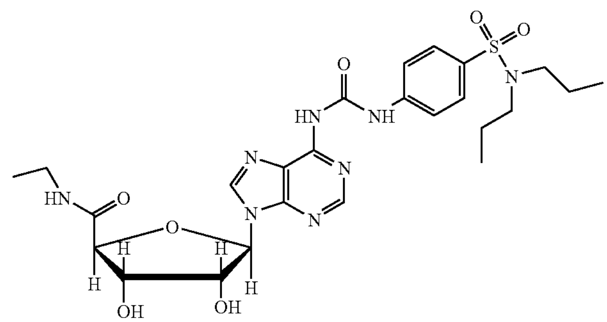 | 1-Deoxy-1-[6-[[[[4-[N,N-bis(propyl)aminosulfonyl]phenyl]amino]-carbo-nyl]amino]-9H-purin-9-yl]-N-ethyl-β-D-ribofuranuronamide |
| 103 | 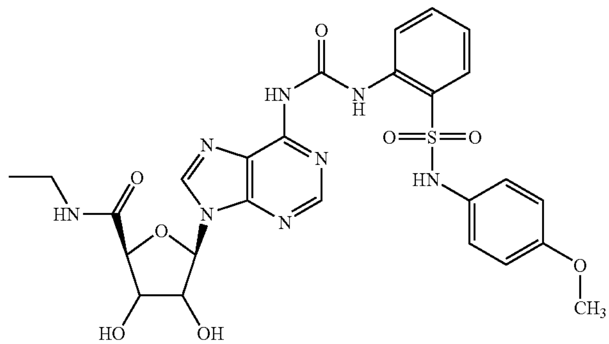 | 1-Deoxy-N-ethyl-1-[[6-[[[2-N-(4-methoxyphenyl)-sulfonamidophenyl]amino]carbonyl]amino]-9H-purin-9-yl]-b-D-ribofuran-uronamide |
| 104 | 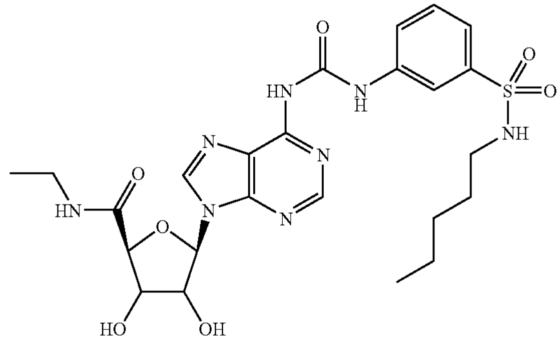 | 1-Deoxy-N-ethyl-1-[[6-[[[3-N-(pentyl)-sulfonamido-phenyl]amino]carbonyl]amino]-9H-purin-9-yl]-b-D-ribofuranuronamide |
| 105 | 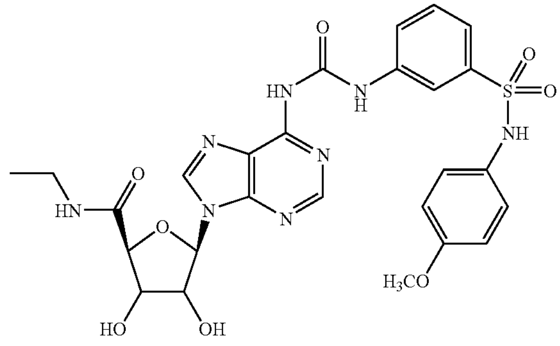 | 1-Deoxy-N-ethyl-1-[[6-[[[3-N-(4-methoxyphenyl)-sulfonamidophenyl]amino]carbonyl]amino]-9H-purin-9-yl]-b-D-ribofuran-uronamide |

TABLE 1-continued

| Compound # | Structure | Name |
|---|---|---|
| 106 | 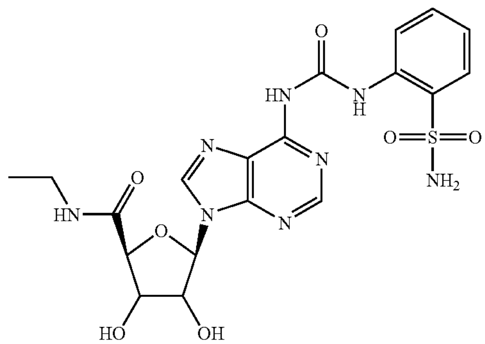 | 1-Deoxy-N-ethyl-1-[[6-[[(2-sulfonamidophenyl)amino]-carbonyl]amino]-9H-purin-9-yl]-b-D-ribofuranuronamide |
| 107 | 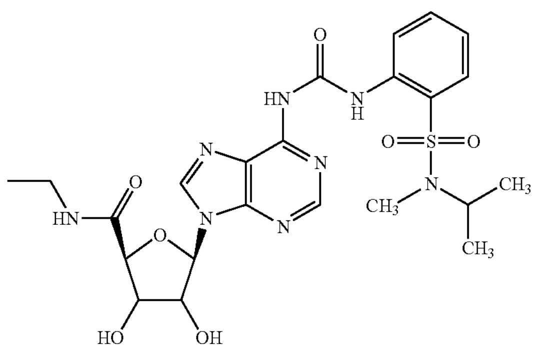 | 1-Deoxy-N-ethyl-1-[[6-[[[2-N-(isopropyl)-N-(methyl)-sulfonamidophenyl]amino]carbonyl]amino]-9H-purin-9-yl]-b-D-ribofuranuron-amide |
| 108 | 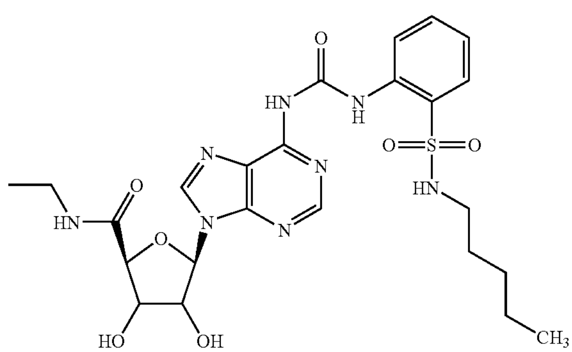 | 1-Deoxy-N-ethyl-1-[[6-[[[2-N-(pentyl)-sulfonamido-phenyl]amino]carbonyl]amino]-9H-purin-9-yl]-b-D-ribofuranuronamide |
| 109 | 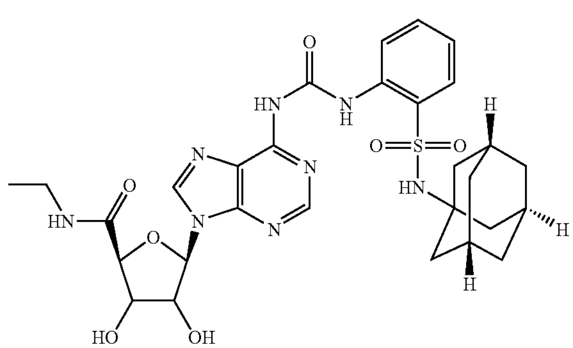 | 1-Deoxy-N-ethyl-1-[[6-[[[2-N-(adamantan-1-yl)-sulfonamidophenyl]amino]carbonyl]amino]-9H-purin-9-yl]-b-D-ribofuran-uronamide |

TABLE 1-continued

| Compound # | Structure | Name |
|---|---|---|
| 110 | 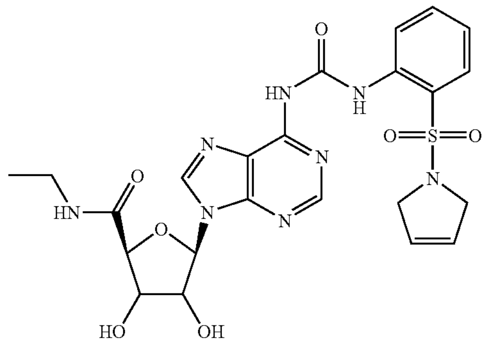 | 1-Deoxy-N-ethyl-1-[[6-[[[2-(2,5-dihydropyrrol-1-yl)sulfonylphenyl]amino]carbonyl]amino]-9H-purin-9-yl]-b-D-ribofuranuronamide |
| 111 | 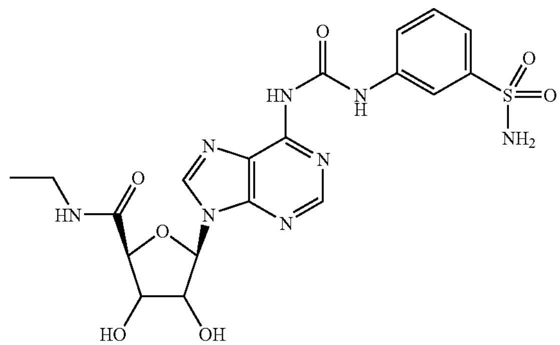 | 1-Deoxy-N-ethyl-1-[[6-[[(3-sulfonamidophenyl)-amino]carbonyl]amino]-9H-purin-9-yl]-b-D-ribofuranuronamide |
| 112 | 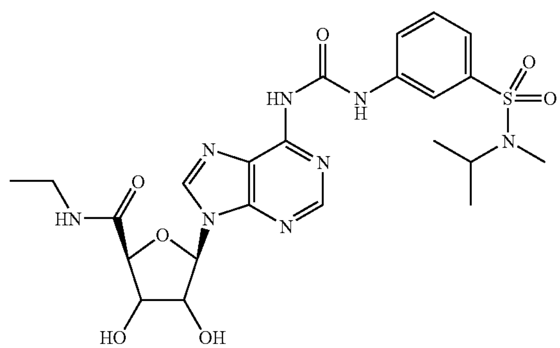 | 1-Deoxy-N-ethyl-1-[[6-[[[3-N-(isopropyl)-N-(methyl)-sulfonamidophenyl]amino]carbonyl]amino]-9H-purin-9-yl]-b-D-ribofuranuron-amide |
| 113 | 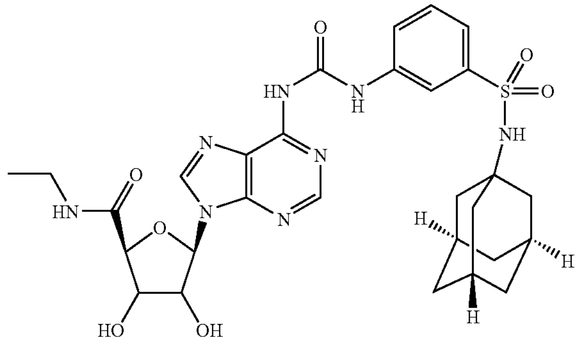 | 1-Deoxy-N-ethyl-1-[[6-[[[3-N-(adamantan-1-yl)-sulfonamidophenyl]amino]carbonyl]amino]-9H-purin-9-yl]-b-D-ribofuran-uronamide |

TABLE 1-continued

| Compound # | Structure | Name |
|---|---|---|
| 114 | 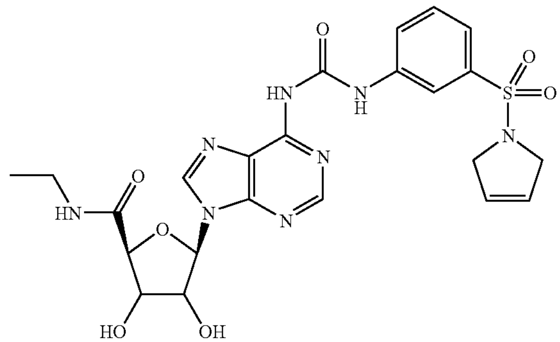 | 1-Deoxy-N-ethyl-1-[[6-[[[3-(2,5-dihydropyrrol-1-yl)sulfonylphenyl]amino]carbonyl]amino]-9H-purin-9-yl]-b-D-ribofuranuronamide |

Affinity and selectivity at the $A_3$ receptor. The compounds of this invention show good affinity at the $A_3$ receptor, and good selectivity versus the $A_1$ receptor. Results of radioligand binding assays displacing agonists with preferred compounds 83-102 at human $A_1$, $A_{2A}$, and $A_3$ adenosine receptors expressed in CHO cells are shown in Table 2.

TABLE 2

| | | | Ki (nM) | | | |
|---|---|---|---|---|---|---|
| compd | R | R1 | Ki($A_1$). Displacement of [$^3$H]CHA binding to human $A_1$ adenosine receptors exp. in CHO cells. | Ki($A_{2A}$). Displacement of [$^3$H]CGS21680 binding to human $A_{2A}$ adenosine receptors exp. in CHO cells. | Ki($A_3$). Displacement of [$^{125}$I]AB-MECA binding to human $A_3$ adenosine receptors exp. in CHO cells. | $A_1/A_3$ |
| 83 | R = R1 (cyclohexyl) | R = R1 (cyclohexyl) | 750 (664-849) | >1000 | 17 (13-22) | 44 |
| 84 | R = R1 (tetrahydropyranyl) | R = R1 (tetrahydropyranyl) | 725 (620-849) | >1000 | 20 (12-34) | 36.25 |
| 85 | Et | H | 250 (179-348) | >1000 | 23 (17-32) | 10.86 |

TABLE 2-continued

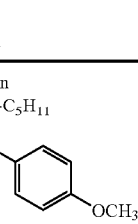

| compd | R | R1 | Ki(A$_1$). Displacement of [$^3$H]CHA binding to human A$_1$ adenosine receptors exp. in CHO cells. | Ki(A$_{2A}$). Displacement of [$^3$H]CGS21680 binding to human A$_{2A}$ adenosine receptors exp. in CHO cells. | Ki(A$_3$). Displacement of [$^{125}$I]AB-MECA binding to human A$_3$ adenosine receptors exp. in CHO cells. | A$_1$/A$_3$ |
|---|---|---|---|---|---|---|
| 86 | Bn | H | 300 (226-398) | >1000 | 24 (18-33) | 12.5 |
| 87 | n-C$_5$H$_{11}$ | H | 445 (369-537) | >1000 | 80 (66-97) | 5.56 |
| 88 | 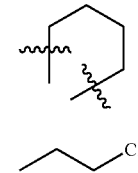 | H | 280 (192-409) | >1000 | 23 (15-34) | 12.17 |
| 89 | c-C$_3$H$_7$ | H | 290 (272-309) | >1000 | 25 (17-36) | 11.6 |
| 90 | R = R1 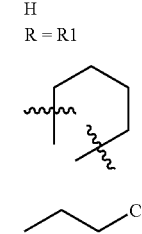 | R = R1 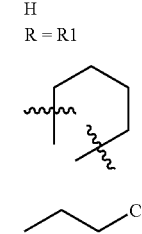 | 700 (614-799) | >1000 | 22 (17-29) | 31.8 |
| 91 | 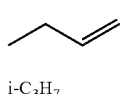 Cl | 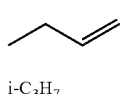 Cl | 730 (602-886) | >1000 | 23 (17-32) | 31.74 |
| 92 | t-C$_4$H$_9$ | H | 250 (166-374) | >1000 | 20 (11-36) | 12.5 |
| 93 | Adamantyl | H | 240 (193-297) | >1000 | 35 (28-43) | 7.5 |
| 94 | c-C$_6$H$_{11}$ | H | 350 (333-434) | >1000 | 23 (18-28) | 15.22 |
| 95 | c-C$_5$H$_9$ | H | 415 (304-568) | >1000 | 24 (16-36) | 17.3 |
| 96 | CH$_3$ | 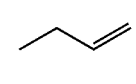 | 206 (179-238) | >1000 | 10 (6-16) | 20.6 |
| 97 | CH$_3$ | i-C$_3$H$_7$ | 325 (282-374) | >1000 | 8 (6-11) | 40.6 |
| 98 | CH$_3$ | CH$_3$ | 280 (230-342) | >1000 | 12 (10-16) | 23.33 |
| 99 | 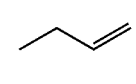 | 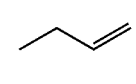 | 380 (321-451) | >1000 | 10 (5-17) | 38 |
| 100 | Et | Et | 350 (307-398) | >1000 | 9 (4-18) | 38.89 |
| 101 | R = R1 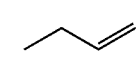 | R = R1 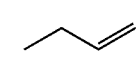 | 250 (171-364) | >1000 | 19 (14-26) | 13.16 |
| 102 | n-C$_3$H$_7$ | n-C$_3$H$_7$ | 350 (288-426) | >1000 | 14 (10-21) | 25 |

Results of adenosine receptor binding assays displacing antagonists to human $A_1$, $A_{2A}$, $A^{2B}$, and $A_3$ receptors are shown in Table 3.

TABLE 3

| R | R' | [³H] DPCPX binding to human $A_1$ receptors expressed in CHO cells Ki (nM) | [³H] SCH58261 binding to human $A_{2A}$ receptors expressed in CHO cells Ki (nM) | [³H] DPCPX binding to human $hA_{2B}$ receptors expressed in HEK293 cells Ki (nM) | [³H] MRE3008F20 binding to human $A_3$ receptors expressed in CHO cells Ki (nM) |
|---|---|---|---|---|---|
| — | Piperidin-1-yl | >1,000 | >1,000 | >1,000 | 137 |
| — | Morpholin-4-yl | >1,000 | >1,000 | >1,000 | 198 |
| H | Pyrrolidin-1-yl | >1,000 | >1,000 | >1,000 | 100 |
| H | Adamantyl | >1,000 | >1,000 | >1,000 | 310 |
| H | Cyclohexyl | >1,000 | >1,000 | >1,000 | 130 |
| H | Cyclopentyl | >1,000 | >1,000 | >1,000 | 140 |
| H | Cyclopropyl | >1,000 | >1,000 | >1,000 | 340 |
| H | Ethyl | >1,000 | >1,000 | >1,000 | 237 |
| H | tert-butyl | >1,000 | >1,000 | >1,000 | 330 |
| H | n-Pentyl | >1,000 | >1,000 | >1,000 | 886 |
| Methyl | Allyl | >1,000 | >1,000 | >1,000 | 50 |
| 2-Chloroethyl | 2-Chloroethyl | >1,000 | >1,000 | >1,000 | 120 |
| H | Benzyl | >1,000 | >1,000 | >1,000 | 303 |
| H | 4-Methoxy-phenyl | >1,000 | >1,000 | >1,000 | 573 |

Methods for the treatment of medical conditions. Also provided are methods of using the disclosed compounds for the treatment of various medical conditions.

The compounds provided by this invention are useful as potent agonists of the $A_3$ adenosine receptor. The $A_3$ adenosine receptor is thought to mediate many processes, such as inflammation, hypotension, and mast cell degranulation.

The $A_3$ receptor is believed to also play a role in the central nervous system. Mediation of the $A_3$ receptor seems to induce behavioral depression and protect against cerebral ischemia. Further, mediation of the $A_3$ adenosine receptor is also thought to induce apoptosis in HL-60 human leukemia cells.

Therefore, diseases mediated by the $A_3$ receptor would be encompassed by this invention. These would include behavioral depression, cerebral ischemia, leukemia, inflammation and inflammatory diseases such as asthma, hypotension, chemically induced seizures, cardioprotection, and ischemic heart preconditioning. These compounds can also be used as therapeutic agents in regulating cell growth, inducing apoptosis, and controlling the abnormal growth of certain tumors expressing the $A_3$ adenosine receptor. These compounds can be used to treat cancer. This particularly includes cancers that express elevated levels of A3 receptors. This would include, but not be limited to, ovarian cancer, breast cancer, colon cancer, and melanoma.

Binding assay methodology for human data with agonist radioligands. The procedures for the preparation of rat brain membranes and CHO cell membranes used herein are described in Olah et al., Mol. Pharmacol. 1994, 45, 978-982. For binding experiments, membrane homogenates were frozen and stored at −20° C. for ≦2 months. Adenosine deaminase (ADA) was obtained from Boehringer Mannheim (Indianapolis, Ind.). [³H]R-PIA was obtained from Amersham (Arlington Heights, Ill.), and [³H]CGS 21680 was obtained from DuPont NEN (Boston, Mass.). [¹²⁵I]-AB-MECA was prepared as described in Olah et al., Mol. Pharmacol. 1994, 45, 978-982.

Binding of [¹²⁵I]-AB-MECA to CHO cells stably transfected with the rat $A_3$ receptor clone or to HEK-293 cells stably expressing the human $A_3$ receptor was performed as described in Olah et al., Mol. Pharmacol. 1994, 45, 978-982. The assays were performed in 50 mM Tris/10 nM $MgCl_2$/1 mM EDTA buffer (adjusted to pH 8.26 at 5° C.) in glass tubes containing 100 μL of the membrane suspension, 50 μL of [¹²⁵I]-AB-MECA (final concentration 0.3 nM), and 50 μL of inhibitor. Inhibitors were generally dissolved in DMSO. Concentrations of DMSO in the incubations never exceeded 1%, at which concentration [¹²⁵I]-AB-MECA binding was not affected.

Incubations were carried out in duplicate for 1 h at 37° C. and were terminated by rapid filtration over Whatman GF/B filters, using a Brandell cell harvester (Brandell, Gaithersburg, Md.). Tubes were washed three times with 3 mL of buffer. Radioactivity was determined in a Beckman gamma 5500 γ-counter. Nonspecific binding was determined in the presence of 200 μM NECA. $K^i$ values were calculated according to the procedure described in Y. C. Cheng and H. R. Prusoff, Biochem. Pharmacol. 1994, 45, 1101-1111, assuming a $K_d$ for [125I]-AB-MECA of 1.48 nM.

Binding of [$^3$H]R-PIA to $A_1$ receptors from rat cortical membranes and of [$^3$H]CGS 21680 to $A_1$ receptors from rat striatal membranes was performed as described previously. Adenosine deaminase (2 units/ml) was present during the preparation of rat brain membranes. Additional deaminase was not added during incubation with the radioligand.

The compounds provided by this invention are useful as potent agonists of the $A_3$ adenosine receptor. The $A_3$ adenosine receptor is known to mediate many processes, such as inflammation, hypotension, and mast cell deregulation.

Also, the $A_3$ receptor plays a role in the central nervous system. Mediation of the $A_3$ receptor has been found to induce behavioral depression and protect against cerebral ischemia, and to induce apoptosis in HL-60 human leukemia cells.

Binding assay methodology for the human data with antagonist radioligands. The expression of the human $A_1$, $A_{2A}$ and $A_3$ receptors in CHO cells is described in Klotz et al., Naunyn Schmied. Arch. Pharmacol. 357: 1-9, (1998). The cells were grown adherently and maintained in Dulbecco's Modified Eagles Medium with nutrient mixture F12 (DMEM/F12) without nucleosides, containing 10% fetal calf serum, penicillin (100 U/ml), streptomycin (100 μg/ml), L-glutamine (2 mM) and Geneticin (G418, 0.2 mg/ml) at 37° C. in 5% CO2/95% air. Cells were split 2 or 3 times weekly at a ratio between 1:5 and 1:20. For membrane preparation the culture medium was removed and the cells were washed with PBS and scraped off T75 flasks in ice-cold hypotonic buffer (5 mM Tris HCl, 2 mM EDTA, pH 7.4). The cell suspension was homogenized with Polytron and the homogenate was spun for 10 min at 1,000×g. The supernatant was then centrifuged for 30 min at 100,000×g. The membrane pellet was resuspended in 50 mM Tris HCl buffer pH 7.4 (for $A_3$ adenosine receptors: 50 mM Tris HCl, 10 mM MgCl2, 1 mM EDTA) and incubated with 3 UI/ml of Adenosine deaminase for 30 min at 37° C. Then the suspension was frozen at −80° C. HEK 293 cells transfected with the human recombinant A2B adenosine receptor were obtained from Receptor Biology, Inc. (Beltsville, Md., USA).

Binding of [$^3$H]-DPCPX to CHO cells transfected with the human recombinant $A_1$ adenosine receptor was performed according to the method described by Klotz et al., J. Biol. Chem., 260, 14659-14664, (1985). Displacement experiments were performed for 120 min at 25° C. in 0.2 ml of 50 mM Tris HCl buffer pH 7.4 containing 1 nM [3H]-DPCPX, diluted membranes (50 μg of protein/assay) and at least 6-8 different concentrations of antagonists studied. Non-specific binding was determined in the presence of 10 μM of CHA and this was always ≦10% of the total binding.

Binding of [$^3$H]-SCH 58261 to CHO cells transfected with the human recombinant $A_{2A}$ adenosine receptors (50 μg of protein/assay) was performed using 0.2 ml 50 mM Tris HCl buffer, 10 mM MgCl2 pH 7.4 and at least 6-8 different concentrations of antagonists studied for an incubation time of 30 min at 25° C. Non-specific binding was determined in the presence of 50 μM NECA and was about 20% of total binding.

Competition experiments of [$^3$H]-DPCPX to HEK-293 cells transfected with the human recombinant $A^{2B}$ adenosine receptor were performed for 60 min at 25° C. in 0.1 ml of 50 mM Tris HCl buffer, 10 mM MgCl2, 1 mM EDTA, 0.1 mM benzamidine pH 7.4, 2 IU/ml adenosine deaminase containing 34 nM [$^3$H]-DPCPX, diluted membranes (20 μg of protein/assay) and at least 6-8 different concentrations of selected compounds. Non-specific binding was determined in the presence of 100 μM of NECA and was always ≦30% of the total binding.

Binding of [$^3$H]-MRE 3008F20 to CHO cells transfected with the human recombinant $A_3$ adenosine receptors was performed according to Varani et al., 2000. Competition experiments were carried out in duplicate in a final volume of 100 μl in test tubes containing 1 nM [$^3$H]-MRE 3008F20, 50 mM Tris HCl buffer, 10 mM MgCl$_2$, 1 mM EDTA pH 7.4 and 100 μl of diluted membranes (50 μg of protein/assay) and at least 8-10 different concentrations of examined antagonists. Incubation time was 120 min at 4° C., according to the results of previous time-course experiments. Non-specific binding was defined as binding in the presence of 1 μM MRE 3008F20 and was about 30% of total binding.

The filter bound radioactivity was counted on Top Count Microplate Scintillation Counter (efficiency 57%) with Micro-Scint 20. The protein concentration was determined with bovine albumin as a standard reference and according to the method described in Bradford, M. M. Anal. Biochem. 72, 248. Inhibitory binding constant, Ki, values were calculated from those of IC50 according to the Cheng & Prusoff equation described in Cheng, Y. C. and Prusoff, W. H., Biochem. Pharmacol. 22: 3099-3108, (1973). Ki=IC50/(1+[C*]/KD*), where [C*] is the concentration of the radioligand and KD* its dissociation constant. A weighted non-linear least-squares curve fitting program LIGAND described in Munson, P. J. and Rodboard, D., Anal. Biochem. 107, 220-239, (1980) was used for computer analysis of inhibition experiments. Data are expressed as the geometric mean, with 95% or 99% confidence limits in parentheses.

General methods of preparation of the chemical compounds. The preparation of N-substituted-sulfonamidophenyl derivatives of NECA, compounds 83-102, was performed following the general synthetic strategy depicted in FIG. 1. For the first step, 2',3'-O-isopropylidene-protected NECA and the appropriate isocyanate were dissolved in dioxane and refluxed for 18 hours. The product of the first step was heated in 1N hydrochloric acid at 65° C. in the second step.

It proved useful to protect the hydroxyl groups of the ribose moiety during the nucleophilic selective reaction with the appropriate isocyanate.

Reaction of 2',3'-O-isopropylidene-protected NECA 1a with the isocyanates in anhydrous dioxane as solvent at reflux afforded the adducts shown in the first step in FIG. 1 in a good yield, which were converted into the final desired compounds 83-102 by deprotection of the ribosyl moiety in aqueous 1N HCl and dioxane at 65° C.

Figure 2:
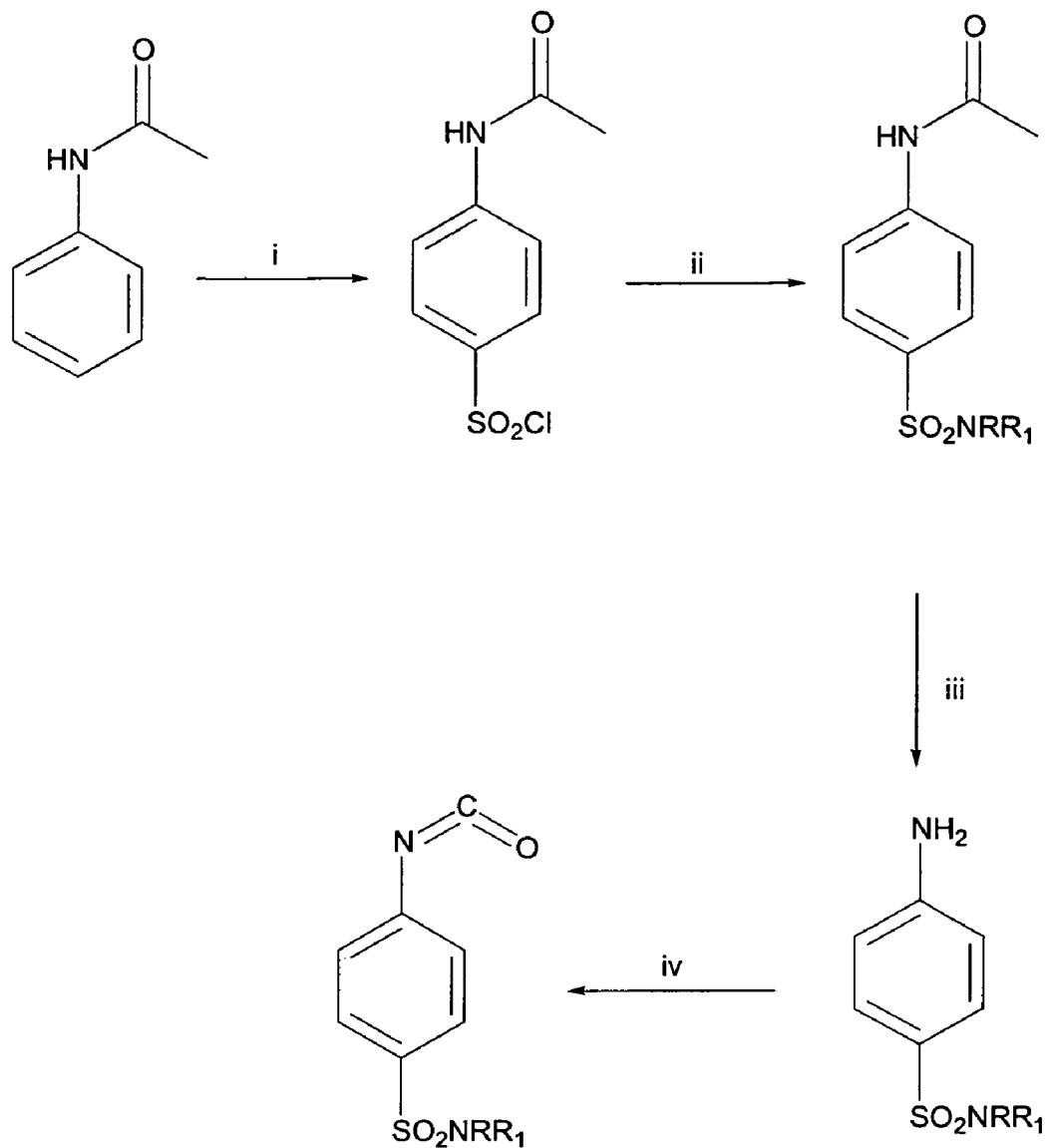
FIG. 2 shows a method of preparation of the isocyanates used to make the compounds of this invention.

The isocyanates were prepared by reacting the corresponding substituted anilines using trichloromethylchloroformate as described in Kurita et al., Organic Synthesis, Collective Vol. VI, 1988. This is shown in FIG. 2. The reagents used in FIG. 2 are as follows: for (i) HSO$^3$Cl, 100° C.; for (ii) substituted amines, dioxane; for (iii) aqueous 20% HCl; and for (iv) Cl$^3$COCOCl, dioxane.

Figure 4:
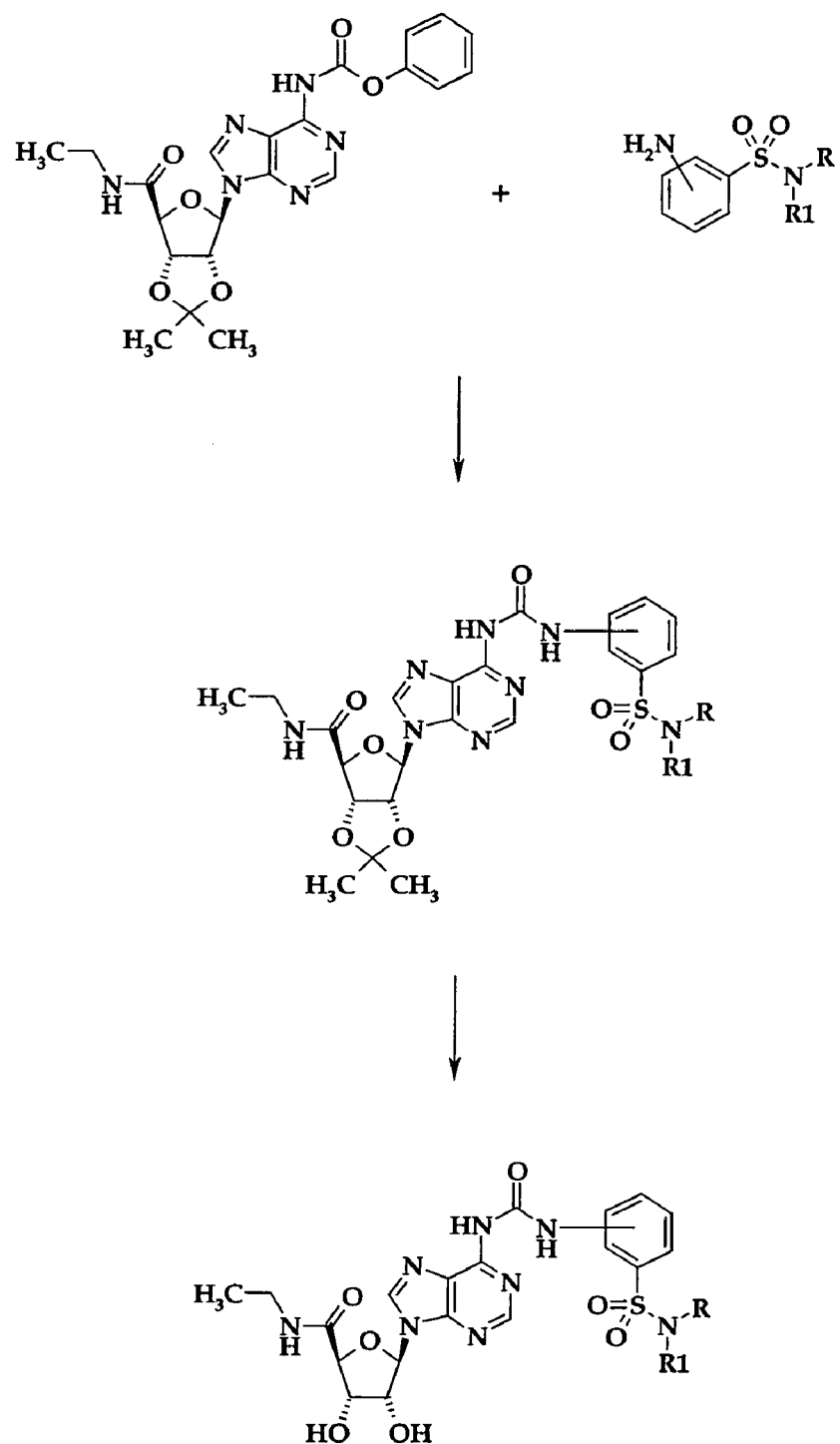
FIG. 4 is a schematic showing the preparation of exemplary compounds of this invention.

An alternative preparation of N-substituted-sulfonamidophenyl urea derivatives of NECA, Examples 61-102 and 117-128, was performed following the general synthetic strategy depicted in FIG. 4. For the first step, the N$^6$-phenylcarbamate of 2',3'-O-isopropylidene-protected NECA and the appropriate amino-phenyl-sulfonamide were dissolved in tetrahydrofuran and heated for an appropriate period to provide the intermediate N[6]-(sulfonamidophenyl)urea of 2',3'-O-isopropylidene protected NECA. The product of this first step was heated in 1N hydrochloric acid in the second step, preferably in the presence of a suitable organic cosolvent such as 1,4-dioxane, affording the desired ureas.

Figure 3:
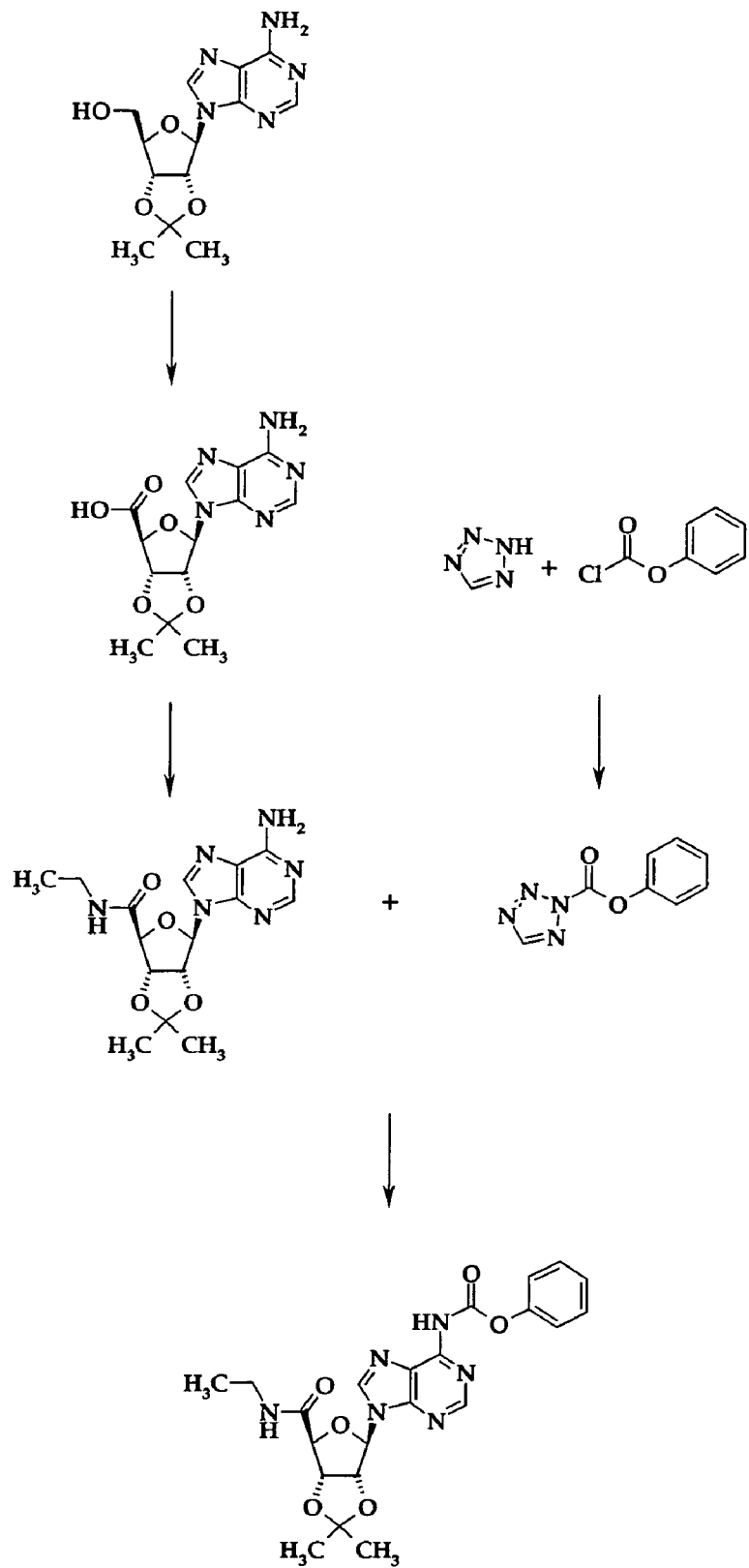
FIG. 3 is a schematic showing the preparation of exemplary compounds of this invention.

This strategy is especially useful in those cases where the intermediate sulfonamide-phenyl isocyanates would cyclize under the reaction conditions to form XXXX. Preparation of the intermediate N[6]-phenylcarbamate of 2',3'-O-isopropylidene-protected NECA followed the synthetic scheme depicted in FIG. 3. Specifically, 2',3'-O-isopropylidene adenosine was first oxidized using iodobenzene diacetate and TEMPO, to form the corresponding ribofuranuronic acid. Conversion to the desired 2',3'-O-isopropylidene-protected NECA followed by reaction with the known phenoxycarbonyl tetrazole provided the desired N[6]-phenylcarbamate of the protected-NECA.

Figure 5:
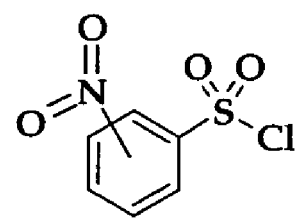
FIG. 5 is a schematic showing the preparation of exemplary compounds of this invention.
Figure 5:
Figure 5:
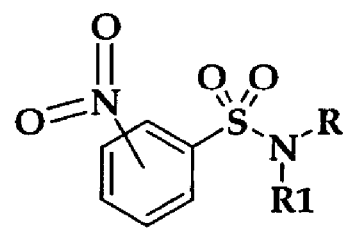
Figure 5:
Figure 5:
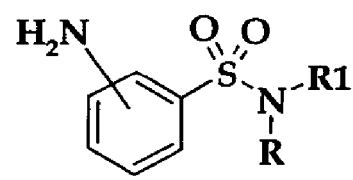

The requisite sulfonamidoanilines were prepared as depicted in FIG. 5. In the first step, the desired nitrophenyl sulfonyl chloride was reacted with the corresponding amine, affording the intermediate sulfonamides. In the second step, the nitro moiety was catalytically reduced to form the requisite sulfonamideanilines.

EXAMPLES

Example 1

Synthesis of 2',3'-O-Isopropylideneadenosine

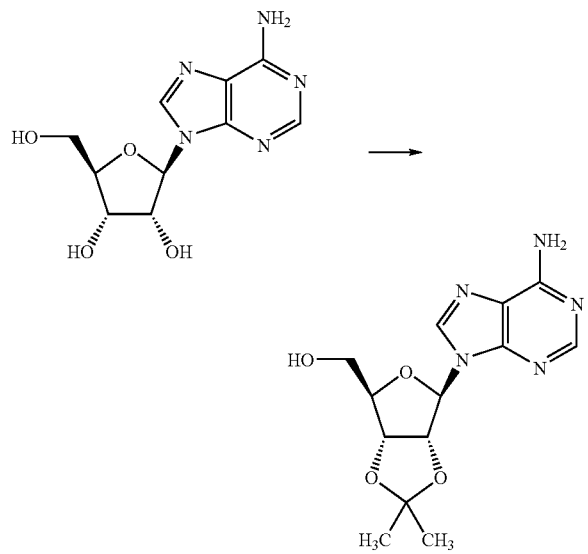

A solution of p-toluenesulfonic acid (7.79 g, 0.45 mol) in dry acetone (100 ml) is added dropwise to a solution of adenosine (10 g, 0.037 mol) in dry acetone (300 ml). 2,2-Dimethoxypropane (18.18 ml, d=0.847) is then added to the reaction mixture, and the mixture stirred for 48 hours (TLC methylene chloride/ethanol 9:1). The solution slowly becomes clear and is made basic with 3% ammonium hydroxide (800 ml). The solvent is removed at reduced pressure, keeping the temperature below 30° C. until formation of a solid that is collected by filtration. This procedure is repeated several times by concentrating the filtrate. A white solid is obtained (10.08 g, 0.0328 mol, 87.7% yield).

m.p: 228° C. $^1$H-NMR (CDCl$_3$): δ 1.38 (s, 3H); 1.65 (s, 3H); 3.79-4.02 (m, 2H); 4.55 (s, 1H); 5.10-5.13 (m, 1H); 5.18-5.24 (m, 1H); 5.84 (s, 2H); 5.87 (s, 1H); 6.57-6.63 (m, 1H); 7.84 (s, 1H); 8.32 (s, 1H). Analyzed for $C_{13}H_{17}N_5O_4$.

Example 2

Synthesis of 2',3'-O-Isopropylideneadenosine-5'-uronic acid

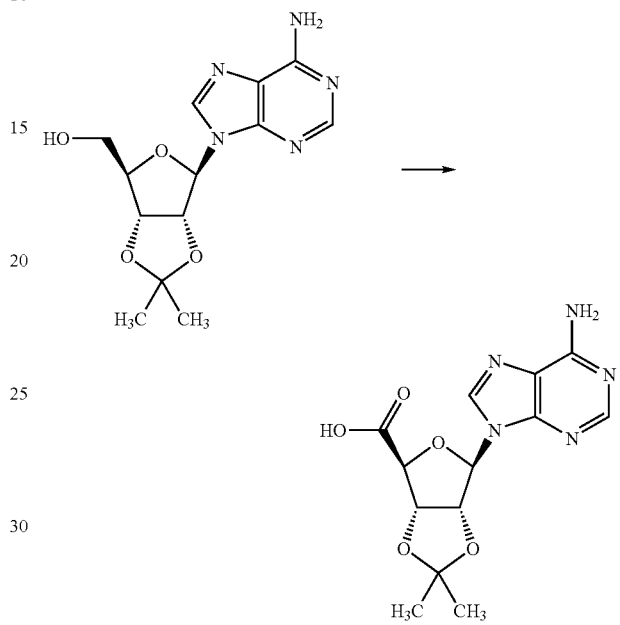

The 2',3'-O-isopropylideneadenosine (Example 1, 10.08 g, 0.033 mol) is dissolved in glacial acetic acid (300 ml) at 0° C. and solid KMnO$_4$ (11.89 g, 0.07 mol) is added slowly. After the addition, the solution is stirred at room temperature for 24 hours. It is then treated with 10% hydrogen peroxide until decolorized and the solution is concentrated at reduced pressure. The product precipitates on cooling in ice water. The precipitate (TLC Methylene chloride/Ethanol 9:1) is collected by filtration, yielding a white solid (9.4 g, 0.029 mol, 88.67% yield).

m.p: 278° C. $^1$H-NMR (CDCl$_3$, DMSO-d$_6$): δ 0.84 (s, 3H); 1.02 (s, 3H); 4.11 (s, 1H); 4.91 (m, 1H); 5.00 (m, 1H); 5.75 (s, 1H); 6.16 (bs, 2H); 7.56 (s, 1H); 7.59 (s, 1H); 10.03 (bs, 1H). Analyzed for $C_{13}H_{15}N_5O_5$.

Example 3

Synthesis of 2',3'-O-Isopropylideneadenosine-5'-ethyluronamide

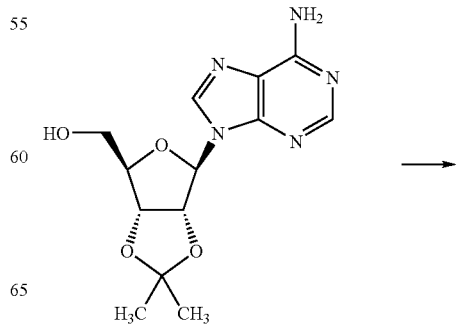

-continued

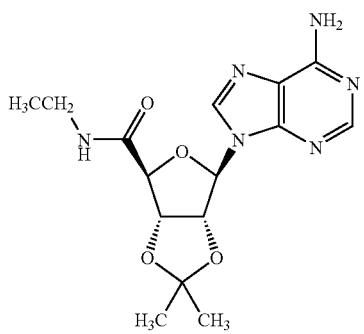

The 2',3'-O-isopropylideneadenosine-5'-uronic acid (Example 2, 9.4 g, 0.03 mol) is added quickly in small aliquots to thionyl chloride (30 ml) chilled to 0° C., then 5 drops of DMF are added. The mixture is heated to 50° C. and after 1 hour 30 minutes the solvent is removed under reduced pressure and the residue is washed several times using diethyl ether. The residue constituting the acid chloride is dissolved in methylene chloride (100 ml), the solution is chilled to 0° C., and a solution of ethylamine (39.43 ml) in methylene chloride (70 ml) is added slowly. The mixture is kept at 0° C. for 1 hour (TLC ethyl acetate/methylene chloride/methanol 8:1.5:0.5). It is then washed sequentially with aqueous $NaHCO_3$ and saline solution. The organic phase is dried with $Na_2SO_4$, evaporated, and the residue is recrystallized from a mixture of methylene chloride/diethyl ether. The product is collected as a pale yellow solid (6.7 g, 66% yield with respect to the 2',3'-O-isopropylideneadenosine-5'-uronic acid/51% yield with respect to the adenosine).

m.p: 213° C. (lit. 225-229° C). $^1$H-NMR ($CDCl_3$): δ 0.85-0.92 (t, 3H, J=8); 1.39 (s, 3H); 1.63 (s, 3H); 3.06-3.14 (m, 2H, J=2, J=6); 4.71 (s, 1H); 5.39-5.40 (m, 2H, J=2); 5.82 (bs, 2H); 6.07 (s, 1H); 6.90 (m, 1H); 7.86 (s, 1H); 8.31 (s, 1H). Analyzed for $C_{15}H_{20}N_6O_4$.

Example 4

Synthesis of 4-Acetamidobenzenesulfonyl chloride

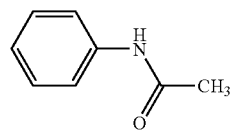

Chlorosulfonic acid (10 ml, 0.15 mol) is added dropwise slowly to acetanilide (4 g, 0.029 mol). The mixture is then heated to 100° C. for one hour. The oil that forms is cooled and carefully poured onto ice. The resulting precipitate is collected by filtration affording the desired product (3.4 g, 0.014 mol, 48% yield). The sulfonyl chloride is used directly without further purification.

Example 5

Synthesis of N-[4-(Acetylamino)phenylsulfonyl]piperidine

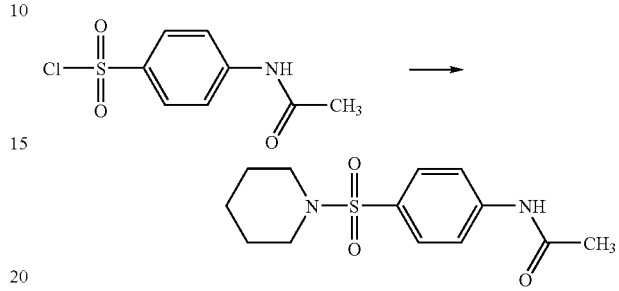

Piperidine (0.0114 Mol) is added to a solution of 4-acetamidophenylsulfonyl chloride (1.34 g, 0.0057 mol) in dioxane (5 mL). The mixture is heated for 1 hour at 80° C., then part of the solvent is removed by evaporation at reduced pressure, and water is added until precipitation of the resulting sulfonamide. The product is collected by filtration as a white solid (52.14% yield) and used without further purification. m.p. 137° C.-139° C. $^1$H NMR (acetone-$d_6$): δ 1.35-1.43 (m, 2H); 1.52-1.63 (m, 4H); 2.17 (s, 3H); 2.89-2.95 (m, 4H); 7.68-7.70 (d, 2H, J=7); 7.90-7.92 (d, 2H, J=7); 9.55 (bs, 1H). In a similar fashion, the following sulfonamides were prepared:

Example 6

N-[4-(Acetylamino)phenylsulfonyl]morpholine 67.3% yield; white solid. m.p. 165-167° C. $^1$H NMR (acetone-$d_6$):

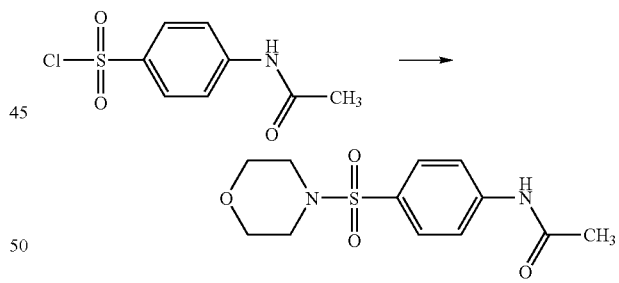

δ 2.17 (s, 3H); 2.93-3.03 (m, 4H); 3.42-3.52 (m, 4H); 7.68-7.70 (d, 2H, J=7); 7.90-7.92 (d, 2H, J=7); 9.55 (bs, 1H).

Example 7

N-[4-(Acetylamino)phenylsulfonyl]pyrrolidine

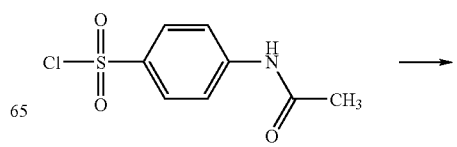

-continued

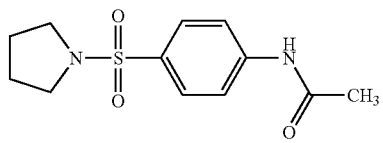

46.81% yield; white solid. m.p. 183-185° C. ¹H NMR (CDCl₃): δ 1.76 (m, 4H); 2.23 (s, 3H); 3.23 (m, 4H); 7.30 (bs, 1H); 7.69 (m, 2H); 7.78 (m, 2H).

Example 8

N-(Cyclohexyl)-4-(acetylamino)benzenesulfonamide

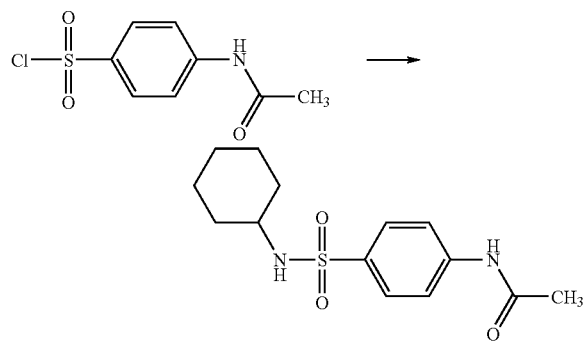

42.2% yield; white solid. m.p. 197-200° C. ¹H NMR (CDCl₃): δ 1.05-1.12, 1.53-1.55 (m, 10H); 2.20 (s, 3H); 3.1 (m, 1H); 7.77-7.75 (m, 4H).

Example 9

N-(Cyclopentyl)-4-(acetylamino)benzenesulfonamide

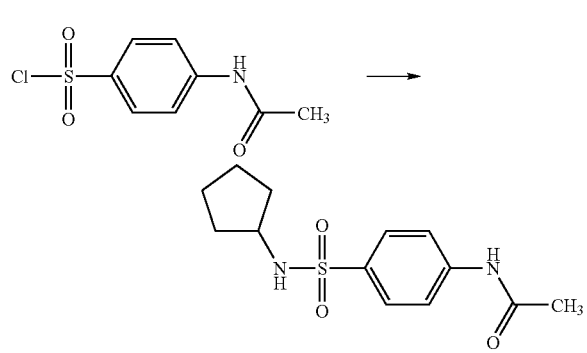

51% yield; white solid; m.p. 192-194° C. ¹H NMR (CDCl₃, DMSO-d₆): δ 1.25-1.33 (m, 4H); 1.42-1.54 (m, 4H); 2.06 (s, 3H); 3.27-3.33 (m, 1H); 7.21 (m, 1H); 7.62-7.72 (m, 4H); 10.06 (bs, 1H).

Example 10

N-(Cyclopropyl)-4-(acetylamino)benzenesulfonamide

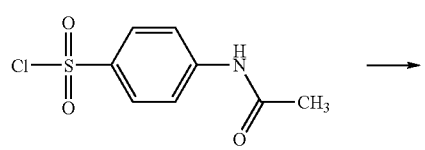

-continued

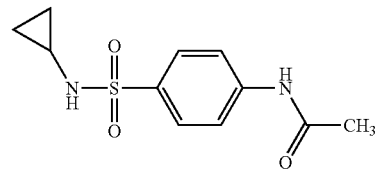

36.9% yield; yellow solid. m.p. 158-160° C. ¹H NMR (CDCl₃): δ 0.34-0.47 (m, 4H); 1.99-2.04 (m, 1H); 2.46 (s, 3H); 3.54 (m, 1H); 7.00-7.15 (m, 2H); 7.85-7.95 (m, 2H).

Example 11

N-(1,1-Dimethylethyl)-4-(acetylamino)benzene-sulfonamide

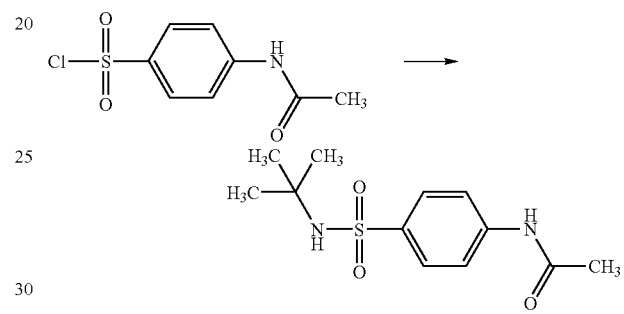

97.18% yield; white solid. m.p. 210° C. ¹H NMR (CDCl₃): δ 1.22 (s, 9H); 2.22 (s, 3H); 4.41 (bs, 1H); 7.42 (bs, 1H); 7.61-7.65 (d, 2H, J=8); 7.81-7.85 (d, 2H, J=8).

Example 12

N-(Pentyl)-4-(acetylamino)benzenesulfonamide

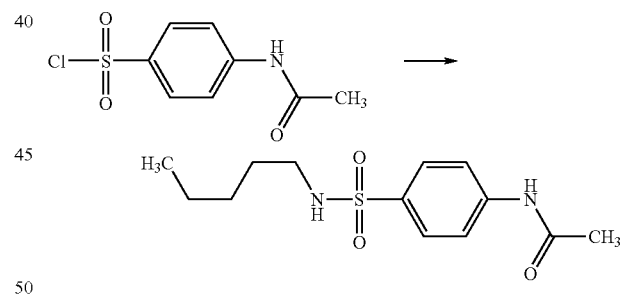

55% yield; white solid. m.p. 175-177° C. ¹H NMR (DMSO-d₆): δ 0.77-0.81 (m, 3H); 1.16-2.01 (m, 4H); 1.25-1.30 (m, 2H); 2.17 (s, 3H); 2.62-2.72 (m, 2H); 7.62 (t, 1H); 7.70 (dd, 4H); 10.25 (bs, 1H).

Example 13

N-(Allyl)-N-(methyl)-4-(acetylamino)benzene-sulfonamide

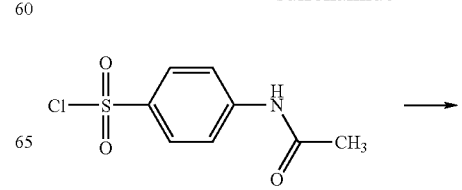

-continued

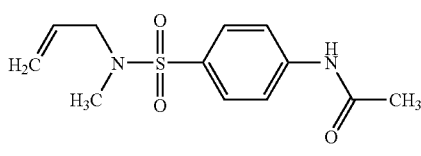

73% yield; yellow solid. m.p. 95° C. $^1$H NMR CDCl$_3$: δ 2.20 (s, 3H); 2.65 (s, 3H); 3.59-3.62 (d, 2H, J=6.24); 5.14-5.15 (d, 1H, J=2.06); 5.21-5.22 (d, 1H, J=2.12); 5.61-5.66 (m, 1H); 7.69 (m, 4H); 8.32 (s, 1H).

Example 14

N-(Benzyl)-4-(acetylamino)benzenesulfonamide

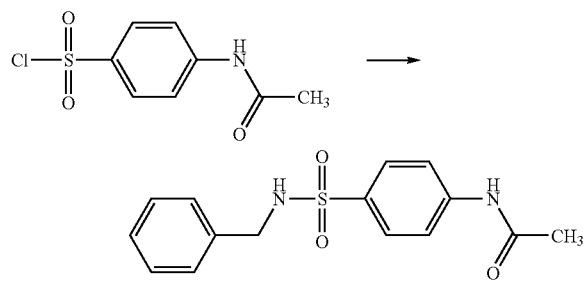

52.8% yield; white solid. m.p. 171-172° C. $^1$H NMR (acetone-d$_6$): δ 2.17 (s, 3H); 3.85 (m, 2H); 7.20-7.30 (m, 5H, J=6); 7.41 (m, 4H); 7.62 (m, 1H); 10.3 (bs, 1H).

Example 15

N-(4-Methoxyphenyl)-4-(acetylamino)benzenesulfonamide

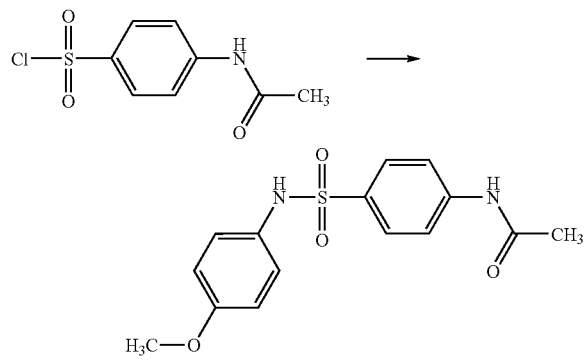

53.7% yield; yellow solid. m.p. 181-183° C. $^1$H NMR (acetone-d$_6$): δ 2.17 (s, 3H); 3.45 (s, 3H); 6.59 (d, 2H, J=8); 6.81-6.83 (d, 2H, J=8); 7.40 (bs, 1H); 7.68-7.70 (d, 2H, J=8); 7.90-7.92 (d, 2H, J=8); 9.55 (bs, 1H).

Example 16

Synthesis of N-(Ethyl)-4-(acetylamino)benzenesulfonamide

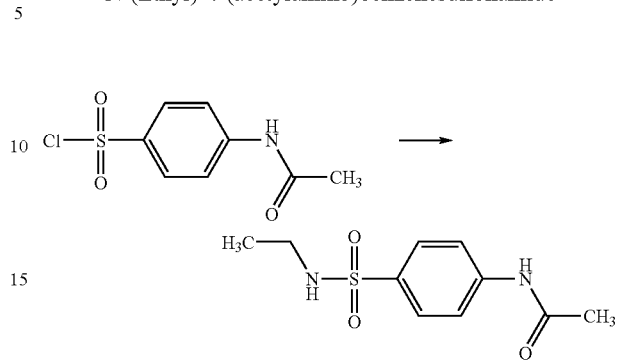

Ethylamine (0.0114 mMol) is added to a solution of 4-acetamidophenylsulfonyl chloride (1.34 g, 0.0057 mol) in dioxane (5 mL). The mixture is stirred for 1 hour at 0° C., then part of the solvent is removed by evaporation at reduced pressure, and water is added until precipitation of the resulting sulfonamide. The product is collected by filtration as a white solid in 48% yield and used without further purification.

m.p. 90-91° C. $^1$H NMR (DMSO-d$_6$): δ 0.93 (m, 3H); 2.17 (s, 3H); 2.52 (m, 2H); 7.31 (m, 1H); 7.70 (dd, 4H); 10.15 (bs, 1H).

Example 17

Synthesis of N-(1-Adamantyl)-4-(acetylamino)benzenesulfonamide

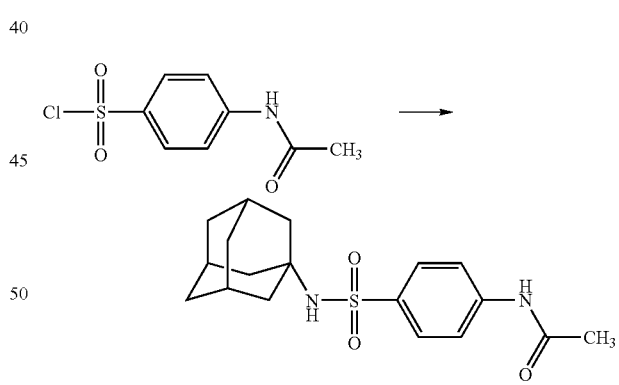

1-Adamantanamine hydrochloride (0.0114 mol) and triethylamine (0.0114 mol) are added to a solution of 4-acetamidophenylsulfonyl chloride (1.34 g, 0.0057 mol) in dioxane (5 mL). The mixture is heated for 1 hour at 80° C., then part of the solvent is removed by evaporation at reduced pressure, and water is added until precipitation of the resulting sulfonamide. The product is collected by filtration as a pink solid in 30.3% yield and used without further purification.

m.p. 290° C. $^1$H NMR (CDCl$_3$): δ 1.59 (m, 7H); 1.78 (m, 6H); 2.04 (m, 3H); 2.22 (s, 3H); 4.40 (bs, 1H); 7.40 (bs, 1H); 7.63 (m, 2H); 7.85 (m, 2H).

Example 18

Synthesis of N,N-Bis(2-chloroethyl)-4-(acetylamino)benzenesulfonamide

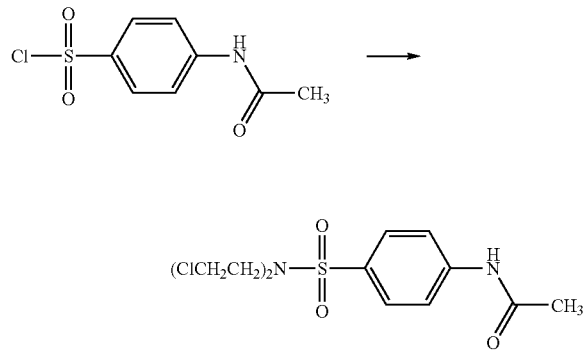

Bis(2-chloroethyl)amine hydrochloride (0.0114 mol) and triethylamine (0.0114 mol) are added to a solution of 4-acetamidophenylsulfonyl chloride (1.34 g, 0.0057 mol) in dioxane (5 mL). The mixture is heated for 1 hour at 80° C., then part of the solvent is removed by evaporation at reduced pressure, and water is added until precipitation of the resulting sulfonamide. The product is collected by filtration as a pink solid in 40.44% yield and used without further purification.

m.p. 113-114° C. $^1$H NMR (CDCl$_3$): δ 2.24 (s, 3H); 3.44-3.51 (m, 4H, J=4); 3.65-3.71 (m, 4H, J=3); 7.41 (bs, 1H); 7.67-7.82 (dd, 4H, J=8).

Example 19

Synthesis of N-[4-(Amino)phenylsulfonyl]piperidine

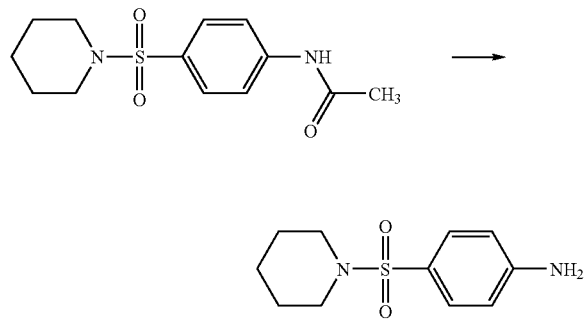

N-[4-(Acetylamino)phenylsulfonyl]piperidine (Example 5) was heated at 100° C. in 20% hydrochloric acid (5 mL) for one hour (TLC ethyl acetate/dichloromethane 8:2). The solution is neutralized at 0° C. with NaOH. The precipitate that forms is filtered and recrystallized from methanol/diethyl ether to afford the desired N-[4-(amino)phenylsulfonyl]piperidine. 70.62% yield; white solid.

m.p. 190-192° C. $^1$H NMR (acetone-d$_6$): δ 1.35-1.43 (m, 2H); 1.52-1.63 (m, 4H); 2.89-2.95 (m, 4H); 5.52 (bs, 2H); 6.78-6.80 (d, 2H, J=7); 7.45-7.47 (d, 2H, J=7). In a similar fashion the following deprotected sulfonamides were prepared:

Example 20

N-[4-(Amino)phenylsulfonyl]morpholine

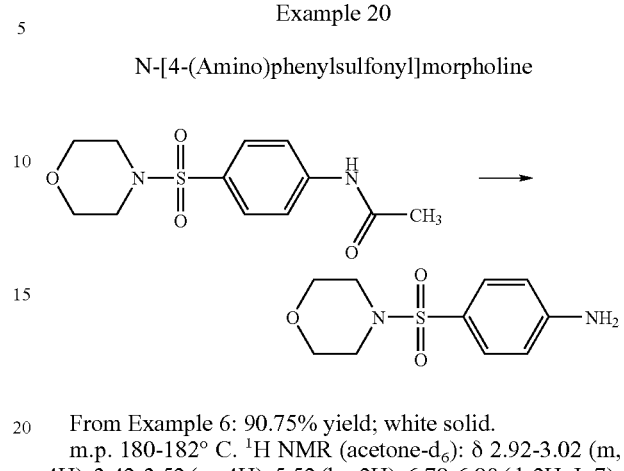

From Example 6: 90.75% yield; white solid.
m.p. 180-182° C. $^1$H NMR (acetone-d$_6$): δ 2.92-3.02 (m, 4H); 3.42-3.52 (m, 4H); 5.52 (bs, 2H); 6.78-6.80 (d, 2H, J=7); 7.90-7.92 (d, 2H, J=7).

Example 21

N-[4-(Amino)phenylsulfonyl]pyrrolidine

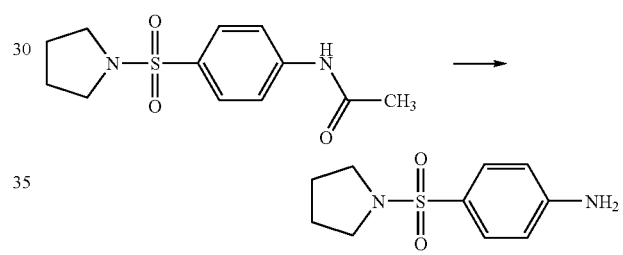

From Example 7: 52.74% yield; white solid. m.p. 172-173° C. $^1$H NMR (CDCl$_3$): δ 1.71-1.78 (m, 4H, J=3.6); 3.17-3.24 (m, 4H, J=2); 4.10 (bs, 2H); 6.68-6.72 (d, 2H, J=8); 7.59-7.64 (d, 2H, J=8).

Example 22

N-(Cyclohexyl)-4-aminobenzenesulfonamide

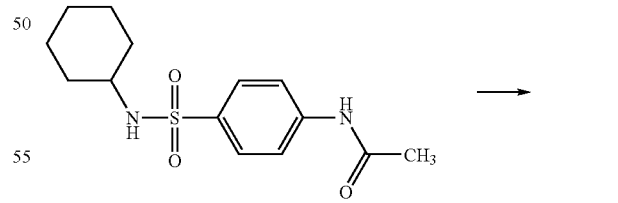

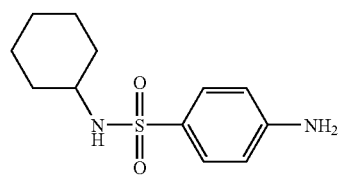

From Example 8: 42.4% yield; white solid. m.p. 165-170° C. $^1$H NMR (CDCl$_3$): δ 1.05-1.12, 1.53-1.55 (m, 10H); 2.80 (m, 1H); 4.00-4.03 (bs, 2H); 6.67-6.71 (d, 2H, J=8); 7.44-7.48 (d, 2H, J=8).

Example 23

N-(Cyclopentyl)-4-aminobenzenesulfonamide

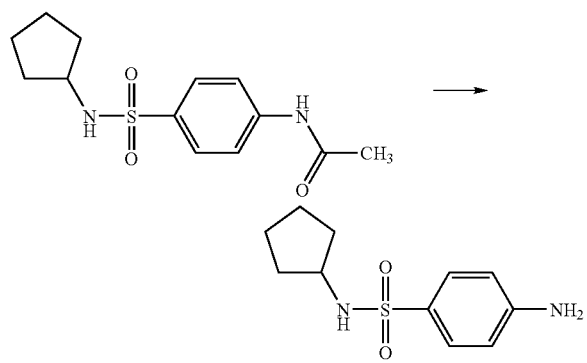

From Example 9: 13.6% yield; white solid. m.p. 110° C. $^1$H NMR (CDCl$_3$): 1.30-1.82 (m, 8H); 3.52-3.55 (m, 1H); 4.15 (bs, 2H); 4.48-4.52 (m, 1H); 6.66-6.71 (d, 2H, J=8); 7.62-7.67 (d, 2H, J=8).

Example 24

N-(Cyclopropyl)-4-aminobenzenesulfonamide

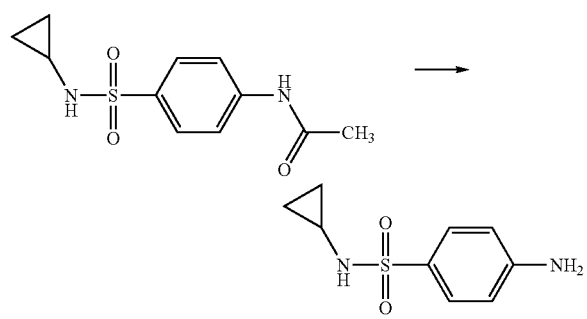

From Example 10: 13.4% yield; yellow solid m.p. 153-155° C. $^1$H NMR (CDCl$_3$): δ 0.34-0.47 (m, 4H); 1.99-2.04 (m, 1H); 3.35 (bs, 1H); 5.92 (bs, 2H); 6.59-6.63 (d, 2H, J=8); 7.39-7.44 (d, 2H, J=8).

Example 25

N,N-Bis(2-chloroethyl)-4-aminobenzenesulfonamide

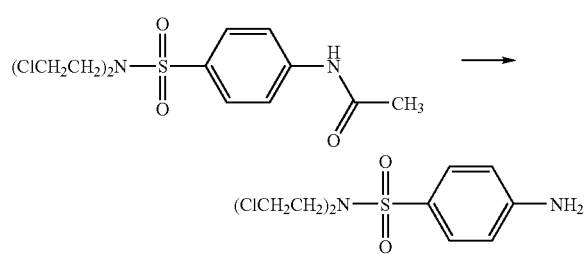

From Example 18: 26.4% yield; orange oil. $^1$H NMR (CDCl$_3$): δ 3.44-3.47 (m, 4H); 3.64-3.68 (m, 4H); 4.20 (bs, 2H); 6.68-6.72 (d, 2H, J=8); 7.59-7.63 (d, 2H, J=8).

Example 26

N-(Pentyl)-4-aminobenzenesulfonamide

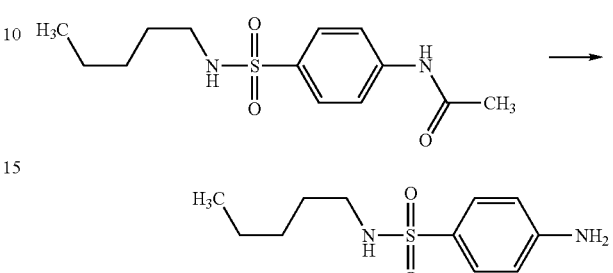

From Example 12: 93.7% yield; white solid. m.p. 193-195° C. $^1$H NMR (DMSO-d$_6$): δ 0.77-0.81 (m, 3H); 1.16-2.01 (m, 4H); 1.25-1.30 (m, 2H); 2.62-2.72 (m, 2H); 5.52 (bs, 2H); 7.62 (m, 1H); 7.70 (dd, 4H).

Example 27

N-(Allyl)-N-(methyl)-4-aminobenzenesulfonamide

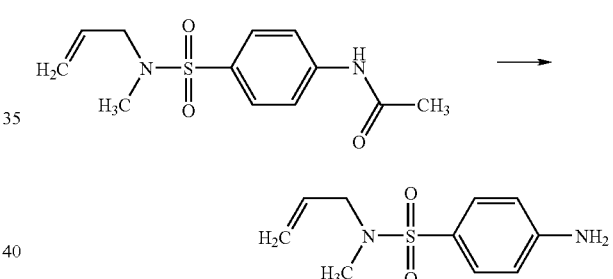

From Example 13: 67% yield; yellow solid. m.p. 155-158° C. $^1$H NMR CDCl$_3$: δ 2.63 (s, 3H); 3.58-3.61 (d, 2H, J=6.16); 4.12 (bs, 2H); 5.15 (s, 1H); 5.25 (m, 1H); 5.65-5.80 (m, 1H); 6.68-6.72 (d, 2H, J=8); 7.55-7.59 (d, 2H, J=8).

Example 28

N-(Benzyl)-4-aminobenzenesulfonamide

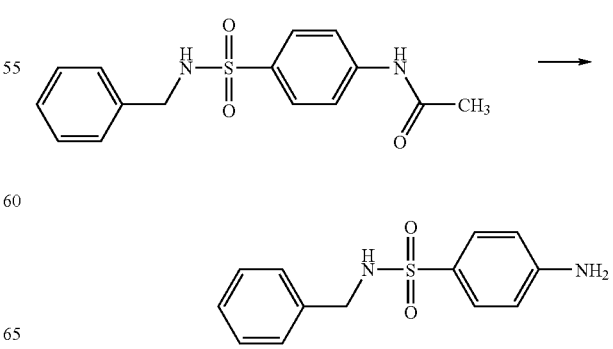

From Example 14: 82.2% yield; pale pink solid. m.p. 200-201° C. ¹H NMR (acetone-d₆): 3.85 (m, 2H); 7.20-7.30 (m, 5H, J=6); 7.62 (m, 1H); 6.67(bs, 2H); 7.71 (dd, 4H).

Example 29

N-(4-Methoxyphenyl)-4-aminobenzenesulfonamide

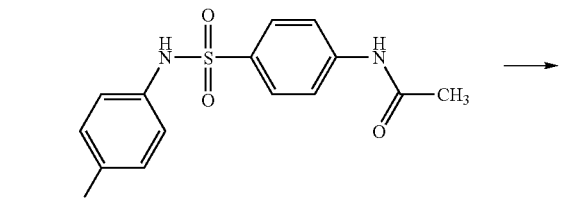

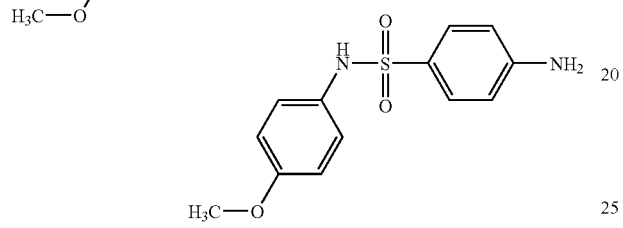

From Example 15: 62.79% yield; yellow solid. m.p. 213-215° C. ¹H NMR (acetone-d₆): δ 3.45 (s, 3H); 5.52 (bs, 2H); 6.59 (d, 2H, J=8); 6.81-6.83 (d, 2H, J=8); 7.40 (bs, 1H); 7.68-7.70 (d, 2H, J=8); 7.90-7.92 (d, 2H, J=8).

Example 30

N-(Ethyl)-4-aminobenzenesulfonamide

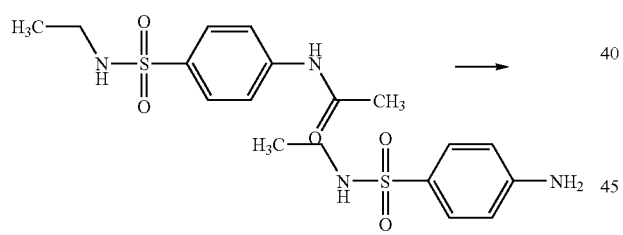

From Example 16: 95% yield; white solid. m.p. 110-112° C. ¹H NMR (DMSO-d₆): δ 0.93 (t, 3H); 2.52 (m, 2H); 5.53 (bs, 2H); 7.31 (t, 1H); 6.78-6.80 (d, 2H, J=7); 7.45-7.47 (d, 2H, J=7).

Example 31

N-(1-Adamantyl)-4-aminobenzenesulfonamide

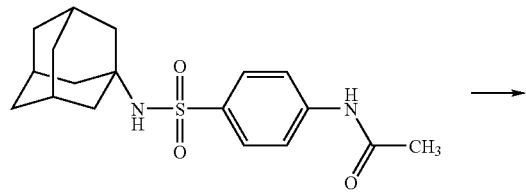

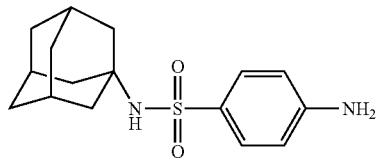

From Example 17: 12.4% yield; pink solid. m.p. 179-180° C. ¹H NMR (CDCl₃): δ 1.58 (m, 7H); 1.77-1.78 (m, 6H); 2.00 (m, 3H); 4.06 (bs, 2H); 4.25 (bs, 1H); 6.64-6.69 (d, 2H, J=8); 7.64-7.68 (d, 2H, J=8).

Example 32

N-(1,1-Dimethylethyl)-4-aminobenzenesulfonamide

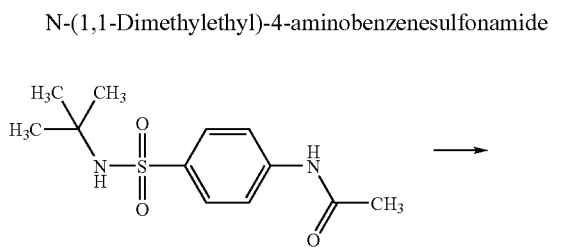

N-(1,1-Dimethylethyl)-4-(acetylamino)benzenesulfonamide (Example 11) is deprotected by saponification in 20% NaOH (5 mL), followed by neutralization with 10% HCl. The precipitate that is formed is collected by filtration and recrystallized from methanol/diethyl ether.

78.85% yield; white solid. m.p. 129-131° C. ¹H NMR (CDCl₃): δ 1.20 (s, 9H); 4.08 (bs, 2H); 4.44 (bs, 1H); 6.64-6.68 (d, 2H, J=8); 7.63-7.67 (d, 2H, J=8).

Example 33

Synthesis of N-[4-(isocyanato)phenylsulfonyl]piperidine

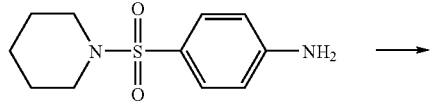

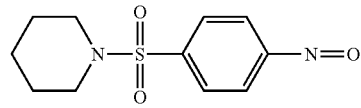

Under argon, trichloromethyl chloroformate (135 μL, 1.118 mmol) is added to N-[4-(amino)phenylsulfonyl]piperidine (Example 19, 0.572 mmol) in anhydrous 1,4-dioxane (4 mL). The solution is heated to 65° C. for 5 hours and the solvent removed at reduced pressure. The formation of the isocyanate is confirmed by infrared spectroscopy of the residue, then immediately used without further purification in the next reaction. IR (film, cm$^{-1}$): 3147, 2961, 2266, 1594, 1120, 873. In a similar fashion, the following isocyanates were prepared:

Example 34

N-[4-(Isocyanato)phenylsulfonyl]morpholine

From Example 20: IR (film, cm$^{-1}$): 2961, 2270, 1746, 1595, 1340,

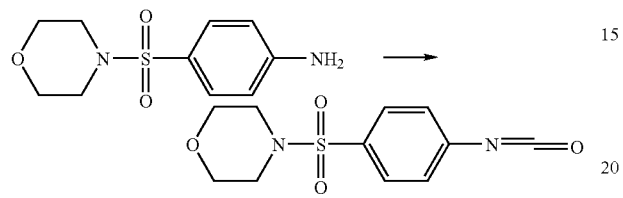

1168, 871.

Example 35

N-[4-(Isocyanato)phenylsulfonyl)pyrrolidine

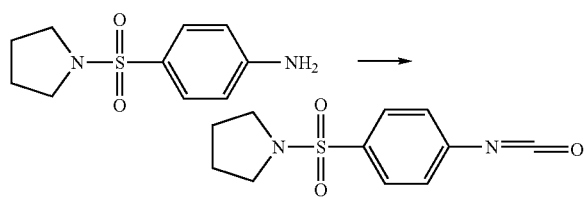

From Example 21: IR (film, cm$^{-1}$): 2963, 2268, 1593, 1345, 1121, 873.

Example 36

N-(Cyclohexyl)-4-(isocyanato)benzenesulfonamide

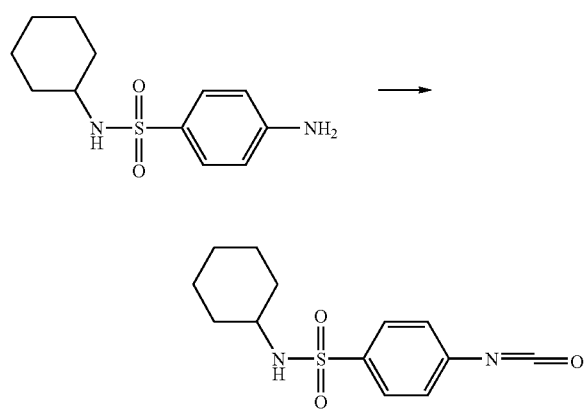

From Example 22: IR (film, cm$^{-1}$): 2854, 2266, 1366, 1254, 1120, 873.

Example 37

N-(Cyclopentyl)-4-(isocyanato)benzenesulfonamide

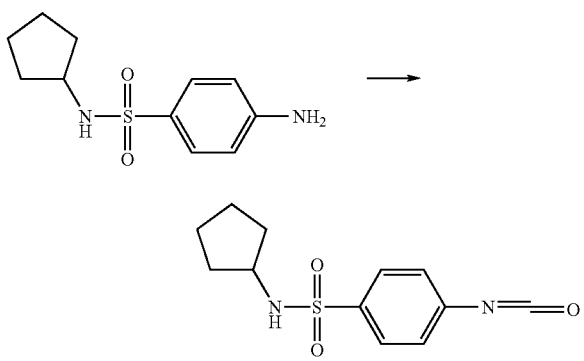

From Example 23: IR (film, cm$^{-1}$): 3247, 2926, 2266, 1772, 1594, 1120, 786.

Example 38

N-(Cyclopropyl)-4-(isocyanato)benzenesulfonamide

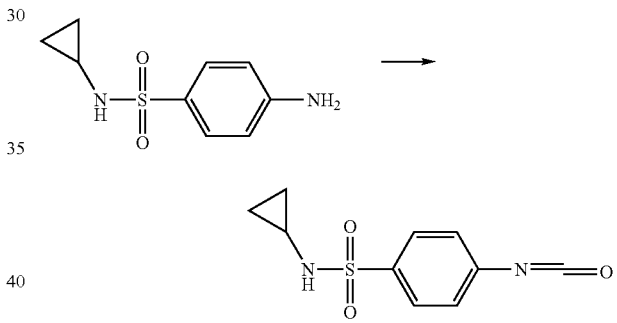

From Example 24: IR (film, cm$^{-1}$): 3205, 2961, 2267, 1594, 1255, 1120, 873, 613.

Example 39

N-(1,1-Dimethylethyl)-4-(isocyanato)benzenesulfonamide

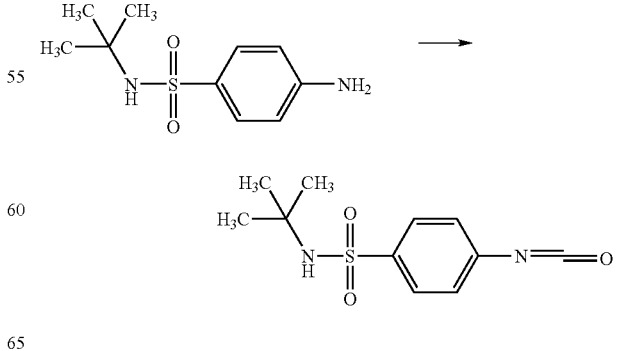

From Example 32: IR (film, cm$^{-1}$): 3273, 2974, 2268, 1771, 1595, 1323, 1155, 873.

Example 40

N-(Allyl)-N-(methyl)-4-(isocyanato)benzenesulfonamide

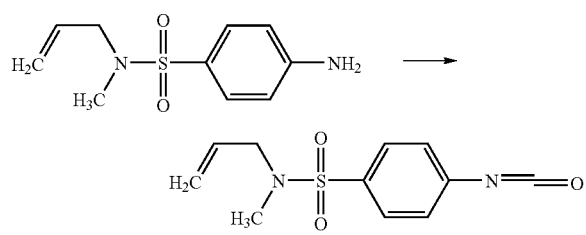

From Example 27: IR (film, cm$^{-1}$): 3294, 2856, 2267, 1770, 1594, 1338, 1161, 873.

Example 41

N-(Ethyl)-4-(isocyanato)benzenesulfonamide

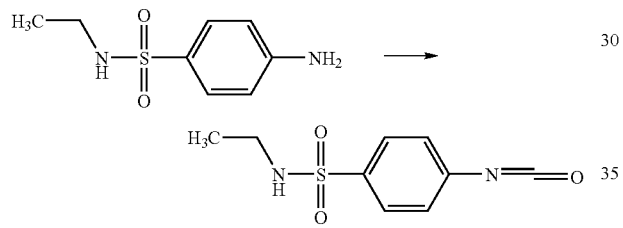

From Example 30: IR (film, cm$^{-1}$): 2963, 2271, 1594, 1300, 1120, 873.

Example 42

N-(1-Adamantyl)-4-(isocyanato)benzenesulfonamide

From Example 31: IR (film, cm$^{-1}$): 3270, 2911, 2267, 1593, 1315,

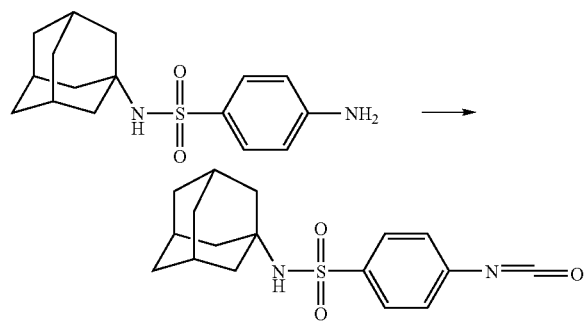

1120, 873.

Example 43

N,N-Bis(2-chloroethyl)-4-(isocyanato)benzenesulfonamide

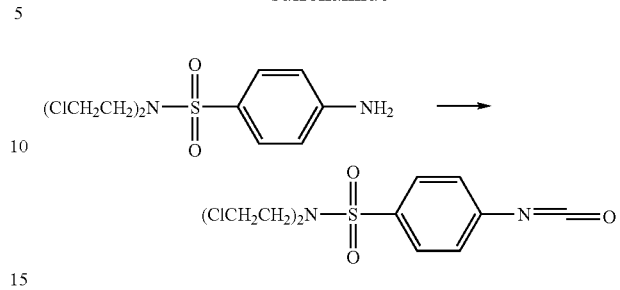

From Example 25: IR (film, cm$^{-1}$): 2964, 2268, 1770, 1594, 1345, 1161, 873.

Example 44

Synthesis of N-(pentyl)-4-(isocyanato)benzenesulfonamide

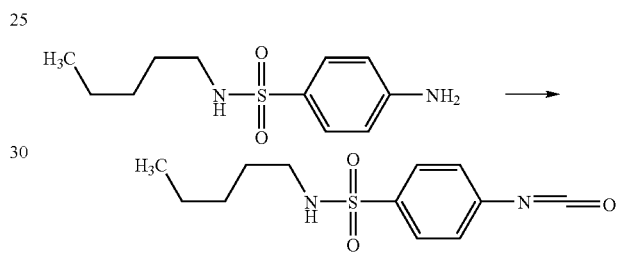

Under argon, trichloromethyl chloroformate (135 μL, 1.118 mmol) is added to N-(pentyl)-4-aminobenzenesulfonamide (Example 26, 0.572 mmol) in anhydrous acetonitrile (4 mL). The solution is heated to 65° C. for 5 hours and the solvent removed at reduced pressure. The formation of the isocyanate is confirmed by infrared spectroscopy of the residue, then immediately used without further purification in the next reaction.

From Example 26: IR (film, cm$^{-1}$): 2890, 2267, 1598, 1330, 1255, 1083, 888. In a similar fashion the following isocyanates were prepared:

Example 45

N-(Benzyl)-4-(isocyanato)benzenesulfonamide

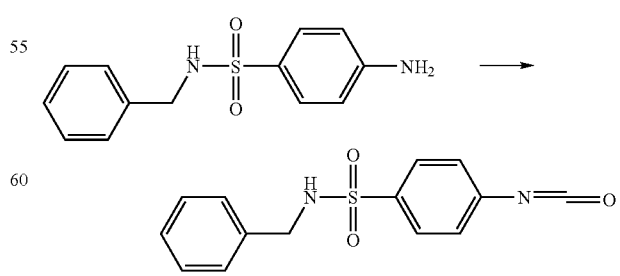

From Example 28: IR (film, cm$^{-1}$): 3021, 2227, 1539, 1234, 1130, 750, 709, 871.

Example 46

N-(4-Methoxyphenyl)-4-(isocyanato)benzenesulfonamide

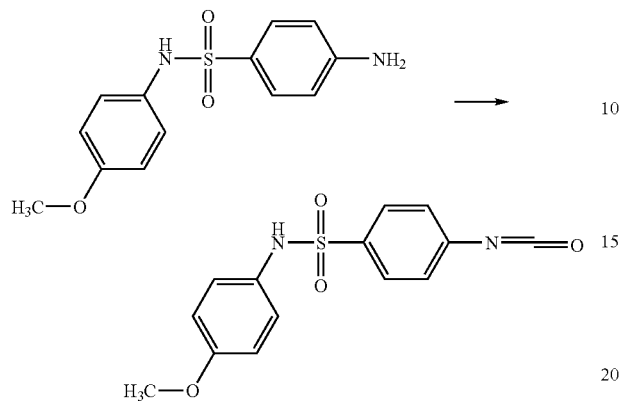

From Example 29: IR (film, cm$^{-1}$): 3010, 2968, 2250, 1756, 1520, 1150, 873.

Example 47

Synthesis of 1-deoxy-N-ethyl-2,3-O-(isopropylidene)-1-[6-[[[[4-[(piperidin-1-yl)sulfonyl]phenyl]amino]carbonyl]amino]-9H-purin-9-yl]-β-D-ribofuranuronamide

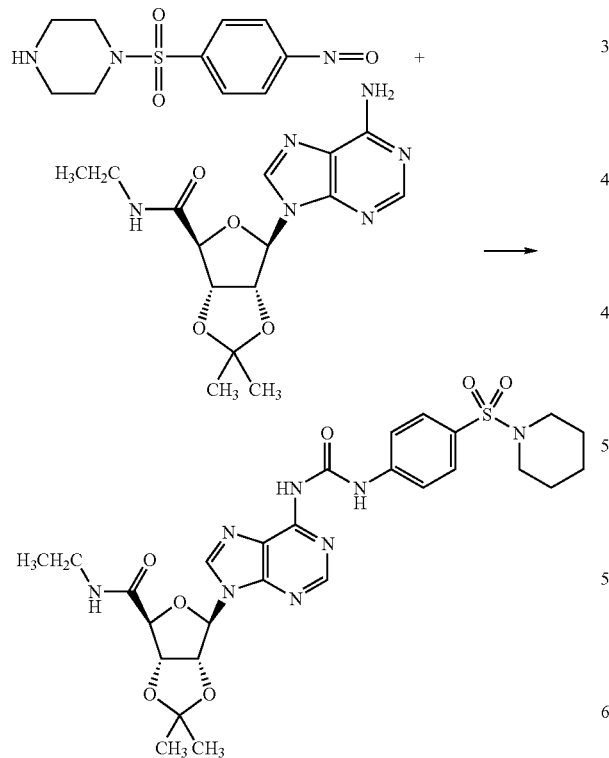

To a solution of N-[4-(isocyanato)phenylsulfonyl]piperidine (Example 33, 0.572 mmol) in 1,4-dioxane (4 mL) is added 2',3'-O-isopropylideneadenosine-5'-ethyluronamide (Example 3, 100 mg, 0.286 mmol). The mixture is heated to reflux for 18 hours and after cooling to room temperature, the solvent is evaporated at reduced pressure. The residue is purified by flash chromatography, eluting with ethylacetate:petroleum ether (8:2), to afford the desired product. 45.5% yield; white solid.

m.p. 195-197° C. $^{13}$C NMR (CD$_3$OD): δ 14.09 (CH$_3$); 24.56 (CH$_2$); 25.31 (CH$_3$); 26.38 (CH$_2$); 27.05 (CH$_3$); 34.71 (CH$_2$); 48.20 (CH$_2$); 85.28 (CH); 89.13 (CH); 92.63 (CH); 114.91 (C$^{IV°isopr.}$); 120.69 (C$^{5purine}$); 130.06 (C$^{arom}$); 131.74 (C$^{aro-SO_2}$); 143.83 (C$^{8purine}$); 145.38 (C$^{arom}$); 151.23 (C$^{4purine}$); 151.71 (C$^{6purine}$); 152.00 (C$^{2purine}$); 153.08 (CO$^{urea}$); 171.47 (CO$^{urea}$). $^1$H NMR (CD$_3$OD): δ 0.62 (t, 3H, J=7.2); 1.42 (m, 5H); 1.59 (m, 7H); 2.81-2.79 (m, 2H); 1.68 (s, 1H); 5.55 (m, 1H); 5.68 (d, 1H); 6.45 (s, 1H); 7.74-7.71 (d, 2H, J=9); 7.89-7.86 (d, 2H, J=9); 10.52 (bs, 1H); 12.10 (bs, 1H).

In a similar fashion, the following intermediates were prepared:

Example 48

1-Deoxy-N-ethyl-2,3-O-(isopropylidene)-1-[6-[[[[4-[(morpholin-4-yl)sulfonyl]-phenyl]amino]carbonyl]amino]-9H-purin-9-yl]-β-D-ribofuranuronamide

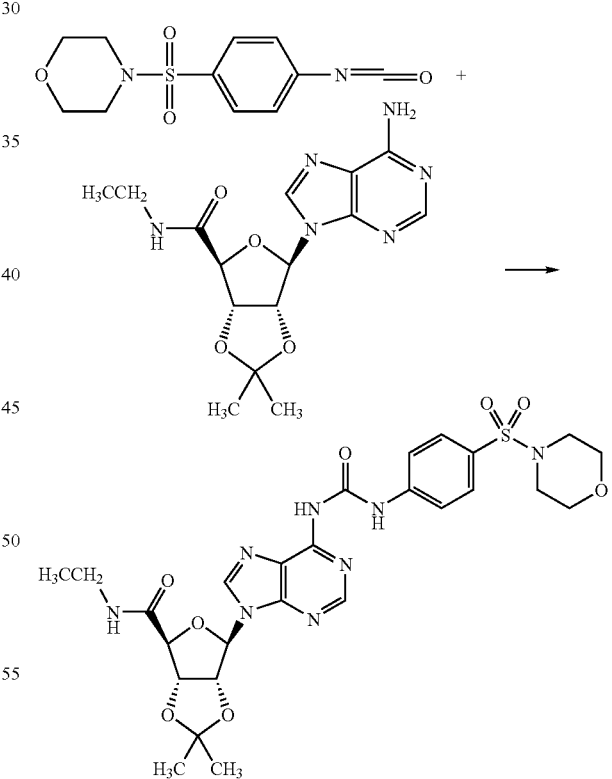

48.97% yield; white solid. m.p. 211° C. $^1$H NMR (CD$_3$OD): δ 0.63-0.58 (t, 3H, J=7.3); 1.42 (s, 3H); 1.59 (s, 3H); 2.80 (m, 2H); 2.95-2.98 (m, 4H, J=5); 3.70-3.72 (m, 4H, J=4); 4.68 (s, 1H); 5.53 (m, 1H); 5.68 (d, 1H); 6.48 (s, 1H); 7.78 (m, 2H); 7.91 (m, 2H); 8.46 (s, 1H); 8.65 (s, 1H); 10.52 (bs, 1H); 12.10 (bs, 1H).

Example 49

1-Deoxy-N-ethyl-2,3-O-(isopropylidene)-1-[6-[[[[4-[(pyrrolidin-1-yl)sulfonyl]-phenyl]amino]carbonyl]amino]-9H-purin-9-yl]-β-D-ribofuranuronamide—Compound 90

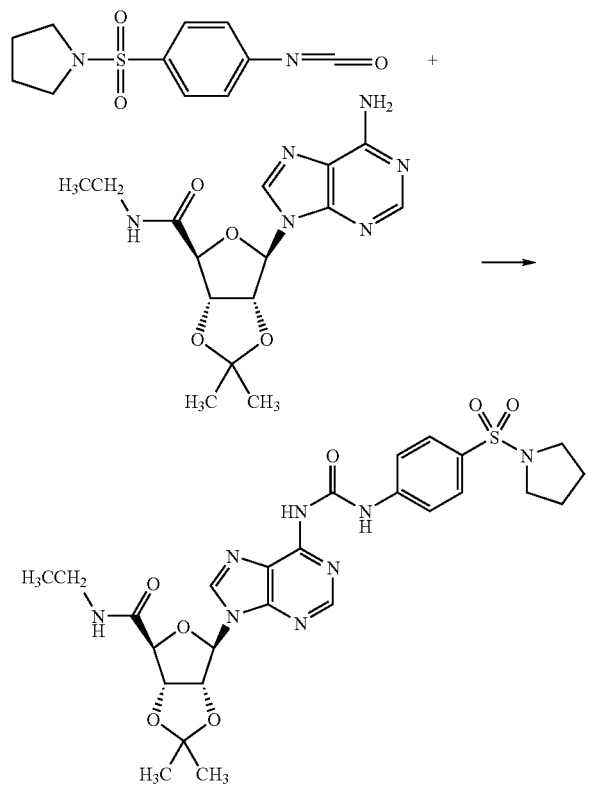

92.87% yield; white solid. m.p. 160-162° C. $^1$H NMR (DMSO-d$_6$): δ 0.54-0.61 (t, 3H, J=7.22); 1.35 (s, 3H); 1.54 (s, 3H); 1.60-1.66 (m, 4H, J=6.46); 2.75-2.78 (m, 2H); 3.11-3.12 (m, 4H, J=3.4); 4.60 (s, 1H); 5.46-5.47 (m, 2H, J=1.6); 6.47 (s, 1H); 7.60 (m, 1H); 7.76-7.89 (dd, 4H, J=8.8); 8.59 (s, 1H); 8.64 (s, 1H); 10.5 (bs, 1H); 12.10 (bs, 1H).

Example 50

1-Deoxy-N-ethyl-2,3-O-(isopropylidene)-1-[6-[[[[4-[(N-cyclohexylamino)sulfonyl]phenyl]amino]carbonyl]amino]-9H-purin-9-yl]-β-D-ribofuranuronamide

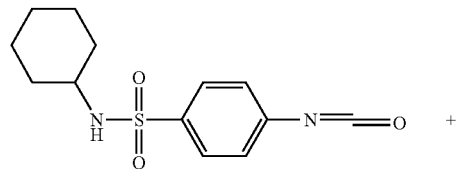

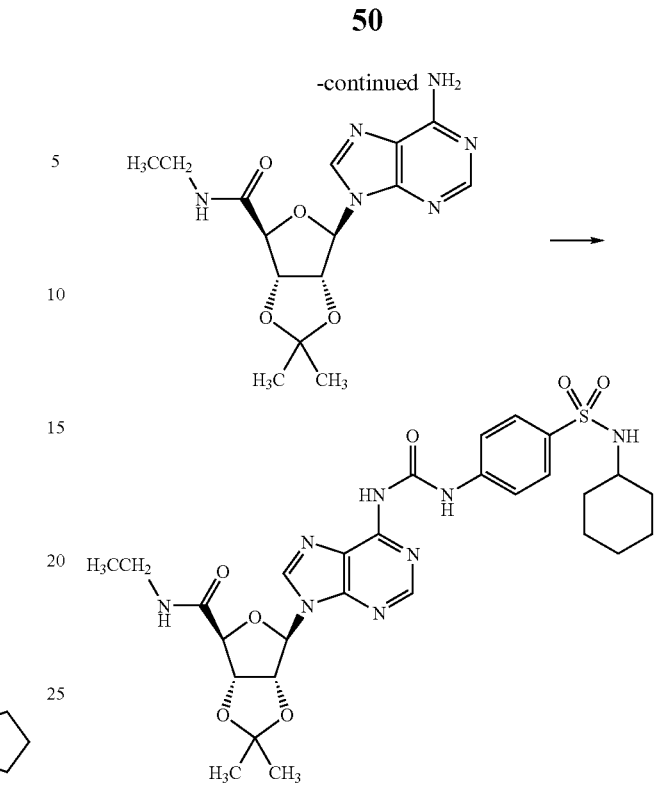

27.8% yield; white solid. m.p. 145-147° C. $^1$H NMR (DMSO-d$_6$): δ 1.05-1.12 (t, 3H, J=6.9); 1.35-1.54 (m, 16H); 2.7-2.95 (m, 3H); 4.60 (bs, 1H); 5.47 (m, 2H); 6.50 (s, 1H); 7.50-7.70 (m, 1H); 7.80 (m, 4H); 8.60 (s, 1H); 8.64 (s, 1H); 10.45 (bs, 1H); 12.06 (bs, 1H).

Example 51

1-Deoxy-N-ethyl-2,3-O-(isopropylidene)-1-[6-[[[[4-[(N-cyclopentyl-amino)-sulfonyl]phenyl]amino]carbonyl]amino]-9H-purin-9-yl]-β-D-ribofuranuronamide

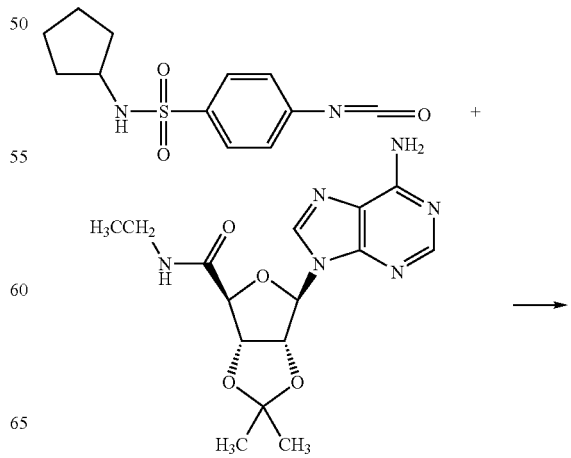

-continued

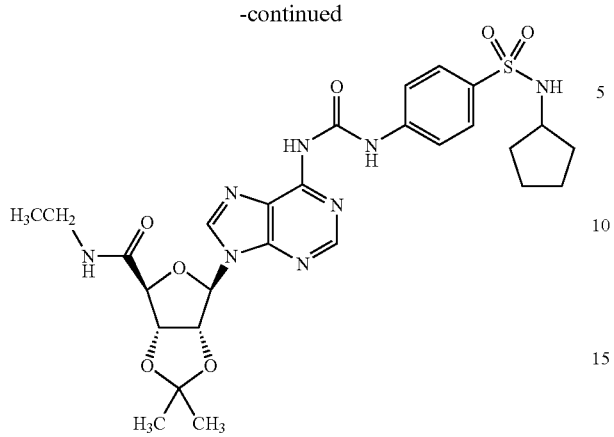

40 mg with symmetric urea; yellow oil.

Example 52

1-Deoxy-N-ethyl-2,3-O-(isopropylidene)-1-[6-[[[[4-[(N-cyclopropylamino)sulfonyl]phenyl]amino]carbonyl]amino]-9H-purin-9-yl]-β-D-ribofuranuronamide

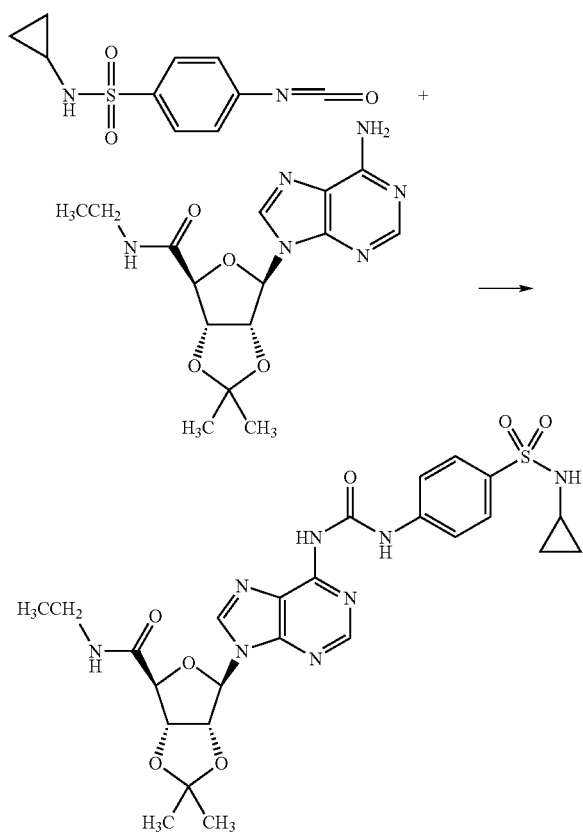

35.7% yield; white solid. m.p. 153° C. $^1$H NMR (DMSO-$d_6$): δ 0.37-0.49 (m, 4H); 0.54-0.61 (t, 3H, J=7.12); 1.36 (s, 3H); 1.54 (s, 3H); 2.10 (m, 1H); 2.75-2.78 (m, 2H); 4.60 (s, 1H); 5.47 (m, 2H); 6.47 (s, 1H); 7.61 (m, 1H); 7.76-7.88 (m, 4H); 8.60 (s, 1H); 8.64 (s, 1H); 10.47 (bs, 1H); 12.08 (bs, 1H).

Example 53

1-Deoxy-N-ethyl-2,3-O-(isopropylidene)-1-[6-[[[[4-[(N-1,1-dimethylethyl-amino)sulfonyl]phenyl]amino]carbonyl]amino]-9H-purin-9-yl]-β-D-ribofuranuronamide

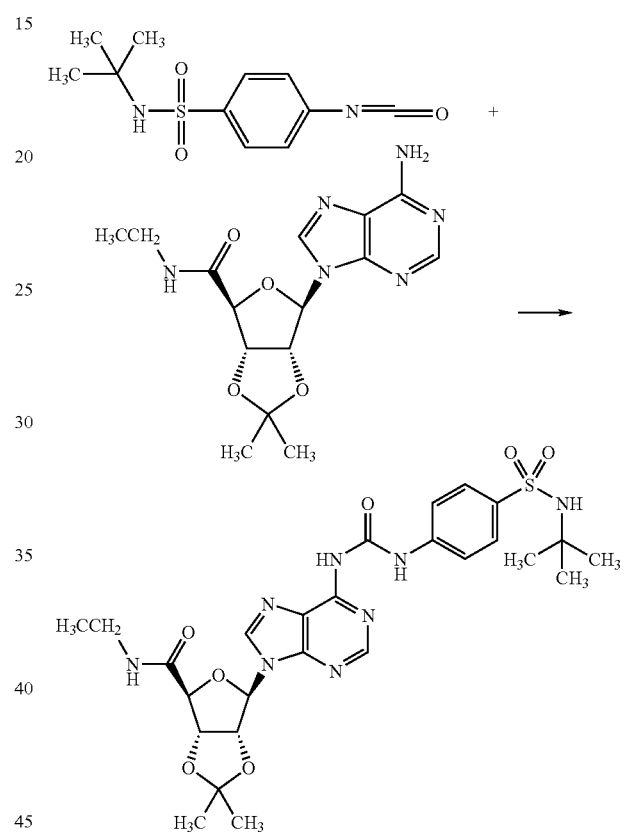

69.23% yield; gray solid. m.p. 203° C. $^1$H NMR (DMSO-$d_6$): δ 0.58-0.61 (t, 3H); 1.08 (s, 9H); 1.35 (s, 3H); 1.54 (s, 3H); 2.7-2.9 (m, 1H); 4.60 (bs, 1H); 5.47 (m, 2H); 6.46 (s, 1H); 7.4-7.5 (m, 1H); 7.59-7.63 (d, 2H, J=8.7); 7.71 (d, 2H); 8.59 (s, 1H); 8.63 (s, 1H); 10.5 (bs, 1H); 12.1 (bs, 1H).

Example 54

1-Deoxy-N-ethyl-2,3-O-(isopropylidene)-1-[6-[[[[4-[(N-allyl-N-methylamino)-sulfonyl]phenyl]amino]carbonyl]amino]-9H-purin-9-yl]-β-D-ribofuranuronamide

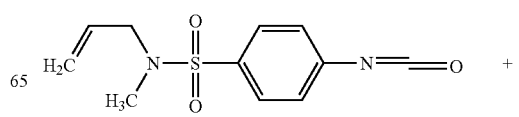

-continued

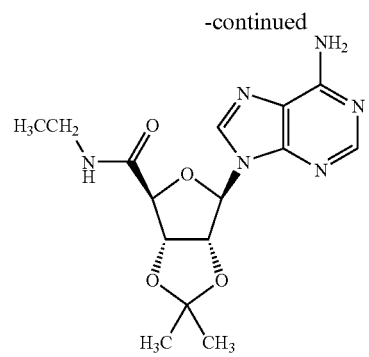

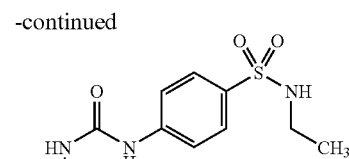

72.88% yield; white solid. m.p. 164° C. $^1$H NMR (CD$_3$OD): δ 0.62-0.64 (t, 3H, J=7.3); 1.05-1.09 (t, 3H, J=7.3); 1.43 (s, 3H); 1.60 (s, 3H); 2.75-2.82 (m, 2H); 2.89-2.91 (m, 2H); 4.70 (s, 1H); 5.53 (d, 1H); 5.68 (d, 1H); 6.48 (s, 1H); 7.81-7.82 (m, 4H); 8.46 (s, 1H); 8.65 (s, 1H); 10.52 (bs, 1H); 12.10 (bs, 1H)

Example 56

1-Deoxy-N-ethyl-2,3-O-(isopropylidene)-1-[6-[[[[4-[[N-(1-adamantyl)-amino]-sulfonyl]phenyl]amino]carbonyl]amino]-9H-purin-9-yl]-β-D-ribofuranuronamide

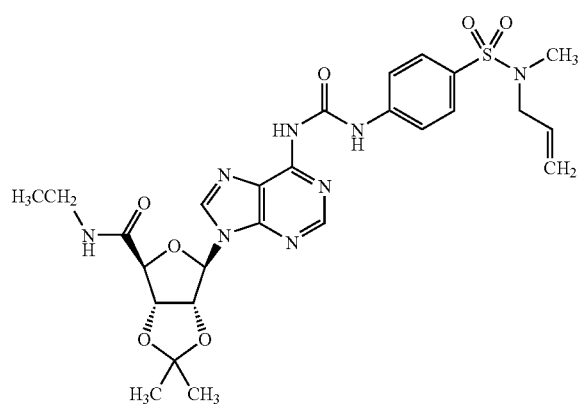

170 mg with symmetric urea; yellow solid. $^1$H NMR (DMSO-d$_6$): δ 0.58-0.61 (m, 3H); 1.35 (s, 3H); 1.54 (s, 3H); 2.49 (s, 9H); 2.57-2.58 (m, 9H); 2.72-2.90 (m, 2H); 3.31-3.33 (d, 7H, J=4.82); 3.58-3.55 (d, 7H, J=6); 4.60 (s, 1H); 5.15-5.27 (m, 2H, J=14, J=10); 5.47 (s, 1H); 5.62-5.57 (m, 1H); 6.47 (s, 1H); 7.75-7.85 (m, 4H); 8.60 (s, 1H); 8.65 (s, 1H); 9.34 (s, 1H); 10.49 (bs, 1H); 12.07 (bs, 1H).

Example 55

1-Deoxy-N-ethyl-2,3-O-(isopropylidene)-1-[6-[[[[4-[(N-ethylamino)sulfonyl]-phenyl]amino]carbonyl]amino]-9H-purin-9-yl]-β-D-ribofuranuronamide

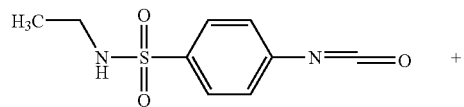

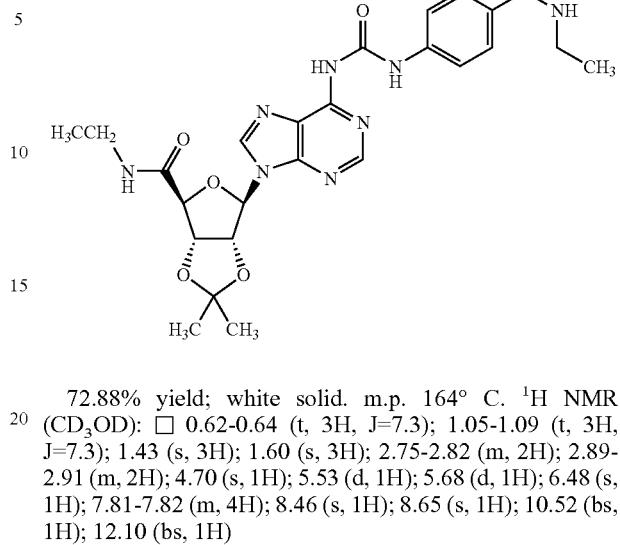

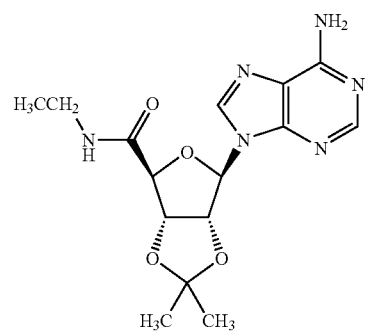

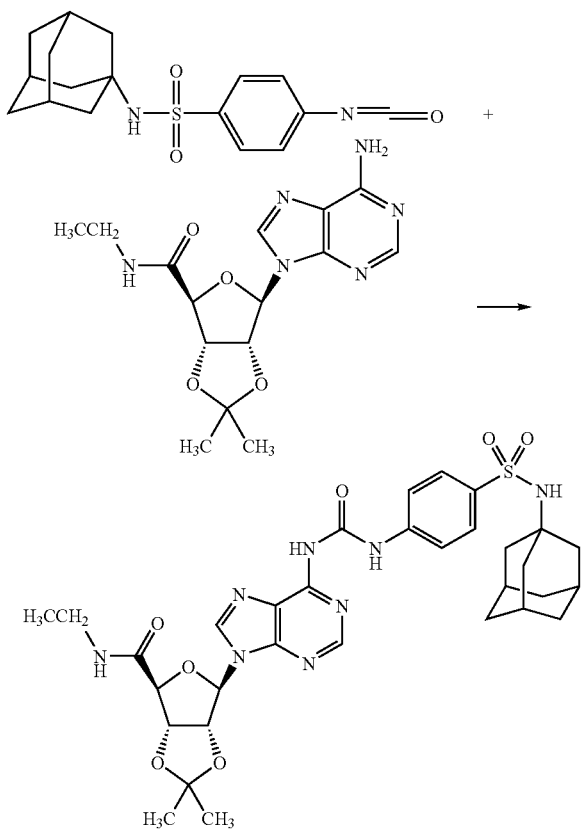

14% yield; gray solid. m.p. 164° C. $^1$H NMR (DMSO-d$_6$): δ 0.58 (m, 3H); 1.36 (s, 3H); 1.49 (m, 4H); 1.54 (s, 3H); 1.67

(m, 6H); 1.98 (m, 3H); 4.6 (bs, 1H); 5.5 (m, 2H); 6.5 (s, 1H); 7.6 (m, 1H); 7.80 (m, 4H); 8.64 (m, 2H).

Example 57

1-Deoxy-N-ethyl-2,3-O-(isopropylidene)-1-[6-[[[[4-[[N,N-bis(2-chloroethyl)-amino]sulfonyl]-phenyl]amino]carbonyl]amino]-9H-purin-9-yl]-β-D-ribofuranuronamide

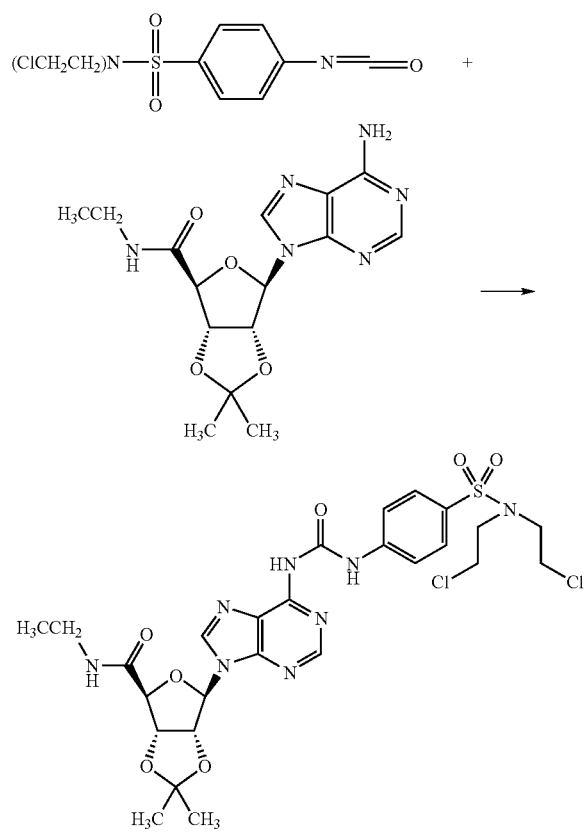

190 mg with the symmetric urea; gray solid.

Example 58

Synthesis of 1-deoxy-N-ethyl-2,3-O-(isopropylidene)-1-[6-[[[[4-[(N-pentyl-amino)sulfonyl]phenyl]amino]carbonyl]amino]-9H-purin-9-yl]-β-D-ribofuranuronamide

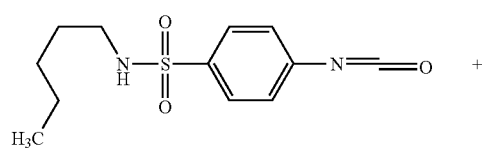

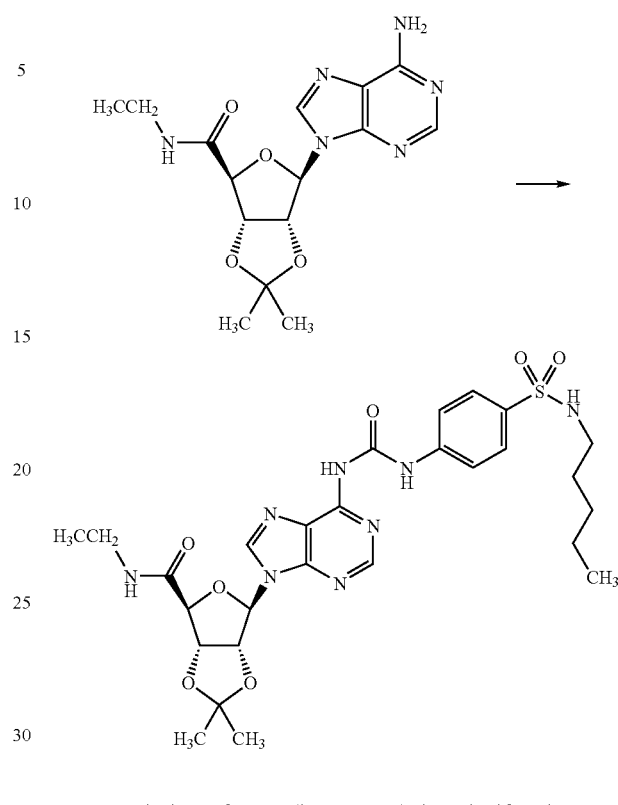

To a solution of N-[4-(isocyanato)phenylsulfonyl]pentylamine (Example 44, 0.572 mmol) in anhydrous acetonitrile (4 mL) is added 2',3'-O-isopropylideneadenosine-5'-ethyluronamide (Example 3, 100 mg, 0.286 mmol). The mixture is heated to reflux for 18 hours and after cooling to room temperature, the solvent is evaporated at reduced pressure. The residue is purified by flash chromatography, eluting with ethyl acetate: petroleum ether (8:2), to afford the desired product.

27.9% yield; yellow solid. m.p. 148-150° C. $^1$H NMR (CD$_3$OD): δ 0.63-0.58 (t, 3H, J=7.3); 0.80-0.90 (m, 3H); 1.27-1.41 (m, 4H); 1.42 (s, 3H); 1.59 (s, 3H); 2.80-2.97 (m, 6H); 4.75 (s, 1H); 5.57-5.62 (m, 2H); 6.55 (s, 1H); 7.80-7.91 (m, 4H); 8.46 (s, 1H); 8.65 (s, 1H); 10.52 (bs, 1H); 12.10 (bs, 1H).

Example 59

1-Deoxy-N-ethyl-2,3-O-(isopropylidene)-1-[6-[[[[4-[(N-(benzyl)amino]sulfo-nyl]-phenyl]amino]carbonyl]amino]-9H-purin-9-yl]-β-D-ribofuranuronamide

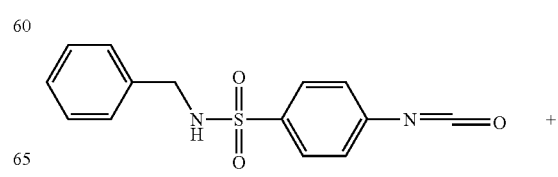

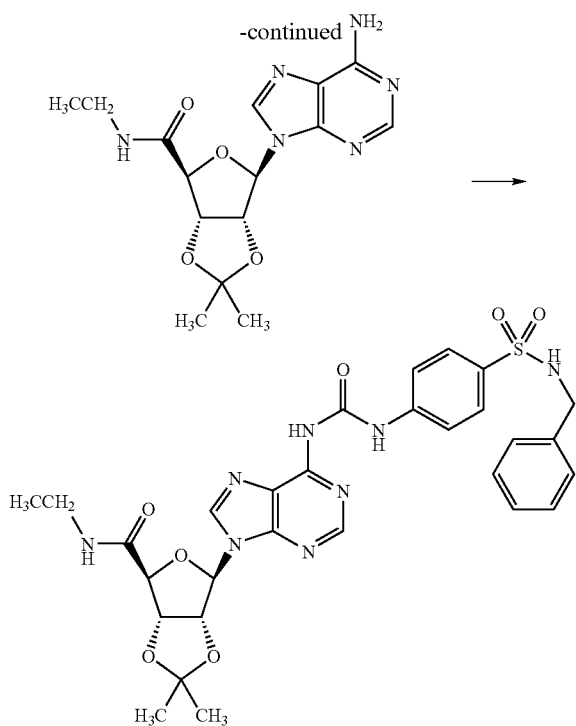
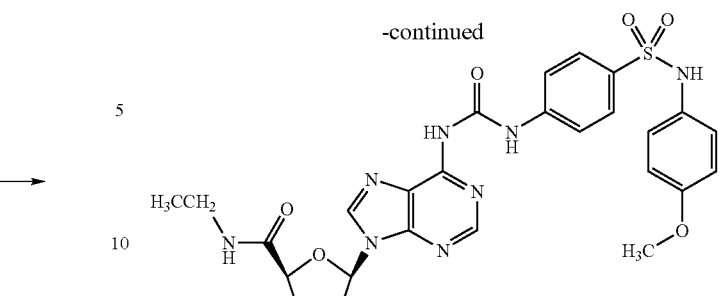

24% yield; yellow solid. m.p. 166° C. ¹H NMR (CD₃OD): δ 0.63-0.58 (t, 3H); 1.42 (s, 3H); 1.59 (s, 3H); 2.65 (m, 2H); 3.33 (bs, 2H); 4.11 (m, 1H); 5.53 (m, 1H); 5.68 (m, 1H); 6.48 (s, 1H); 7.17-7.25 (m, 5H); 7.62 (d, 2H, J=8); 7.75 (d, 2H, J=8); 7.80 (s, 1H); 8.46 (s, 1H); 8.65 (s, 1H); 10.52 (bs, 1H); 12.10 (bs, 1H).

Example 60

1-Deoxy-N-ethyl-2,3-O-(isopropylidene)-1-[6-[[[[4-[[N-(4-methoxyphenyl)-amino]sulfonyl]phenyl]amino]carbonyl]amino]-9H-purin-9-yl]-β-D-ribo-furanuronamide

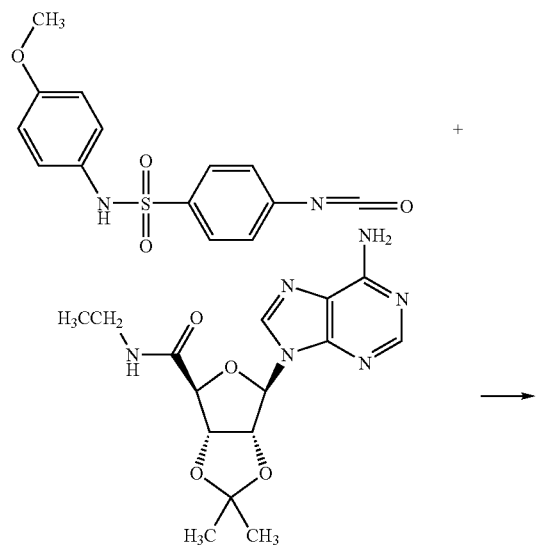

99.7% yield; white solid. m.p. 138-140° C. ¹H NMR (CD₃OD): δ 0.61 (t, 3H); 1.39 (s, 3H); 1.41 (s, 3H); 2.71 (m, 2H); 3.73 (s, 3H); 4.68 (s, 1H); 5.53 (d, 1H); 5.68 (m, 2H); 6.48 (s, 1H); 6.79 (m, 1H); 6.99 (m, 2H); 7.65 (m, 2H); 7.73 (m, 2H); 7.92 (s, 1H); 8.44 (s, 1H); 10.52 (bs, 1H); 12.10 (bs, 1H).

Example 61

Synthesis of 1-deoxy-1-[6-[[[[4-[(piperidin-1-yl)sulfonyl]phenyl]amino]carbonyl]amino]-9H-purin-9-yl]-N-ethyl-β-D-ribofuranuronamide

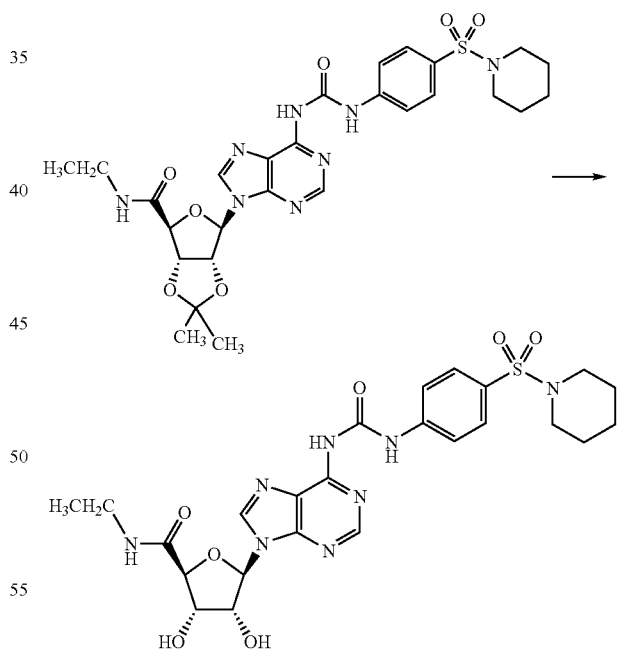

The 1-deoxy-N-ethyl-2,3-O-(isopropylidene)-1-[6-[[[[4-[(piperidin-1-yl)sul-fonyl]phenyl]amino]carbonyl]amino]-9H-purin-9-yl]-β-D-ribofuranuronamide (Example 47) is dissolved in 1N HCl (5 ml) and dioxane (5 ml). The solution thus obtained is heated to 65° C. for 1 hour. Complete reaction is verified using TLC (chloroform/methyl alcohol 95:5) and the solvent is evaporated at a reduced pressure. After adjusting the pH to neutrality, the precipitated product is collected by filtration and purified by flash-chromatography (chloroform/methyl alcohol 95:5 as eluants) to afford the desired product.

99% yield; white solid. m.p. 176-178° C. $^1$H NMR (DMSO-d$_6$): δ 1.09-1.05 (t, 3H, J=7.19); 1.35 (m, 2H); 1.52 (m, 4H); 2.86 (m, 4H); 3.16-3.26 (m, 2H); 4.23 (bs, 1H); 4.36 (s, 1H,); 4.66-4.69 (m, 1H, J=6.7); 5.65-5.68 (d, 1H, J=6); 5.77-5.79 (d, 1H, J=4.46); 6.08-6.11 (d, 1H, J=6.9); 7.72-7.68 (d, 2H, J=8); 7.86-7.89 (d, 2H, J=8); 8.49 (s, 1H); 8.73 (s, 1H); 10.50 (bs, 1H); 12.05 (bs, 1H). Satisfactory elemental analysis for C$_{24}$H$_{30}$N$_8$O$_7$S.

In a similar fashion, the following compounds were prepared:

Example 62

1-Deoxy-1-[6-[[[[4-[(morpholin-1-yl)sulfonyl]phenyl]amino]carbonyl]amino]-9H-purin-9-yl]-β-D-ribofuranuronamide—compound 84

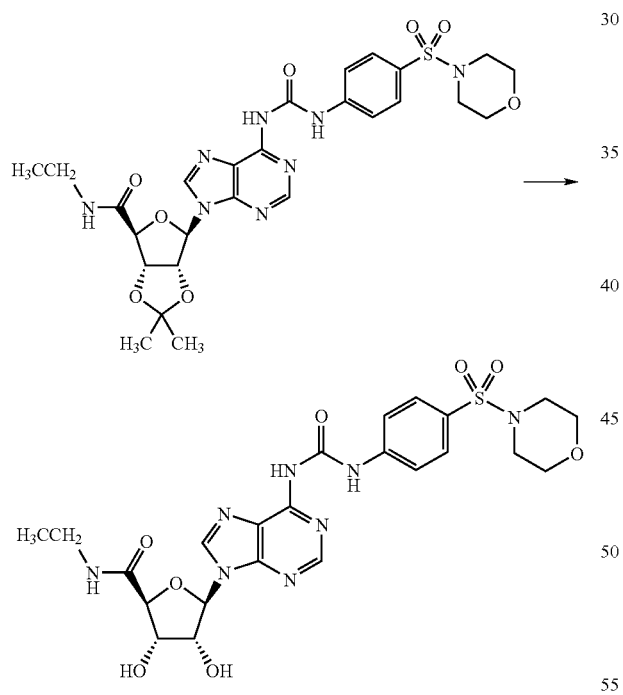

From Example 48: 97% yield; white solid. m.p. 204-205° C. $^1$H NMR (DMSO-d$_6$): ; 1.04-1.09 (t, 3H, J=7.22); 2.84-2.86 (m, 4H, J=5); 3.16-3.26 (m, 2H); 3.61-3.64 (m, 4H, J=4); 4.23 (bs, 1H); 4.36 (s, 1H); 4.66-4.69 (m, 1H, J=6.7); 5.65-5.68 (d, 1H, J=6); 5.77-5.79 (d, 1H, J=4.46); 6.08-6.11 (d, 1H, J=6.9); 7.72-7.78 (d, 2H, J=8); 7.86-7.89 (d, 2H, J=8); 8.46 (m, 1H); 8.74 (s, 1H); 8.81 (s, 1H); 10.55 (bs, 1H); 12.10 (bs, 1H). Satisfactory elemental analysis for C$_{23}$H$_{28}$N$_8$O$_8$S.

Example 63

1-Deoxy-1-[6-[[[[4-[(pyrrolidin-1-yl)sulfonyl]phenyl]amino]carbonyl]amino]-9H-purin-9-yl]-N-ethyl-β-D-ribofuranuronamide—compound 90

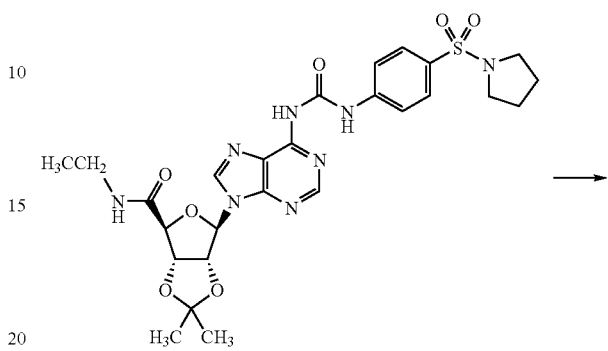

From Example 49: 99.8% yield; white solid. m.p. 204-205° C. $^1$H NMR (DMSO-d$_6$): δ 1.04-1.11 (t, 3H, J=7.2); 1.60-1.67 (m, 4H, J=6.6); 3.10-3.21 (m, 4H, J=6.48); 4.23 (bs, 1H); 4.36 (s, 1H); 4.66-4.69 (m, 1H, J=6.7); 5.65-5.69 (d, 1H, J=4.46); 5.77-5.79 (d, 1H, J=4.46); 6.08-6.11 (d, 1H); 7.77-7.90 (dd, 4H, J=8.76); 8.50 (m, 1H); 8.74 (s, 1H); 8.82 (s, 1H); 10.54 (bs, 1H); 12.12 (bs, 1H). Satisfactory elemental analysis for C$_{23}$H$_{28}$N$_8$O$_7$S.

Example 64

1-Deoxy-1-[6-[[[[4-[N-(cyclohexyl)aminosulfonyl]phenyl]-amino]carbonyl]amino]-9H-purin-9-yl]-N-ethyl-β-D-ribofuranuronamide—compound 94

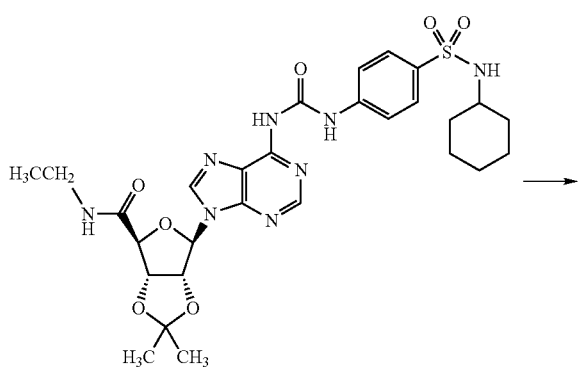

-continued

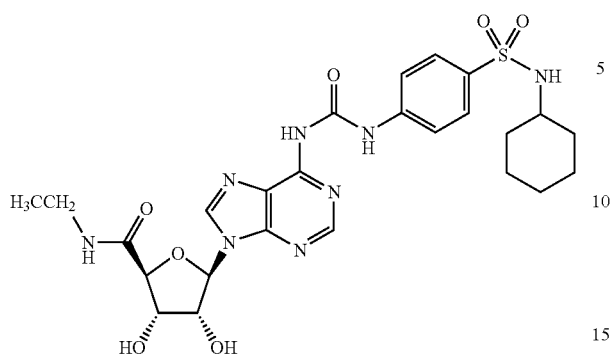

From Example 50: 99.6% yield; white solid.
m.p. 179-183° C. $^1$H NMR (DMSO-$d_6$): δ 1.04-1.54 (m, 13H); 2.90 (m, 1H); 3.20 (m, 1H); 4.20 (m, 1H); 4.36 (m, 1H); 4.65 (m, 1H); 5.60-5.75 (m, 2H); 6.10 (m, 1H); 7.50-7.70 (m, 1H); 7.79-7.81 (m, 4H); 8.55 (m, 1H); 8.72 (s, 1H); 8.80 (s, 1H); 10.45 (bs, 1H); 12.04 (bs, 1H). Satisfactory elemental analysis for $C_{25}H_{32}N_8O_7S$.

Example-65

1-Deoxy-1-[6-[[[[4-[N-(cyclopentyl)aminosulfonyl]phenyl]-amino]carbonyl]amino]-9H-purin-9-yl]-N-ethyl-β-D-ribofuranuronamide—compound 95

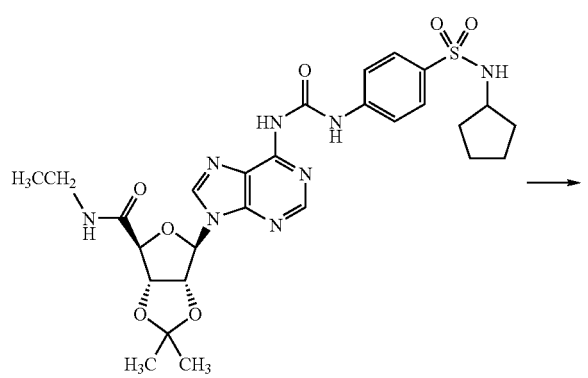

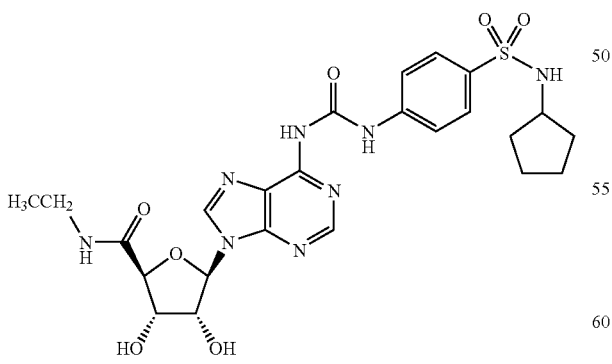

From Example 51: 98% yield; yellow solid. m.p. 176-177° C. $^1$H NMR (DMSO-$d_6$): δ 1.04-1.11 (t, 3H, J=6.97); 1.23-1.52 (m, 8H); 3.22 (m, 2H); 4.22-4.58 (m, 3H); 5.54-5.77 (m, 2H); 6.08 (m, 1H); 7.10 (m, 1H); 8.07-8.09 (m, 2H); 8.39- 8.47 (m, 2H); 8.74 (s, 1H); 8.81 (s, 1H); 10.25 (bs, 1H); 12.12 (bs, 1H). Satisfactory elemental analysis for $C_{24}H_{32}N_8O_7S$.

Example 66

1-Deoxy-1-[6-[[[[4-[N-(cyclopropyl)aminosulfonyl]phenyl]amino]carbonyl]-amino]-9H-purin-9-yl]-N-ethyl-β-D-ribofuranuronamide—compound 89

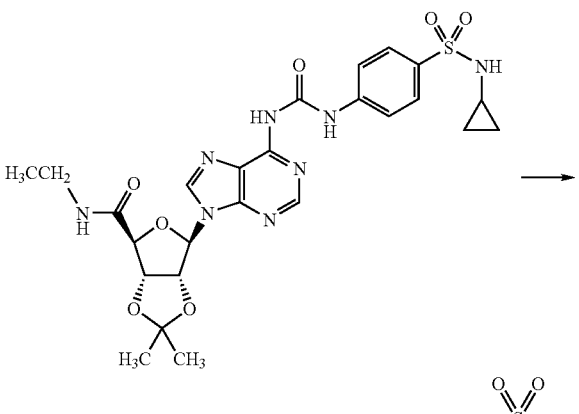

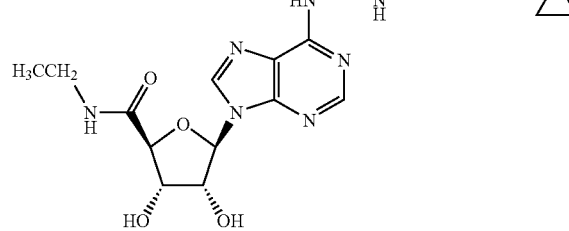

From Example 52: 96% yield; white solid. m.p. 180° C. with decomposition. $^1$H NMR (DMSO-$d_6$): δ 0.37-0.48 (m, 4H); 1.05-1.12 (t, 3H, J=7.2); 2.08-2.15 (m, 1H); 3.15-3.22 (m, 2H); 4.21 (bs, 1H); 4.35 (s, 1H); 4.63-4.69 (m, 4H); 6.05-6.09 (m, 1H); 7.36 (m, 1H); 7.74-7.88 (dd, 4H, J=8.9); 8.68 (m, 2H). Satisfactory elemental analysis for $C_{22}H_{26}N_8O_7S$.

Example 67

1-Deoxy-1-[6-[[[[4-[N-(1,1-dimethylethyl)aminosulfonyl]phenyl]amino]-carbonyl]amino]-9H-purin-9-yl]-N-ethyl-β-D-ribofuranuronamide—compound 92

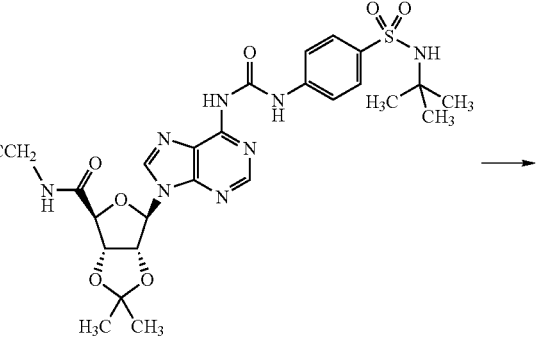

-continued

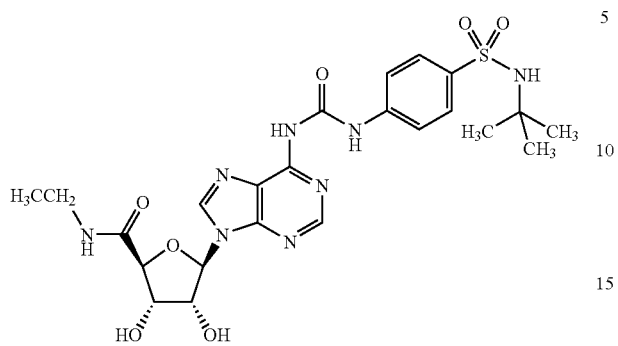

From Example 53: 97% yield; gray solid. m.p. 185° C. $^1$H NMR (DMSO-d$_6$): δ 1.04-1.11 (m, 12H); 3.15 (m, 2H); 4.2 (bs, 1H); 4.36-4.37 (s, 1H); 4.66 (m, 1H); 6.09-6.12 (m, 1H); 7.4 (m, 1H); 7.58-7.63 (d, 2H, 8.96); 7.71-7.75 (d, 2H, J=8.9); 8.5 (m, 1H); 8.75 (s, 1H); 8.90 (s, 1H); 9.67 (bs, 1H); 11.91 (bs, 1H). Satisfactory elemental analysis for C$_{23}$H$_{30}$N$_8$O$_7$S.

Example 68

1-Deoxy-1-[6-[[[[4-[N-(pentyl)aminosulfonyl]phenyl]-amino]carbonyl]amino]-9H-purin-9-yl]-N-ethyl-β-D-ribofuranuronamide—compound 87

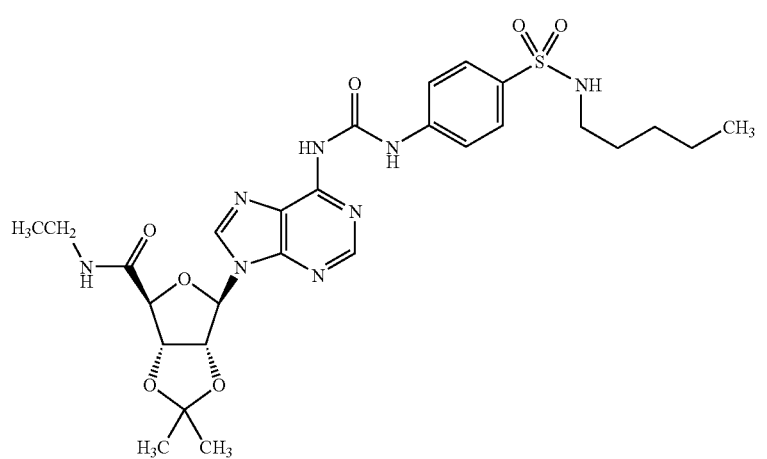

From Example 58: 98.6% yield; yellow solid. m.p. 199° C. $^1$H NMR (DMSO-d$_6$): δ 0.79 (t, 3H); 1.04-1.09 (t, 3H, J=7.22); 1.15-1.20 (m, 2H); 1.32-1.43 (m, 2H); 2.68-2.78 (m, 2H); 3.16-3.26 (m, 2H); 4.23 (bs, 1H); 4.36 (s, 1H); 4.66-4.69 (m, 1H, J=6.7); 6.08-6.11 (d, 1H, J=6.9); 7.45 (m, 1H); 7.80 (dd, 4H, J=8); 8.84 (m, 1H); 8.73 (s, 1H); 8.85 (s, 1H); 10.5 (bs, 1H); 12.00 (bs, 1H). Analysis Satisfactory elemental analysis for C$_{24}$H$_{32}$N$_8$O$_7$S.

Example 69

1-Deoxy-1-[6-[[[[4-[N-(allyl)-N-(methyl)aminosulfonyl]phenyl]amino]carbo-nyl]amino]-9H-purin-9-yl]-N-ethyl-β-D-ribofuranuronamide—compound 96

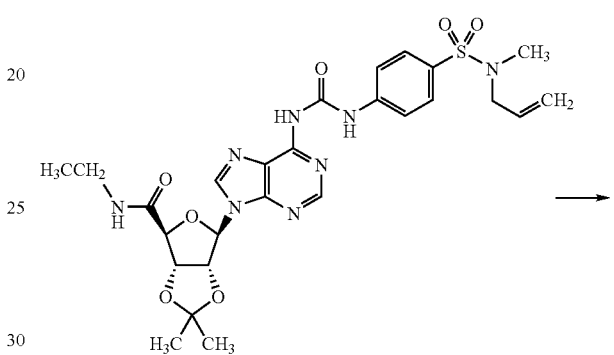

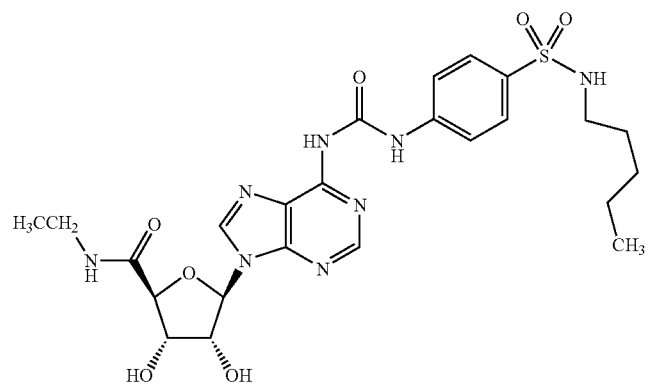

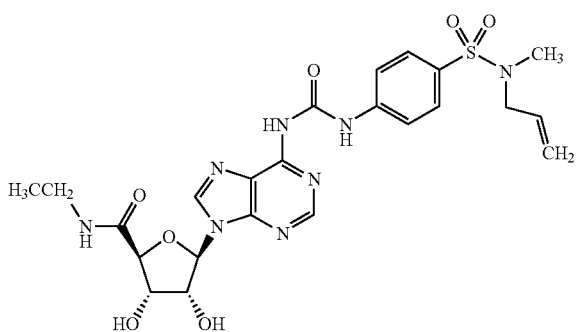

From Example 54: 97.9% yield, yellow solid. m.p. 181-185° C. $^1$H NMR (DMSO-$d_6$): δ 1.04-1.11 (t, 3H, J=6); 3.16-3.26 (m, 2H); 3.57-3.60 (d, 2H, J=6); 4.22 (bs, 1H); 4.36-4.37 (m, 1H); 4.66 (m, 1H); 5.15-5.27 (m, 2H, J=8, J=14); 5.67-5.77 (m, 3H); 6.08-6.12 (d, 1H, J=8); 7.75-7.79 (d, 2H, J=8); 7.86-7.91 (d, 2H, J=8); 8.47-8.49 (m, 1H); 8.74 (s, 1H); 8.82 (s, 1H); 12.08 (bs, 1H). Satisfactory elemental analysis for $C_{23}H_{28}N_8O_7S$.

Example 70

1-Deoxy-1-[6-[[[[4-[N-(benzyl)aminosulfonyl]phenyl]amino]carbonyl]amino]-9H-purin-9-yl]-N-ethyl-β-D-ribofuranuronamide

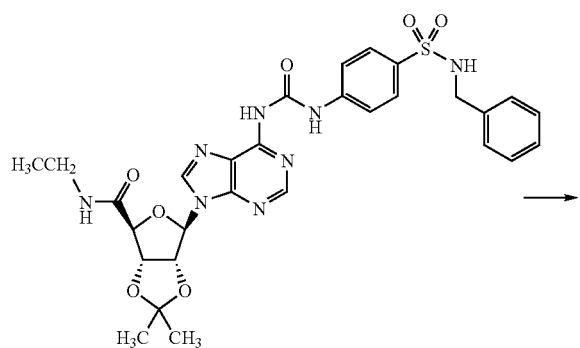

From Example 59: 98% yield; yellow solid. m.p. 175° C. $^1$H NMR (DMSO-$d_6$): δ 1.04-1.09 (t, 3H, J=7.2); 3.16-3.26 (m, 2H); 4.00 (d, 1H); 4.23 (bs, 1H); 4.36 (s, 1H); 4.66-4.69 (m, 1H); 6.11 (d, 1H); 7.15-7.29 (m, 5H); 7.72-7.85 (m, 4H); 8.07 (m, 1H); 8.48 (m, 1H); 8.74 (s, 1H); 8.81 (s, 1H); 12.00 (bs, 1H). Satisfactory elemental analysis for $C_{26}H_{28}N_8O_7S$.

Example 71

1-Deoxy-1-[6-[[[[4-[N-(4-methoxyphenyl)aminosulfonyl]phenyl]amino]carbo-nyl]amino]-9H-purin-9-yl]-N-ethyl-β-D-ribofuranuronamide—compound 88

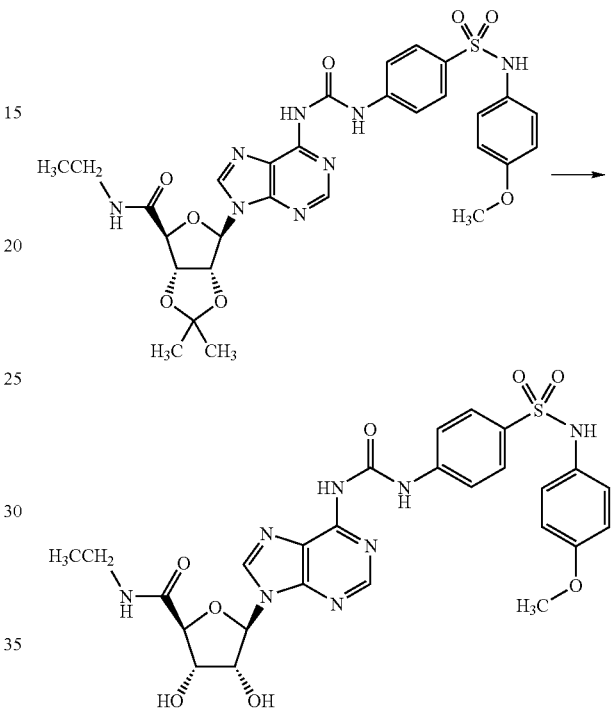

From Example 60: 9.8% yield; yellow solid. m.p. 175° C. $^1$H NMR (DMSO-$d_6$): δ 1.04-1.09 (t, 3H, J=7.2); 3.16-3.26 (m, 2H); 4.00 (d, 1H); 4.23 (bs, 1H); 4.36 (s, 1H); 4.66-4.69 (m, 1H); 6.11 (d, 1H); 7.15-7.29 (m, 5H); 7.72-7.85 (m, 4H); 8.07 (m, 1H); 8.48 (m, 1H); 8.74 (s, 1H); 8.81 (s, 1H); 12.00 (bs, 1H). Satisfactory elemental analysis for $C_{26}H_{28}N_8O_7S$.

Example 72

1-Deoxy-1-[6-[[[[4-[N-(ethyl)aminosulfonyl]phenyl]amino]carbonyl]amino]-9H-purin-9-yl]-N-ethyl-β-D-ribofuranuronamide—compound 85

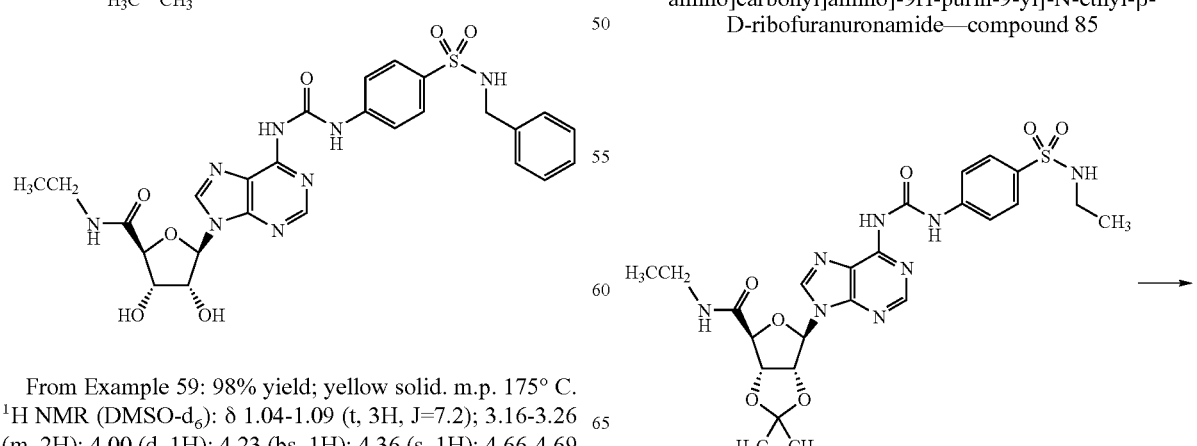

-continued

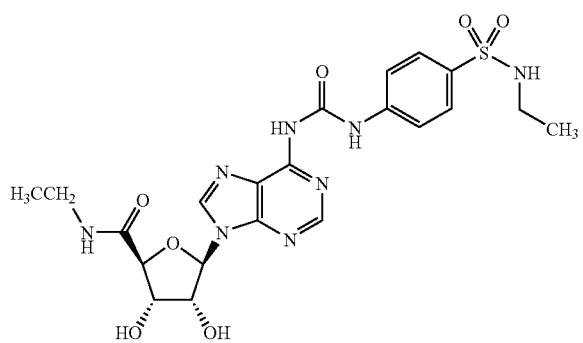

From Example 55: 99.7% yield; yellow solid. m.p. 180-183° C. $^1$H NMR (DMSO-d$_6$): δ 0.96 (t, 3H, J=7); 1.07 (t, 3H, J=7.2); 2.72-2.78 (m, 2H); 3.14-3.21 (m, 2H); 4.21-4.23 (m, 1H, J=1); 4.35-4.36 (m, 1H, J=2); 4.64-4.68 (m, 2H, J=5.5, J=8); 6.08-6.11 (d, 1H, J=6.3); 7.45 (m, 1H); 7.74-7.84 (dd, 4H, J=8); 8.44-8.48 (m, 1H, J=8); 8.73 (s, 1H); 8.85 (s, 1H); 11.96 (bs, 1H). Satisfactory elemental analysis for $C_{21}H_{26}N_8O_7S$.

Example 73

1-Deoxy-1-[6-[[[[4-[N-(adamantan-1-yl)sulfonyl]phenyl]amino]carbonyl]-amino]-9H-purin-9-yl]-N-ethyl-β-D-ribofuranuronamide—compound 93

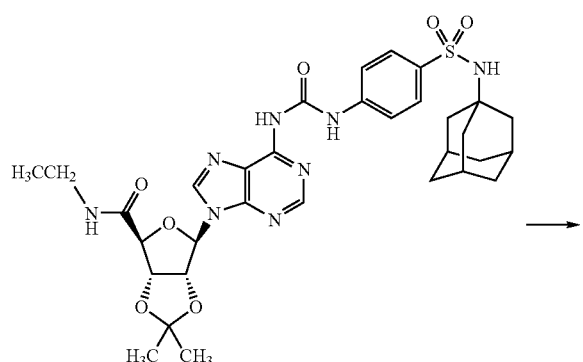

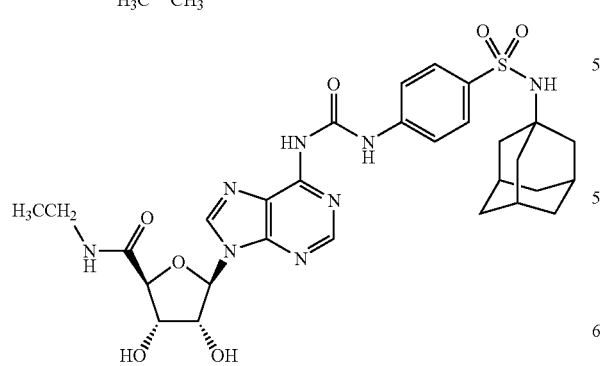

From Example 56: 97.5% yield; gray solid. m.p. 192° C. $^1$H NMR (DMSO-d$_6$): δ 1.01-1.12 (m, 3H); 1.49-1.56 (m, 7H); 1.68 (m, 6H); 1.91-1.98 (m, 1H); 4.2 (bs, 1H); 4.35 (m, 1H); 4.65 (m, 1H); 5.6-5.9 (m, 2H); 6.06 (m, 1H); 7.4 (m, 1H); 7.80 (m, 4H); 8.6 (m, 1H); 8.69 (m, 2H); 10.30 (bs, 1H); 12.04 (bs, 1H). Satisfactory elemental analysis for $C_{29}H_{37}N_8O_7S$.

Example 74

1-Deoxy-1-[6-[[[[4-[N,N-bis(2-chloroethyl)aminosulfonyl]phenyl]-amino]carbonyl]amino]-9H-purin-9-yl]-N-ethyl-β-D-ribofuranuronamide—compound 91

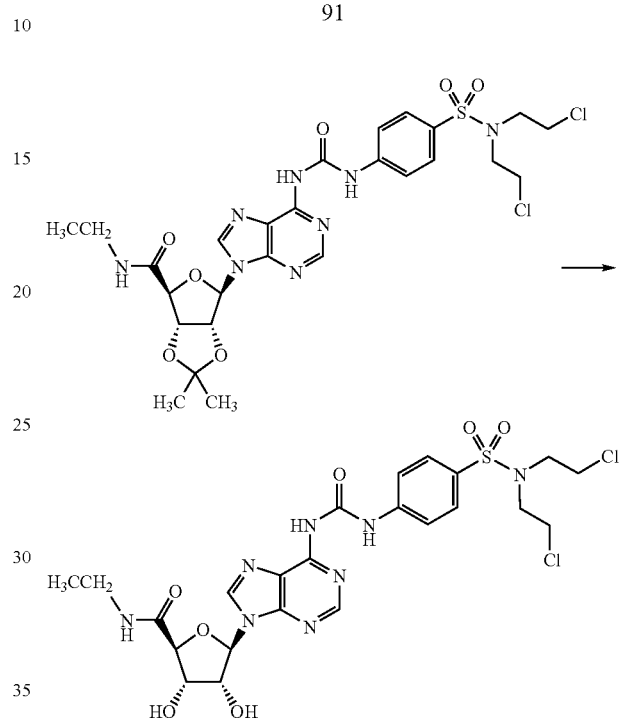

From Example 57: 99% yield; gray solid. m.p. 189° C. $^1$H NMR (DMSO-d$_6$): δ 1.10 (m, 3H); 3.20 (m, 2H); 3.4-3.6 (m, 4H); 3.7-3.8 (m, 4H); 4.2-4.2 (bs, 1H); 4.3-4.4 (s, 1H); 4.6-4.7 (m, 1H); 5.7-5.8 (m, 2H); 6.1-6.3 (m, 1H); 7.8-7.9 (m, 4H); 8.5 (m, 1H); 8.72 (s, 2H); 8.81 (s, 1H). Satisfactory elemental analysis for $C_{28}H_{23}N_8O_7Cl_2S$.

Example 75

1-Deoxy-1-[6-[[[(4-(N-methyl-N-isopropyl-aminosulfonyl)-phenyl)-amino]carbonyl]amino]-9H-purin-9-yl]-N-ethyl-β-D-ribofuranuronamide—compound 97

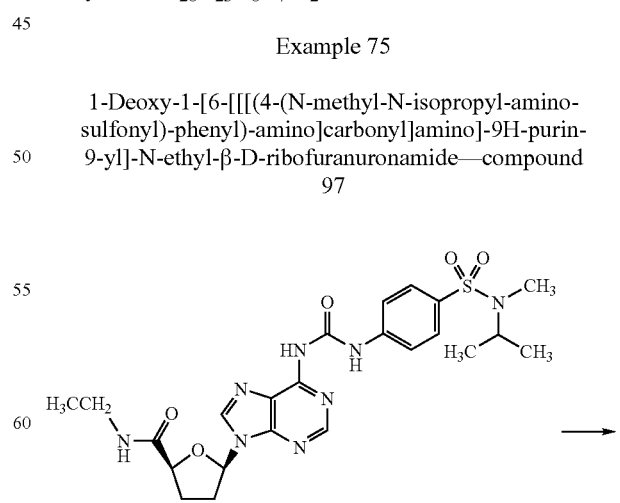

-continued

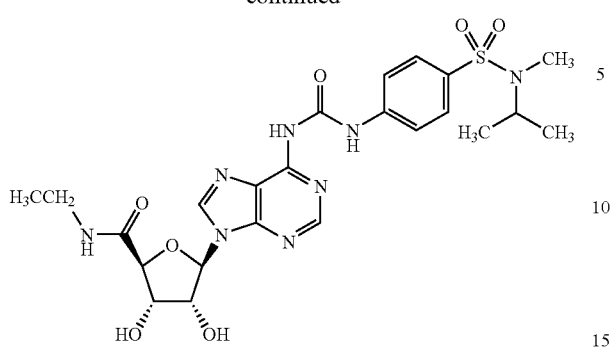

Yield 96%; white solid; mp 140° C.; $^1$H NMR (DMSO-$d_6$): δ 0.86 (d, 6H, J=7); 1.08 (t, 3H, J=7); 2.62 (s, 3H); 3.16 (bs, 1H); 3.22-3.24 (m, 3H); 4.02-4.08 (m, 2H); 4.2 (d, 1H, J=4); 4.35 (bs, 1H); 4.67 (t, 1H, J=6); 6.06 (d, 1H, J=7); 7.72 (d, 2H, J=8); 7.86 (d, 2H, J=8); 8.64 (s, 1H); 8.69 (s, 1H); 10.04 (bs, 1H); 12.02 (bs, 1H). Satisfactory elemental analysis for $C_{23}H_{30}N_8O_7S$.

Example 76

1-Deoxy-1-[6-[[[((4-(N,N-dimethyl-amino-sulfonyl) phenyl)-amino]carbonyl]amino]-9H-purin-9-yl]-N-ethyl-β-D-ribofuranuronamide—compound 98

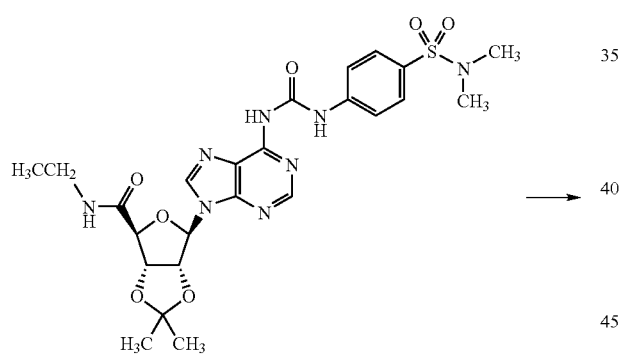

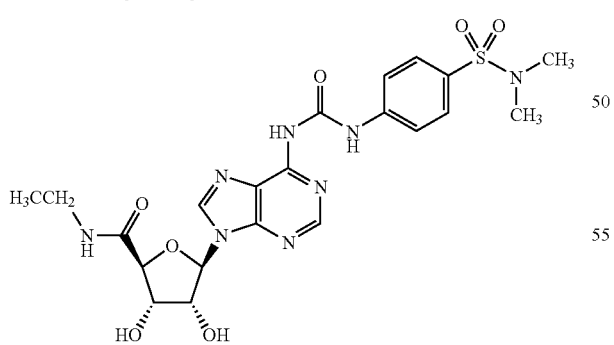

Yield 94%; white solid; mp 176° C.; $^1$H NMR (DMSO-$d_6$) δ 1.08 (t, 3H, J=7); 2.69 (s, 3H); 2.71 (s, 3H); 3.16-3.23 (m, 2H); 3.55 (bs, 1H); 3.84-3.86 (m, 2H); 4.19-4.21 (m, 1H); 4.35 (bs, 1H); 4.64 (t, 1H, J=6); 6.08 (d, 1H, J=6); 7.75-7.83 (m, 4H); 8.74 (s, 1H); 8.82 (s, 1H); 11.98 (bs, 1H); 12.04 (bs, 1H). Satisfactory elemental analysis for $C_{21}H_{26}N_8O_7S$.

Example 77

1-Deoxy-1-[6-[[[(4-(N,N-bis-allyl-amino-sulfonyl)-phenyl)-amino]carbonyl]amino]-9H-purin-9-yl]-N-ethyl-β-D-ribofuranuronamide—compound 99

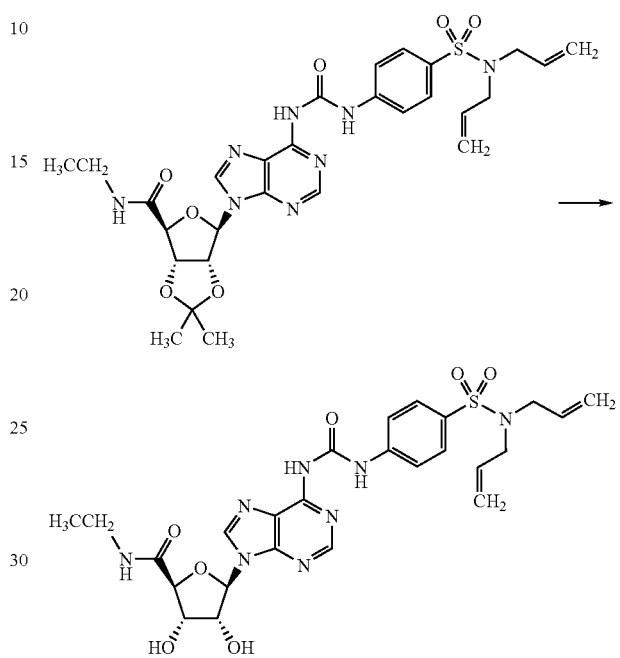

Yield 96%; white solid; mp 126° C.; $^1$H NMR (DMSO-$d_6$): δ 1.08 (t, 3H, J=7); 3.17-3.27 (m, 2H); 3.73 (d, 4H, J=6); 4.22 (bs, 1H); 4.35 (d, 1H, J=2); 4.55-4.68 (m, 1H); 5.12-5.21 (m, 4H); 5.52-5.68 (m, 4H); 6.09 (d, 1H, J=6); 6.8 (d, 2H, J=8); 7.86 (d, 2H, J=8); 8.48 (t, 1H, J=6); 8.74 (s, 1H); 8.81 (s, 1H); 10.54 (bs, 1H); 12.1 (bs, 1H). Satisfactory elemental analysis for $C_{25}H_{30}N_8O_7S$.

Example 78

1-Deoxy-1-[6-[[[(4-(N,N-bis-ethyl-amino-sulfonyl)-phenyl)-amino]carbonyl]amino]-9H-purin-9-yl]-N-ethyl-β-D-ribofuranuronamide—compound 100

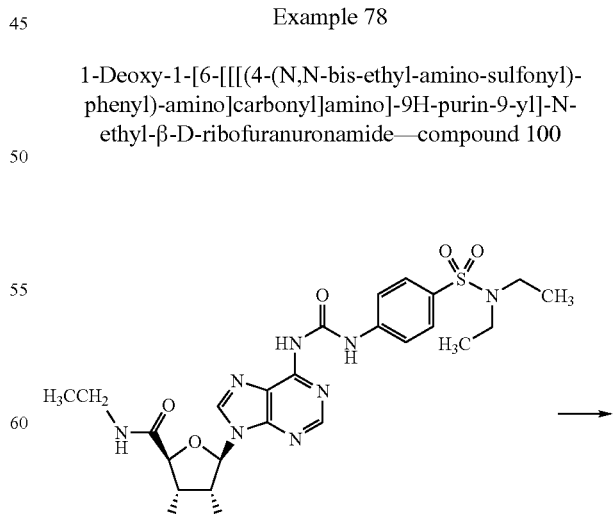

-continued

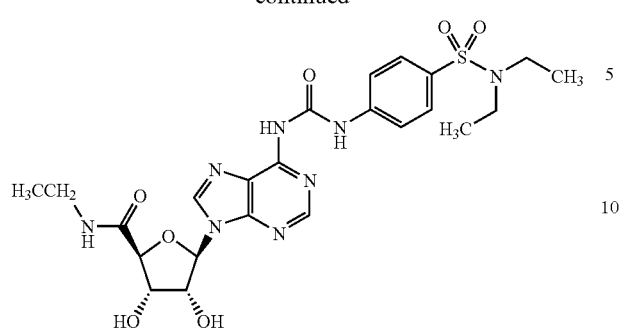

Yield 97%; white solid; mp 168° C.; $^1$H NMR (DMSO-$d_6$): δ 0.99-1.12 (m, 9H); 3.09-3.19 (m, 7H); 3.56 (bs, 1H); 4.19-4.21 (m, 1H); 4.34 (s, 1H); 4.66 (t, 1H, J=6); 5.92 (bs, 1H); 6.07 (d, 1H, J=6); 7.73 (d, 2H, J=8); 7.84 (d, 2H, J=8); 8.65 (s, 1H); 8.71 (s, 1H); 10.56 (bs, 1H); 11.97 (bs, 1H). Satisfactory elemental analysis for $C_{23}H_{30}N_8O_7S$.

Example 79

1-Deoxy-1-[6-[[[(4-(1-cyclopenten-3-yl)-amino-sulfonyl)-phenyl)-amino]carbonyl]amino]-9H-purin-9-yl]-N-ethyl-β-D-ribofuranuronamide—compound 101

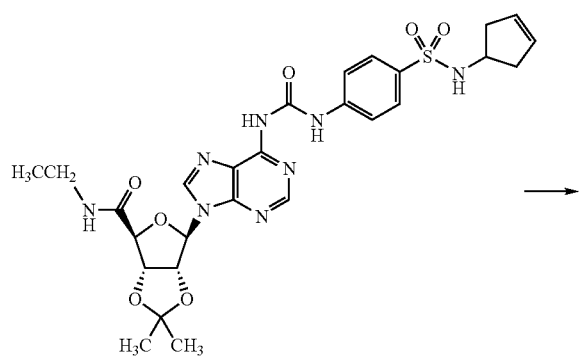

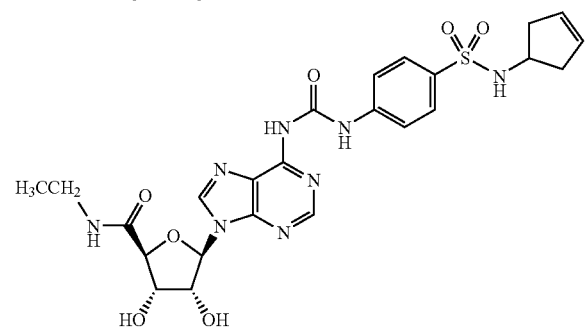

Yield 92%; pale yellow solid; mp 178° C.; $^1$H NMR (DMSO-$d_6$): δ 1.08 (t, 3H, J=7); 1.62-1.64 (m, 1H); 3.13-3.18 (m, 3H); 3.57 (bs, 1H); 3.99-4.02 (m, 4H); 4.19-4.22 (m, 1H); 4.35 (bs, 1H); 4.68 (t, 1H, J=6); 5.71 (bs, 2H); 6.09 (d, 1H, J=6); 7.8-7.85 (m, 4H); 8.7 (s, 1H); 8.77 (s, 1H); 10.45 (bs, 1H); 12.02 (bs, 1H). Satisfactory elemental analysis for $C_{24}H_{28}N_8O_7S$.

Example 80

1-Deoxy-1-[6-[[[(4-(N,N-bis-propyl)-amino-sulfonyl)-phenyl)-amino]carbonyl]amino]-9H-purin-9-yl]-N-ethyl-β-D-ribofuranuronamide—Compound 102

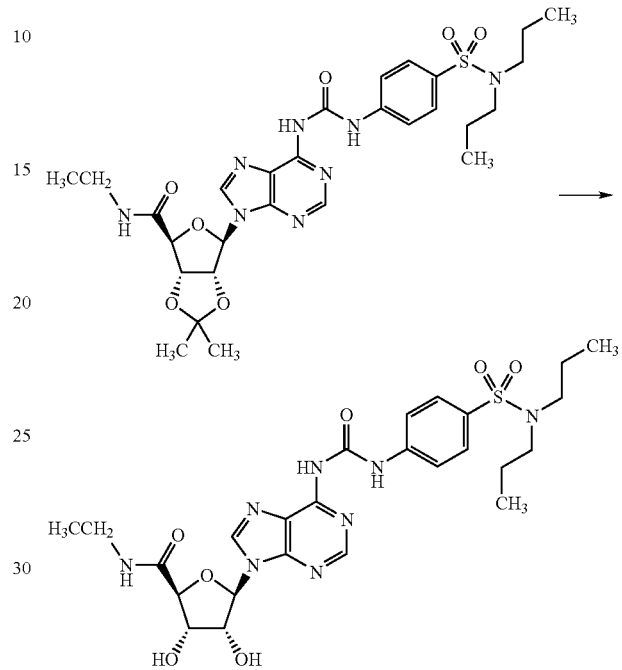

Yield 97%; white solid; mp 159° C.; $^1$H NMR (DMSO-$d_6$): δ 0.81 (t, 6H, J=7); 1.08 (t, 3H, J=7); 1.44-1.52 (m, 4H); 3.01 (t, 4H, J=7); 3.18-3.21 (m, 2H); 3.56 (bs, 1H); 4.21-4.23 (m, 1H); 4.36 (bs, 1H); 4.67 (t, 1H, J=6); 6.1 (d, 1H, J=6); 7.65-7.67 (m, 1H); 7.75-7.82 (m, 4H); 8.47 (bs 1H); 8.74 (s, 1H); 8.85 (s, 1H); 9.87 (bs, 1H); 12.01 (bs, 1H). Satisfactory elemental analysis for $C_{24}H_{28}N_8O_7S$. These examples are intended as preferred embodiments only, and are provided to further illustrate this invention. They are not intended, either individually or collectively, to define the full scope of the invention.

Example 81

Synthesis of 2',3'-O-Isopropylideneadenosine-5'-uronic acid

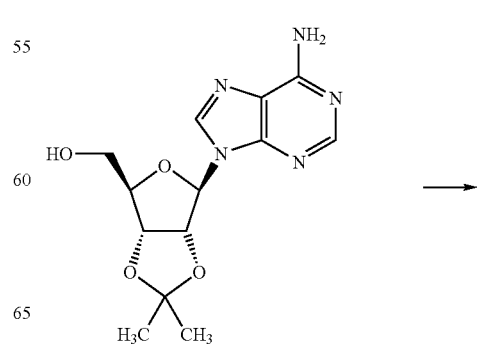

-continued

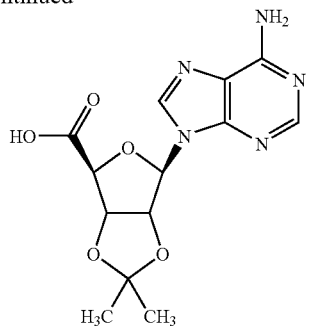

Iodobenzene diacetate (11.5 g, 0.0358 mol), TEMPO (0.512 g, 0.0032 mol), and 2',3'-O-isopropylideneadenosine (Example 1, 5 g, 0.0162 mol) were combined in a 100 mL round bottom flask. To this mixture was added 50 mL of a 1:1 acetonitrile-water solution. The reaction mixture was stirred for 2.5 h at room temperature. The resulting precipitate was filtered, triturated sequentially with diethyl ether and acetone, and dried in vacuo to afford the desired product as a white solid 4.97 g, 95%. $^1$H-NMR (DMSO-$d_6$): δ 1.35 (s, 3H); 1.52 (s, 3H); 4.68 (d, 1H, J=1 Hz); 5.46 (d, 1H, J=6.0 Hz); 5.52 (dd, 1H, J=6.0 Hz); 6.32 (s, 1H); 7.25 (s, 2H, NH$_2$); 8.08 (s, 1H); 8.24 (s, 1H).

Example 82

Synthesis of 2',3'-O-Isopropylideneadenosine-5'-N-ethyluronamide

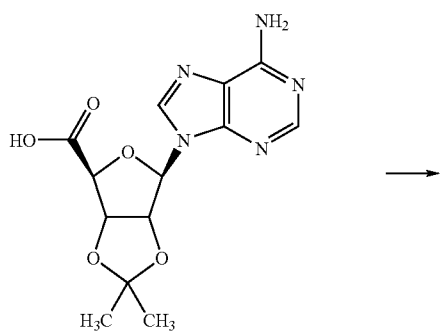

Polystyrene-carbodiimide resin (41 g, 50 mmol, 1.2 mmol/g) and polystyrene-dimethylaminopyridine (40 g, 60 mmol, and 1.6 mmol/g) were added to a dry reaction vessel containing 400 mL of a 1:1 mixture of dichloromethane and THF. The 2',3'-O-isopropylideneadenosine-5'uronic acid (Example 81, 8.4 g, 26 mmol) was added to the above mixture and stirred for 10 min. Ethyl amine HCl (4.22 g, 52 mmol) was added and the mixture was stirred at room temperature overnight to afford the crude uronamide product. The resins were removed by filtration and washed with dichloromethaneand ethyl acetate. The product was purified by flash chromatography with 8:1.5:0.5 (ethyl acetate:dichloromethane:methanol). Yield: 6.5 g, 72% $^1$H-NMR (CDCl$_3$): δ 0.85-0.90 (t, 3H, J=8 Hz); 1.39 (s, 3H); 1.63 (s, 3H); 3.07-3.13 (m, 2H); 4.70 (s, 1H); 5.39-5.40 (m, 2H); 5.70 (bs, 2H); 6.06 (s, 1H); 6.85 (bs, 1H); 7.86 (s, 1H); 8.31 (s, 1H).

Example 83

Synthesis of Phenoxycarbonyltetrazole

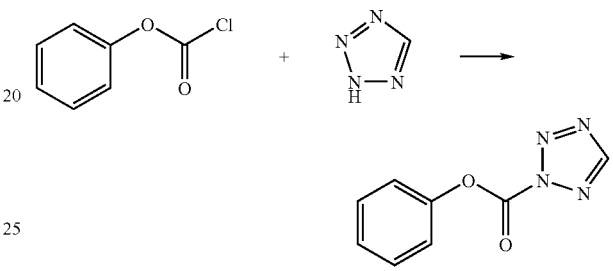

The title compound was prepared according to the procedure described in *Tetrahedron Letters*, 1977, 1935. Accordingly, phenylchloroformate (6.73 g, 43 mmol) was added dropwise into a solution of tetrazole (42.84 mmol, 3 wt % in 100 mL acetonitrile) containing triethylamine (4.35 g, 43 mmol) at 0° C. The mixture was stirred for 15 minutes and the solvent was removed without heating at reduced pressure. Ethyl acetate (80 mL) was added to the white solid and passed through a plug of silica gel, eluting with 3% triethylamine in ethyl acetate to afford phenoxycarbonyltetrazole in 85% yield (6.9 g). $^1$H-NMR (CDCl$_3$): δ 7.34-7.54 (m, 5H); 9.34 (s, 1H).

Example 84

Synthesis of 2',3'-O-isopropylidene-$N^6$-(phenyloxycarbonyl)-adenosine-5'-ethyluronamide

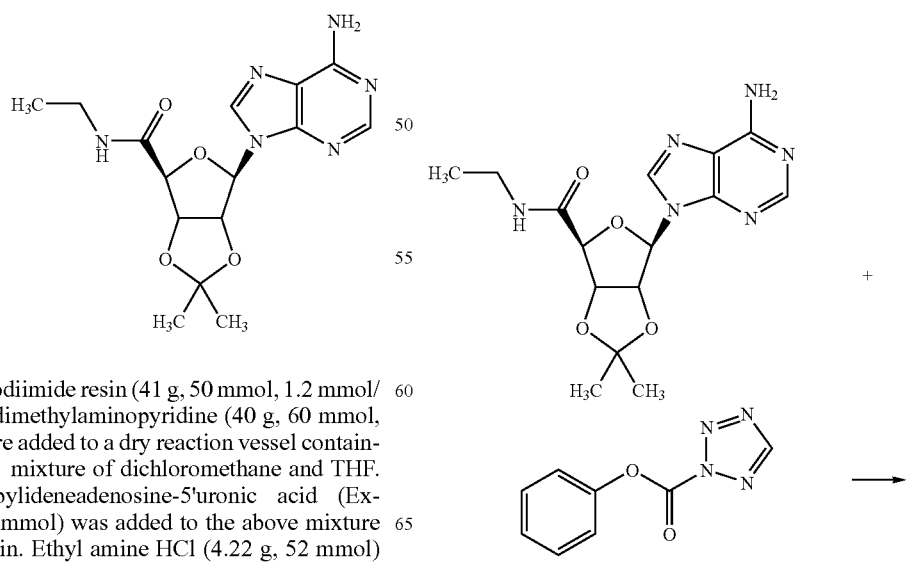

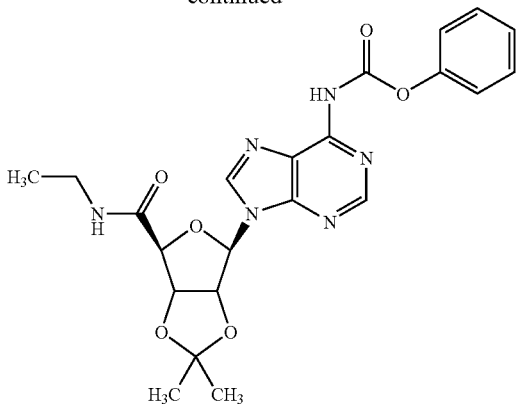

2',3'-O-Isopropylideneadenosine-5'-ethyluronamide (Example 82, 2.62 g, 7.5 mmol) and phenoxycarbonyltetrazole (Example 83, 4.28 g. 22.5 mmol) were added to anhydrous THF (50 mL) and heated at 39° C. for 6 h (TLC, ethyl acetate/dichloromethane/methanol=80/15/5). The solvent was removed at reduced pressure, keeping the temperature at room temperature. The crude product was purified by flash chromatography with 80:15:5 (ethyl acetate:dichloromethane:methanol) to afford the desired product as a white solid (2.78 g, 79%). m.p. 118-120° C. LC/MS: m/z 469.4 $[C_{22}H_{24}N_6O_6+H]^+$ $^1$H-NMR (acetone-$d_6$): δ 0.64-0.70 (m, 3H,); 1.39 (s, 3H); 1.57 (s, 3H); 2.87-2.91 (m, 2H); 4.62 (d, 1H, J=1.8 Hz); 5.57-5.58 (m, 2H); 6.45 (s, 1H); 7.05 (bs, 1H); 7.30 (m, 3H); 7.44 (m, 2H); 8.48 (d, 1H, J=2.6 Hz); 8.61 (d, 1H, J=2.8 Hz); 9.19 (bs, 1H).

Example 85

Synthesis of N-(isopropyl)-N-(methyl)-2-nitrobenzenesulfonamide

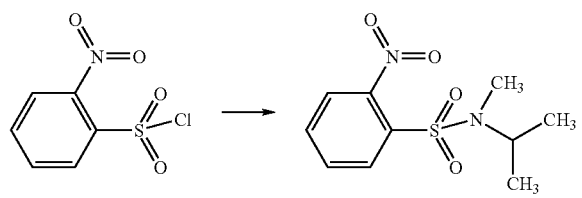

A 250 mL round bottom flask was equipped with a magnetic stirrer. The flask was charged with isopropylmethylamine (0.85 g, 11.6 mmol) followed by THF (50 mL). The mixture was cooled to 0° C. by placing the flask in an ice bath. Potassium hydroxide (23.2 mmol) was dissolved in water (20 mL) and added to the flask. An addition funnel was installed and charged with 2-nitrobenzenesulfonyl chloride (11.6 mmol) in THF (40 mL). The solution was added dropwise over 20 minutes, then the ice bath was removed. TLC (dichloromethane) indicated that the reaction was complete after addition of the 2-nitro-benzenesulfonyl chloride. The reaction was concentrated under diminished pressure, water (100 mL) was added, the mixture extracted with ethyl acetate (150 mL), dried ($Na_2SO_4$), and filtered. The solvent was removed under reduced pressure. The residue was dissolved in dichloromethane (20 mL) and loaded onto a plug of silica gel (400 g in a 600 mL sintered glass funnel), and eluted with dichloromethane. Fractions were taken (100 mL) until the product eluted, as determined by TLC. Fractions containing the product were collected, and the solvent was removed in vacuo to yield N-(isopropyl)-N-(methyl)-2-nitrobenzenesulfonamide as a pale yellow oil. 3.08 g, (88%). $^1$H-NMR (CDCl$_3$): δ 1.12-1.14 (d, 6H, J=6.7 Hz); 2.81 (s, 3H); 4.18-4.24 (m, 1H, J=6.7 Hz); 7.61-7.69 (m, 3H); 8.03-8.06 (m, 1H).

In a similar manner, the following sulfonamides were prepared:

Example 86

N-(Pentyl)-2-nitrobenzenesulfonamide

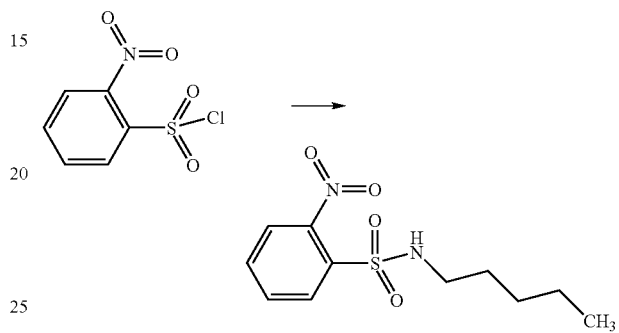

3.02 g, (81%), pale yellow crystalline solid. $^1$H-NMR (CDCl$_3$): δ 0.82-0.87 (m, 3H); 1.24-1.30 (m, 4H); 1.48-1.55 (m, 2H); 3.06-3.13 (q, 2H, J=6.8 Hz); 5.22-5.26 (b, 1H); 7.73-7.77 (m, 2H); 7.85-7.88 (m, 1H); 8.13-8.16 (m, 1H).

Example 87

N-(2-Nitrobenzenesulfonyl)-2,5-dihydro-1H-pyrrole

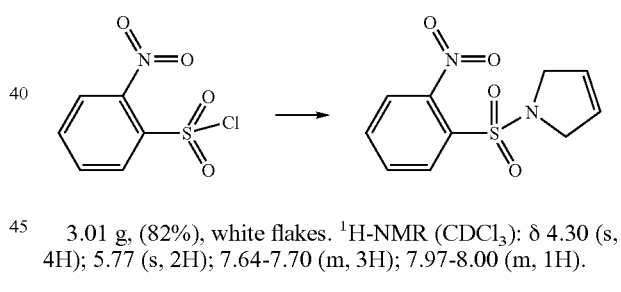

3.01 g, (82%), white flakes. $^1$H-NMR (CDCl$_3$): δ 4.30 (s, 4H); 5.77 (s, 2H); 7.64-7.70 (m, 3H); 7.97-8.00 (m, 1H).

Example 88

N-(Adamantan-1-yl)-2-nitrobenzenesulfonamide

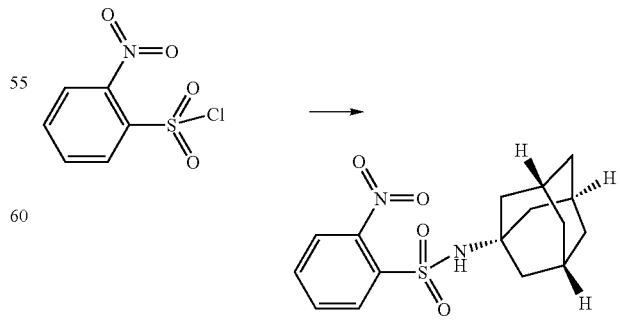

770 mg, (38%), pale yellow crystalline solid. $^1$H-NMR (CDCl$_3$): δ 1.61-1.67 (m, 6H); 1.88-1.89 (s, 6H); 2.05 (bs, 3H); 5.17 (bs, 1H); 7.69-7.74 (m, 2H); 7.82-7.86 (d, 1H, J=7.3 Hz); 8.20-8.23 (d, 1H, J=7.3 Hz).

Example 89

Synthesis of N-(4-methoxyphenyl)-2-nitrobenzenesulfonamide

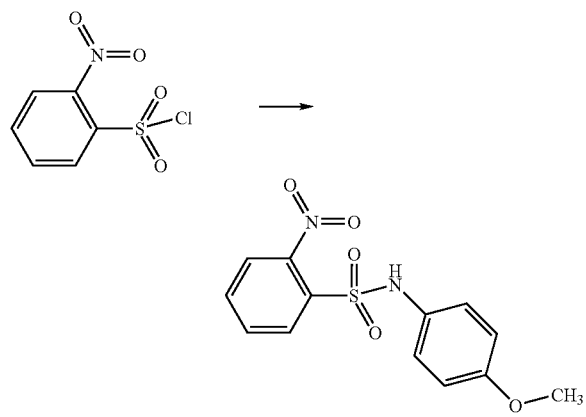

A 250 mL round bottom flask was equipped with a magnetic stirrer, charged with p-anisidine (13.0 mmol), followed by dichloromethane (75 mL). The flask was then placed in an ice bath to chill the contents. Triethylamine was added and an addition funnel was installed. The addition funnel was charged with 2-nitrobenzenesulfonyl chloride (32.4 mmol) in dichloromethane (75 mL). The sulfonyl chloride was added dropwise very slowly and the reaction monitored by TLC (dichloromethane/silica) several times during the addition. The reaction was complete after addition of 50 mL (21.6 mmol) of the sulfonyl chloride solution. The reaction solvent was removed at 0° C. and immediately loaded onto a 600 mL sintered glass funnel charged with silica gel (400 g), eluted with dichloromethane collecting 100 mL fractions. Fractions containing the desired product were combined and evaporated under diminished pressure to yield the title compound as a yellow powder in excellent yield. 3.67 g, (92%). $^1$H-NMR (CDCl$_3$): δ 3.20 (s, 3H); 6.78-6.79 (d, 2H, J=8.9 Hz); 7.07-7.10 (d, 3H, J=8.9 Hz); 7.53-7.58 (t, 1H, J=7.7 Hz); 7.66-7.71 (t, 1H, J=7.8 Hz); 7.73-7.76 (d, 1H, J=7.8 Hz); 7.84-7.87 (d, 1H, J=7.9 Hz).

Example 90

Synthesis of N-(isopropyl)-N-(methyl)-3-nitrobenzenesulfonamide

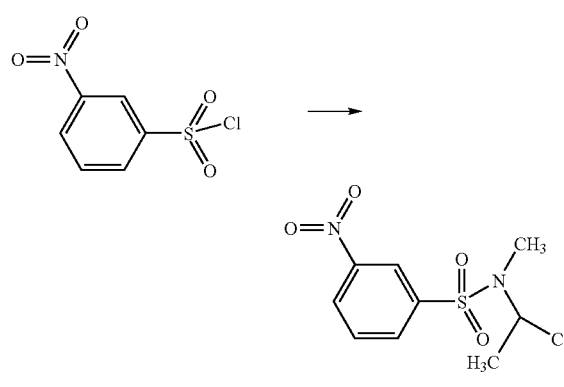

A 250 mL round bottom flask was equipped with a magnetic stirrer. The flask was charged with isopropylmethylamine (0.85 g, 11.6 mmol) followed by THF (50 mL). The mixture was cooled to 0° C. by placing the flask in an ice bath. Potassium hydroxide (23.2 mmol) was dissolved in water (20 mL) and added to the flask. An addition funnel was installed and charged with 3-nitrobenzenesulfonyl chloride (11.6 mmol) in THF (40 mL). The solution was added dropwise over 20 minutes, then the ice bath was removed. TLC (dichloromethane) indicated that the reaction was complete after addition of the 2-nitrobenzenesulfonyl chloride. The reaction was concentrated under diminished pressure, water (100 mL) was added, the mixture extracted with ethyl acetate (150 mL), dried (Na$_2$SO$_4$), and filtered. The solvent was removed under reduced pressure. The residue was dissolved in dichloromethane (20 mL) and loaded onto a plug of silica gel (400 g in a 600 mL sintered glass funnel), and eluted with dichloromethane. Fractions were taken (100 mL) until the product eluted, as determined by TLC. Fractions containing the product were collected, and the solvent was removed in vacuo to yield N-(isopropyl)-N-(methyl)-3-nitrobenzenesulfonamide as a pale yellow, crystalline solid. 2.38 g, (79%). $^1$H-NMR (CDCl$_3$): δ 1.03-1.05 (d, 6H, J=6.7 Hz); 2.78 (s, 3H); 4.23-4.32 (m, 1H, J=6.7 Hz); 7.70-7.76 (t, 1H, J=8.0 Hz); 8.13-8.15 (d, 1H, J=6.8 Hz); 8.40-8.43 (d, 1H, J=8.2 Hz); 8.64 (s, 1H).

In a similar manner, the following compounds were prepared:

Example 91

N-(Pentyl)-3-nitrobenzenesulfonamide

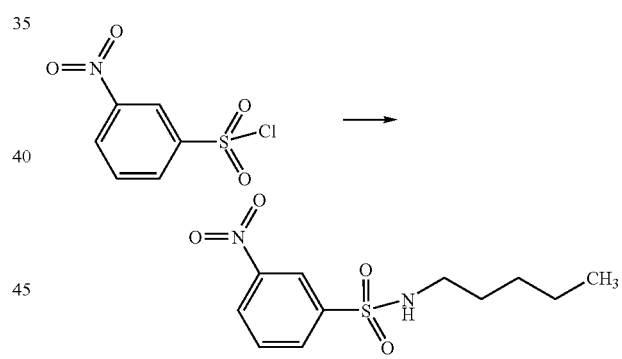

1.56 g, (52%), white crystalline solid. $^1$H-NMR (CDCl$_3$): δ 0.83-0.87 (t, 3H, J=6.7 Hz); 1.23-1.28 (m, 4H); 1.48-1.52 (m, 2H); 2.99-3.06 (q, 2H, J=6.8 Hz); 4.72 (b, 1H); 7.73-7.78 (t, 1H, 8.1 Hz); 8.20-8.22 (d, 1H, J=7.8 Hz); 8.42-8.45 (d, 1H, J=8.2 Hz); 8.71 (s, 1H).

Example 92

N-(3-Nitrobenzenesulfonyl)-2,5-dihydro-1H-pyrrole

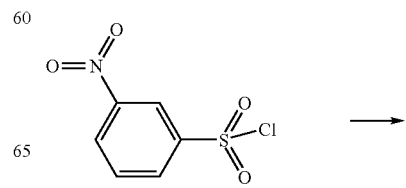

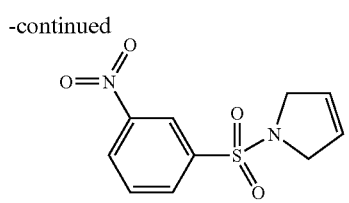

2.78 g, (76%), white crystalline solid. ¹H-NMR (CDCl₃): δ 4.19 (s, 4H); 5.71 (s, 2H); 7.74-7.79 (t, 1H, J=8.0 Hz); 8.15-8.19 (d, 1H, J=7.8 Hz); 8.43-8.47 (d, 1H, J=9.5 Hz); 8.67-8.68 (s, 1H).

Example 93

N-(Adamantan-1-yl)-3-nitrobenzenesulfonamide

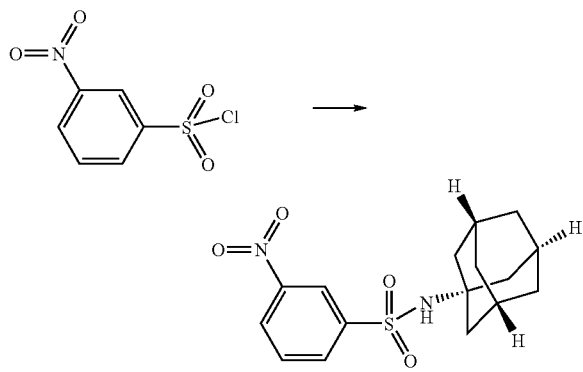

1.09 g, (36%), white flakes. ¹H-NMR (CDCl₃): δ 1.59-1.61 (m, 6H); 1.81-1.82 (m, 6H); 2.04 (bs, 3H); 4.58 (bs, 1H); 7.68-7.74 (t, 1H, J=8.0 Hz); 8.22-8.24 (d, 1H, J=7.2 Hz); 8.38-8.41 (d, 1H, J=8.8 Hz); 8.74-8.75 (s, 1H).

Example 94

Synthesis of
N-(4-methoxyphenyl)-3-nitrobenzenesulfonamide

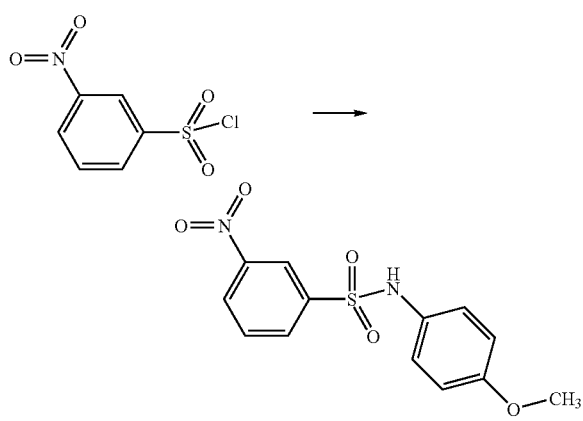

A 250 mL round bottom flask was equipped with a magnetic stirrer. The flask was charged with p-anisidine (13.0 mmol) followed by dichloromethane (50 mL). Triethylamine (25.9 mmol) was added followed by 3-nitrobenzenesulfonyl chloride (16.2 mmol). Additional dichloromethane (75 mL) was added for solubility. The reaction was allowed to stir overnight. After 18 hours, TLC (dichloromethane/silica) indicated that the reaction was not complete. One additional equivalent of 3-nitrobenzenesulfonyl chloride (13.0 mmol), and two equivalents of triethylamine (25.9 mmol) were added to the reaction. After 10 minutes, TLC indicated that two products had formed and all starting anisidine was consumed. The reaction was washed with 2N HCl (100 mL), dried (Na₂SO₄), filtered, and the solvent removed under diminished pressure. The residue was dissolved in dichloromethane (20 mL) and loaded onto a 600 mL sintered glass funnel charged with silica gel (400 g). The silica plug was eluted with dichloromethane (100 mL fractions) until the first product eluted from the filter column (TLC, dichloromethane/silica). The solvent system was changed to 9:1 dichloromethane/ethyl acetate and fractions were taken (100 mL) until the second product eluted from the filter column. The solvent from both samples was removed under reduced pressure to yield a mixture of the undesired N,N-bis-(4-methoxyphenyl)-3-nitrobenzenesulfonamide and the desired product.

N-(4-methoxyphenyl)-3-nitrobenzenesulfonamide: 1.61 g, (40%), tan powder. ¹H-NMR (CDCl₃): δ 3.77 (s, 3H); 6.47 (s, 1H); 6.78-6.81 (d, 2H, J=6.8 Hz); 6.97-7.00 (d, 2H, J=6.7 Hz); 7.62-7.67 (t, 1H, J=8.1 Hz); 7.96-7.98 (d, 1H, J=7.3 Hz); 8.38-8.41 (d, 1H, J=8.2 Hz); 8.58 (s, 1H).

N,N-bis-(4-methoxyphenyl)-3-nitrobenzenesulfonamide: 3.0 g, (56%), white powder.
¹H-NMR (CDCl₃): δ 3.86 (s, 3H); 6.93-6.94 (d, 4H, J=3.6 Hz); 7.81-7.86 (t, 2H, J=8.1 Hz); 8.32-8.35 (d, 2H, J=7.9 Hz); 8.55-8.58 (d, 2H, J=8.3 Hz); 8.73-8.74 (s, 2H).

The N,N-bis-(4-methoxyphenyl)-3-nitrobenzenesulfonamide could be hydrolyzed to the desired N-(4-methoxyphenyl)-3-nitrobenzenesulfonamide as follows: A 1 L round bottom flask was equipped with a magnetic stirrer. The flask was charged with N,N-bis-(4-methoxyphenyl)-3-nitrobenzenesulfonamide (7.25 mmol), followed by 1:1 methanol/dichloromethane (400 mL). 10N NaOH (150 mL) was added to the flask and the mixture allowed to stir. After 2 hours, TLC (dichloromethane/silica) indicated that the reaction was complete. The reaction was acidified with concentrated HCl and extracted with dichloromethane (300 mL), dried (Na₂SO₄), filtered, and the solvent removed under reduced pressure to yield the title compound.

Example 95

Synthesis of
N-(isopropyl)-N-(methyl)-2-aminobenzenesulfonamide

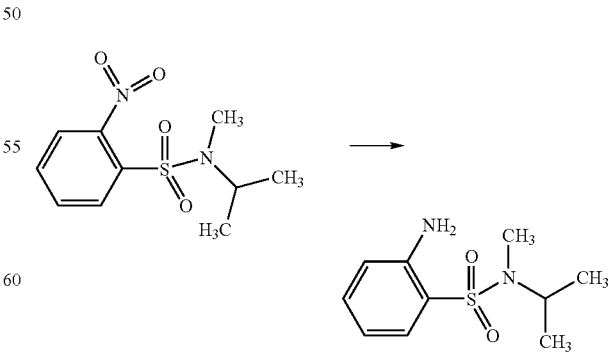

A 250 mL round bottom flask was equipped with a magnetic stirrer and an ice bath. The flask was charged with N-isopropyl-N-methyl-2-nitrobenzenesulfonamide (9.21 mmol), followed by methanol (100 mL). The solution was cooled to 0° C. Hydrazine monohydrate (92.1 mmol) was added, followed by Raney nickel (catalytic amount). After 5 hours TLC (9:1 dichloromethane/ethyl acetate) indicated that the reaction was complete. The reaction was filtered through celite and the catalyst recovered to a separate waste stream. The methanol was removed under reduced pressure and water (100 mL) added. The aqueous solution was extracted with ethyl acetate (100 mL), dried ($Na_2SO_4$), filtered, and the solvent removed under vacuum. The resultant yellow oil was purified by silica gel chromatography (1.5" millimeter×18" length, 9:1 dichloromethane/ethyl acetate). Fractions containing the desired product were combined and the solvent removed under vacuum to yield N-(isopropyl)-N-(methyl)-2-amino benzene sulfonamide as a clear yellow oil. 2.21 g, (81%). LC/MS: m/z 229.4 $[C_{10}H_{16}N_2O_2S+H]^+$. $^1$H-NMR (CDCl$_3$): δ 1.04-1.06 (d, 6H, J=6.7 Hz); 2.73 (s, 3H); 4.15-4.24 (m, 1H, J=6.7 Hz); 4.95 (b, 2H); 6.68-6.78 (m, 2H); 7.24-7.29 (t, 1H, J=7.7 Hz); 7.62-7.65 (d, 1H, J=8.0 Hz)

In a similar manner, the following compounds were prepared:

Example 96

N-(Pentyl)-2-aminobenzenesulfonamide

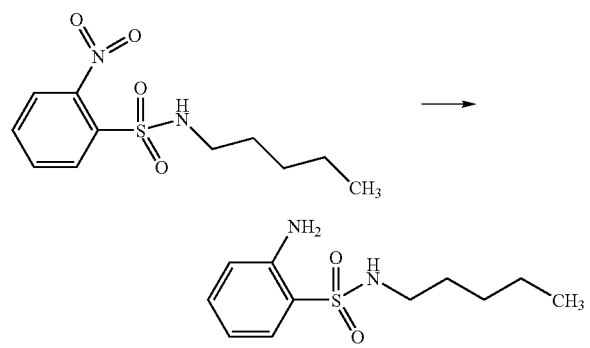

1.76 g, (65%), clear oil. LC/MS: m/z 243.2 $[C_{11}H_{18}N_2O_2S+H]^+$. $^1$H-NMR (CDCl$_3$): δ 0.81-0.85 (t, 3H, J=6.6 Hz); 1.19-1.26 (m, 4H); 1.39-1.46 (m, 2H, J=6.9 Hz); 2.83-2.90 (q, 2H, J=6.8 Hz); 4.18-5.15 (b, 1H); 4.683 (b, 2H); 6.75-6.84 (m, 2H); 7.30-7.35 (t, 1H, J=7.7 Hz); 7.69-7.72 (d, 1H, J=7.9 Hz).

Example 97

N-(Adamantan-1-yl)-2-aminobenzenesulfonamide

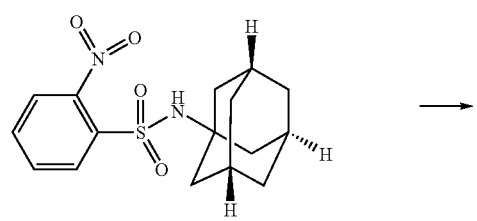

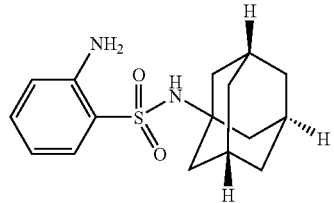

649 mg, (93%), white crystalline solid. m.p.: 136-137° C. LC/MS: m/z 307.2 $[C_{16}H_{22}N_2O_2S+H]^+$. $^1$H-NMR (CDCl$_3$): δ 1.52-1.62 (b, 6H); 1.76-1.77 (m, 6H); 2.00 (bs, 3H); 4.63 (bs, 2H); 6.74-6.76 (d, 1H, J=8.1 Hz); 6.79-6.84 (t, 1H, J=8.0 Hz); 7.28-7.33 (t, 1H, J=7.7 Hz); 7.74-7.77 (d, 1H, J=8.0 Hz).

Example 98

N-(4-Methoxyphenyl)-2-aminobenzenesulfonamide

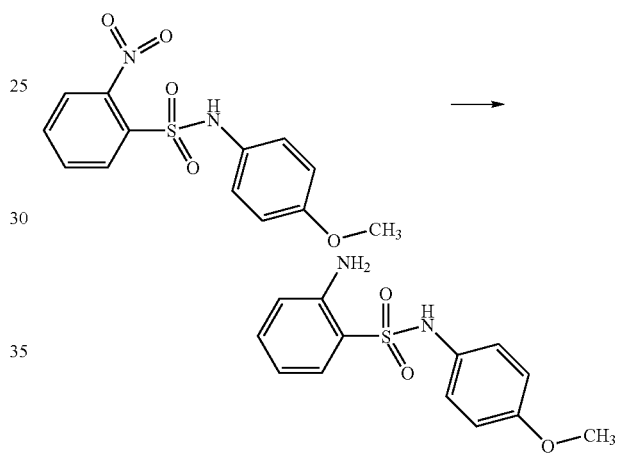

3.71 g, (86%), pale tan crystalline solid. m.p.: 98-99° C. LC/MS: m/z 279.2 $[C_{13}H_{14}N_2O_3S+H]^+$. $^1$H-NMR (CDCl$_3$): δ 3.73 (s, 3H); 4.48 (b, 2H); 6.62 (bs, 1H); 6.64-6.67 (t, 1H, J=7.7 Hz); 6.70-6.73 (d, 2H, J=8.9 Hz); 6.74-6.77 (d, 1H, J=8.1 Hz); 6.92-6.95 (d, 2H, J=8.9 Hz); 7.24-7.30 (t, 1H, J=7.9 Hz); 7.39-7.42 (d, 1H, J=8.0 Hz).

Example 99

N-(isopropyl)-N-(methyl)-3-aminobenzenesulfonamide

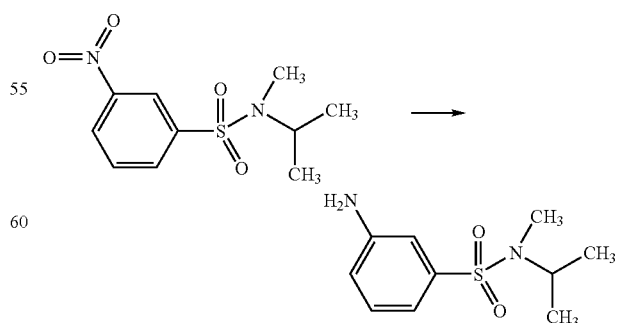

1.28 g, (61%), pale yellow solid. m.p.: 92-93° C. LC/MS: m/z 229.0 $[C_{10}H_{16}N_2O_2S+H]^+$. $^1$H-NMR (CDCl$_3$): δ 0.98-1.00 (d, 6H, J=6.7 Hz); 2.71 (s, 3H); 3.87 (bs, 2H); 4.18-4.22

(m, 1H, J=6.7 Hz); 6.80-6.83 (d, 1H, J=7.9 Hz); 7.10 (s, 1H); 7.14-7.16 (d, 1H, J=7.8 Hz); 7.22-7.28 (t, 1H, J=7.8 Hz).

Example 100

N-(Pentyl)-3-aminobenzenesulfonamide

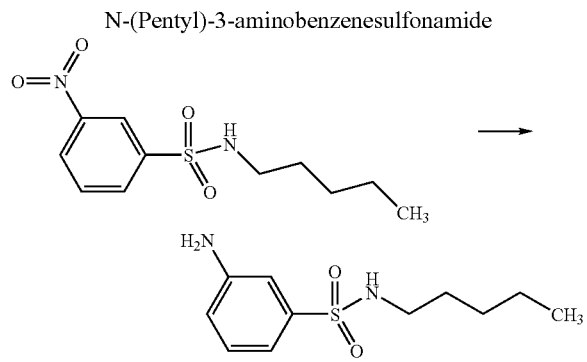

1.64 g, (75%), white crystalline solid. m.p.: 55-56° C. LC/MS: m/z 243.0 [$C_{11}H_{18}N_2O_2S+H$]+. $^1$H-NMR (CDCl$_3$): δ 0.83-0.88 (t, 3H, J=6.7 Hz); 1.26-1.27 (m, 4H); 1.42-1.51 (m, 2H); 2.91-2.98 (q, 2H, J=6.7 Hz); 3.89 (bs, 2H); 4.23-4.27 (bs, 1H); 6.82-6.85 (d, 1H, J=7.8 Hz); 7.14-7.15 (s, 1H); 7.19-7.21 (d, 1H, J=7.9 Hz); 7.25-7.30 (t, 1H, J=7.8 Hz).

Example 101

N-(Adamantan-1-yl)-3-aminobenzenesulfonamide

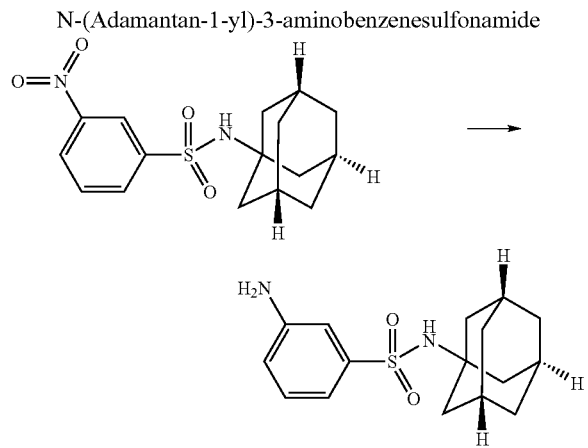

910 mg, (91%), white powder. m.p.: 174-175° C. LC/MS: m/z 307.2 [$C_{16}H_{22}N_2O_2S+H$]+. $^1$H-NMR (CDCl$_3$): δ 1.58-1.59 (m, 6H); 1.80-1.81 (m, 6H); 2.01 (bs, 3H); 3.88 (bs, 2H); 4.43 (bs, 1H); 6.78-6.82 (m, 1H); 7.19-7.20 (m, 1H); 7.24-7.26 (m, 2H).

Example 102

N-(4-Methoxyphenyl)-3-aminobenzenesulfonamide

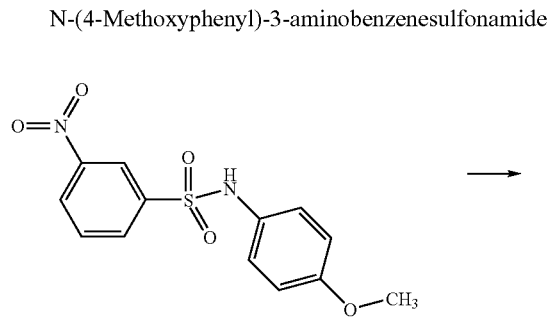

-continued

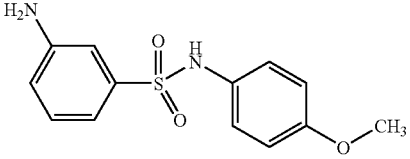

2.48 g, (62%), white crystalline solid. m.p.: 180-181° C. LC/MS: m/z 279.2 [$C_{13}H_{14}N_2O_3S+H$]+. $^1$H-NMR (DMSO-d$_6$): δ 3.67 (s, 3H); 5.51 (s, 2H); 6.67-6.70 (d, 1H, J=8.0 Hz); 6.77-6.80 (m, 3H); 6.89 (s, 1H); 6.96-6.99 (d, 2H, J=8.9 Hz); 7.08-7.14 (t, 1H, 7.9 Hz); 9.72 (s, 1H).

Example 103

Synthesis of 2-(2,5-Dihydropyrrol-1-yl-sulfonyl)-aniline

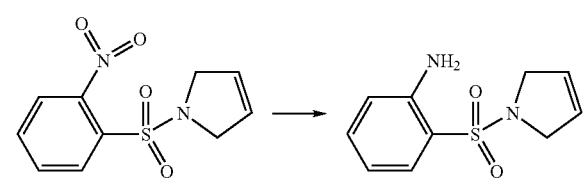

A 250 mL round bottom flask was equipped with a magnetic stirrer and charged with 1-(2-nitrobenzenesulfonyl)-2,5-dihydro-1H-pyrrole (Example 87, 9.32 mmol, followed by 3:1 water/tetrahydrofuran v/v (50 mL). Indium powder (37.3 mmol) was added, followed by concentrated HCl (55.9 mmol). The reaction gives a slight exotherm and the indium forms a solid metal chunk. After 24 hours, TLC (dichloromethane/silica) indicated the reaction was mostly complete. The indium was removed with a pair of tweesers to a separate waste stream and the reaction was neutralized with sodium bicarbonate. The aqueous mixture was extracted with ethyl acetate (150 mL), the organic layer dried (Na2SO4), filtered, and the solvent was removed under reduced pressure. The residue was dissolved in dichloromethane (20 mL) and loaded onto a 600 mL sintered glass funnel charged with silica gel (400 g). The silica plug was eluted with 9:1 dichloromethane:ethyl acetate, collecting 100 mL fractions. Fractions containing the desired product were combined and the solvent was removed under diminished pressure to afford 2-(2,5-dihydropyrrole-1-sulfonyl)-aniline as a pale yellow, crystalline solid. 1.66 g, (62%). m.p.: 104-105° C. LC/MS: m/z 225.2 [$C_{10}H_{12}N_2O_2S+H$]+. $^1$H-NMR (CDCl$_3$): δ 4.20 (s, 4H); 5.05 (b, 2H); 5.69 (s, 2H); 6.71-6.79 (m, 2H); 7.26-7.32 (t, 1H, J=8.1 Hz); 7.64-7.67 (d, 1H, J=7.9 Hz).

Example 104

Synthesis of 3-(2,5-Dihydropyrrol-1-yl-sulfonyl)-aniline

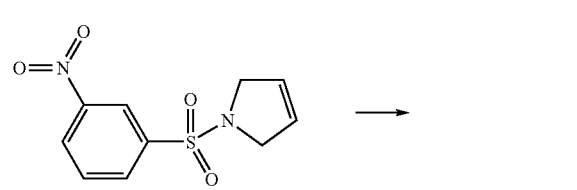

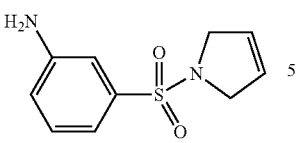

A 250 mL round bottom flask was equipped with a magnetic stirrer and charged with 1-(3-nitrobenzenesulfonyl)-2,5-dihydro-1H-pyrrole (Example 92, 9.32 mmol, followed by 3:1 water/tetrahydrofuran v/v (50 mL). Indium powder (37.3 mmol) was added, followed by concentrated HCl (55.9 mmol). The reaction gives a slight exotherm and the indium forms a solid metal chunk. After 24 hours, TLC (dichloromethane/silica) indicated the reaction was mostly complete. The indium was removed with a pair of tweezers to a separate waste stream and the reaction was neutralized with sodium bicarbonate. The aqueous mixture was extracted with ethyl acetate (150 mL), the organic layer dried ($Na_2SO_4$), filtered, and the solvent was removed under reduced pressure. The residue was dissolved in dichloromethane (20 mL) and loaded onto a 600 mL sintered glass funnel charged with silica gel (400 g). The silica plug was eluted with 9:1 dichloromethane:ethyl acetate, collecting 100 mL fractions. Fractions containing the desired product were combined and the solvent was removed under diminished pressure to afford 3-(2,5-dihydropyrrole-1-sulfonyl)-aniline as a white, crystalline solid. 1.50 g, (72%). m.p.: 187-188° C. LC/MS: m/z 224.8 $[C_{10}H_{12}N_2O_2S+H]^+$. $^1$H-NMR ($CDCl_3$): δ 4.0 (b, 2H); 4.13 (s, 4H); 5.66 (s, 2H); 6.84-6.87 (d, 1H, J=7.9 Hz); 7.13-7.14 (s, 1H); 7.18-7.20 (d, 1H, J=7.7 Hz); 7.26-7.31 (t, 1H, J=7.8 Hz).

Example 105

Synthesis of 1-Deoxy-N-ethyl-2,3-O-(isopropylidene)-1-[[6-[[(2-sulfonamidophenyl)amino]carbonyl]amino]-9H-purin-9-yl]-β-D-ribofuranuron-amide

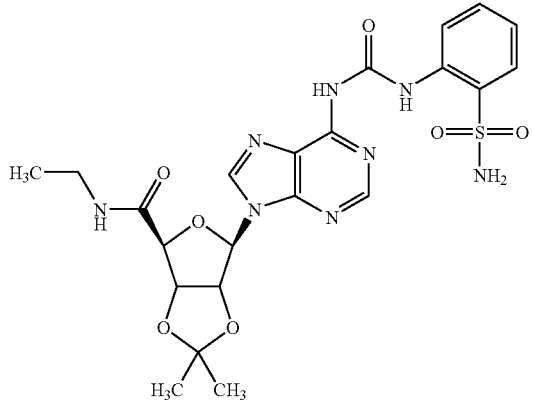

2',3'-O-Isopropylidene-$N^6$-(phenyloxycarbonyl)-adenosine-5'-ethyluronamide (Example 84, 0.188 g, 0.4 mmol) and 2-aminobenzenesulfonamide (Aldrich, 0.8 mmol) were added to a vial containing THF (4 mL, anhydrous) and heated at 50° C. overnight, at which time TLC indicated complete reaction. The solvent was removed under reduced pressure and the desired product was purified by flash chromatography on silica gel, eluting with 95:5/dichloromethane:methanol. Yield: 90 mg, 41%. White solid. m.p. 128-130° C. (decomp.). LC/MS: m/z 547.3 $[C_{22}H_{26}N_8O_7S+H]^+$ $^1$H-NMR $CD_3OD$: δ 0.67 (t, 3H, J=7.3 Hz); 1.42 (s, 3H); 1.60 (s, 3H); 2.80-2.89 (m, 2H); 4.56 (bs, 1H,); 5.54 (d, 1H, J=6.1 Hz); 5.64 (dd, 1H, $J_1$=6.1 Hz, $J_2$=1.8 Hz); 6.44 (s, 1H); 7.22-7.31 (m, 1H,); 7.57-7.66 (m, 1H); 7.99 (dd, 1H, $J_1$=7.9 Hz, $J_2$=1.4 Hz); 8.19 (dd, 1H, $J_1$=8.2 Hz, $J_2$=0.6 Hz); 8.45 (s, 1H); 8.59 (s, 1H).

Example 106

Synthesis of 1-Deoxy-N-ethyl-2,3-O-(isopropylidene)-1-[[6-[[[2-N-(isopropyl)-N-(methyl)sulfonamidophenyl]amino]carbonyl]amino]-9H-purin-9-yl]-β-D-ribofuranuronamide

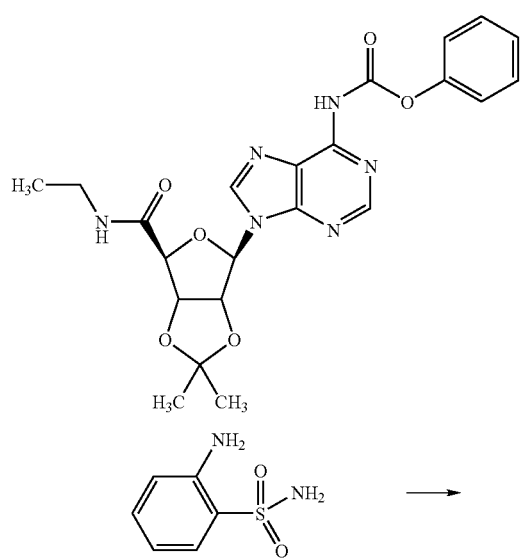

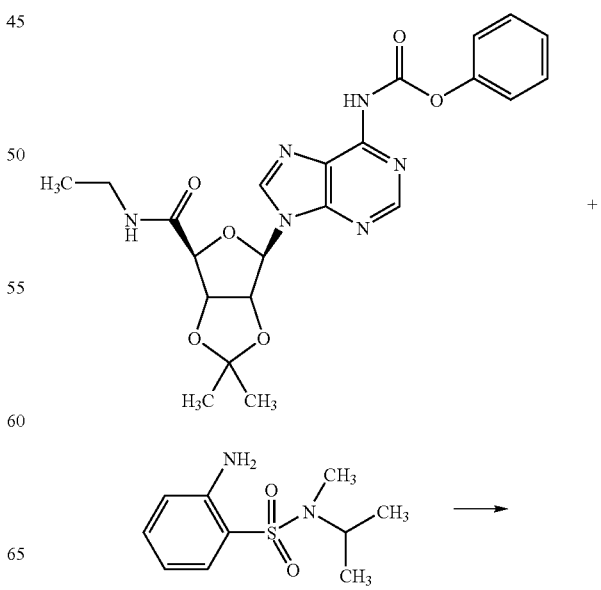

-continued

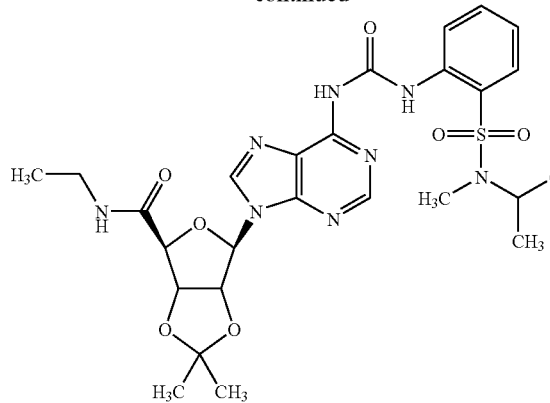

2',3'-O-Isopropylidene-N[6]-(phenyloxycarbonyl)-adenosine-5'-ethyluronamide (Example 84, 0.188 g, 0.4 mmol) and N-(isopropyl)-N-(methyl)-2-aminobenzenesulfonamide (Example 95, 0.8 mmol) were added to a vial containing THF (4 mL, anhydrous) and heated at 50° C. overnight, at which time TLC indicated complete reaction. The solvent was removed under reduced pressure and the desired product was purified by flash chromatography on silica gel, eluting with 95:5/dichloromethane:methanol. Yield: 45 mg, 19%. White solid m.p. 132-134° C. LC/MS: m/z 603.6 [$C_{26}H_{34}N_8O_7S$+H]+. $^1$H-NMR CDCl$_3$: δ 0.90 (t, 3H, J=7.3 Hz); 0.99 (d, 6H, J=6.7 Hz); 1.40 (s, 3H); 1.64 (s, 3H); 2.67 (s, 3H); 3.11-3.16 (m, 2H); 4.11-4.19 (m, 1H); 4.74 (s, 1H); 5.40 (bs, 2H); 6.14 (d, 1H, J=6.1 Hz); 6.72 (t, 1H, J=5.1 Hz); 7.23-7.28 (m, 1H); 7.57 (t, 1H, J=7.9 Hz); 7.97 (dd, 1H, $J_1$=1.5 Hz, $J_2$=8.0 Hz); 8.09 (s, 1H); 8.18 (d, 1H, J=8.3 Hz); 8.25 (s, 1H); 8.71 (s, 1H); 12.29 (s, 1H).

Example 107

Synthesis of 1-Deoxy-N-ethyl-2,3-O-(isopropylidene)-1-[[6-[[[2-N-(pentyl)-sulfonamidopheny]amino]carbonyl]amino]-9H-purin-9-yl]-β-D-ribofuran-uronamide

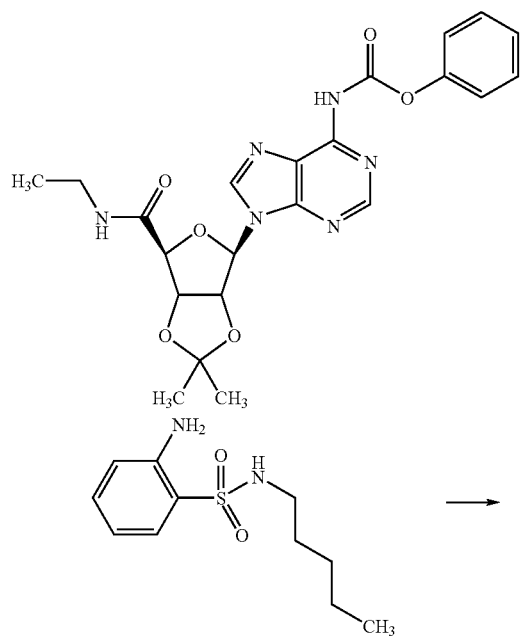

-continued

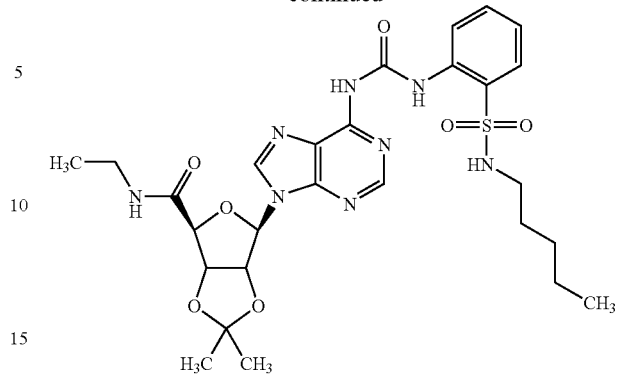

2',3'-O-Isopropylidene-N[6]-(phenyloxycarbonyl)-adenosine-5'-ethyluronamide (Example 84, 0.188 g, 0.4 mmol) and N-(pentyl)-2-aminobenzenesulfonamide (Example 96, 0.8 mmol) were added to a vial containing THF (4 mL, anhydrous) and heated at 50° C. overnight, at which time TLC indicated complete reaction. The solvent was removed under reduced pressure and the desired product was purified by flash chromatography on silica gel, eluting with 95:5/dichloromethane:methanol. Yield: 50 mg, 19%. White solid. m.p. 98-100° C. (decomp.). LC/MS: m/z 617.4 4 [$C_{27}H_{36}N_8O_7S$+H]+. $^1$H-NMR CDCl$_3$: δ 0.77 (t, 3H, J=6.7 Hz); 0.87 (t, 3H, J=7.2 Hz); 1.13-1.8 (m, 4H); 1.41 (bs, 5H); 1.64 (s, 3H); 2.92 (dd, 2H, $J_1$=13.5 Hz, $J_2$=6.8 Hz); 3.08-3.15 (m, 2H); 4.73 (d, 1H, J=1.2 Hz); 5.41 (s, 2H); 5.51 (t, 1H, J=6.05); 6.20 (d, 1H, J=2.1 Hz); 6.65 (t, 1H, J=5.6 Hz); 7.27 (t, 1H, J=7.6 Hz); 7.62 (t, 1H, J=7.6 Hz); 8.0 (dd, 1H, $J_1$=7.9 Hz, $J_2$=1.3 Hz); 8.32-8.35 (d, 1H, J=8.2 Hz), 8.38 (s, 1H); 8.68 (s, 1H); 9.35 (s, 1H); 12.01 (s, 1H).

Example 108

Synthesis of 1-Deoxy-N-ethyl-2,3-O-(isopropylidene)-1-[[6-[[[2-N-(adamantan-1-yl)-sulfonamidophenyl]amino]carbonyl]amino]-9H-purin-9-yl]-β-D-ribofuranuronamide

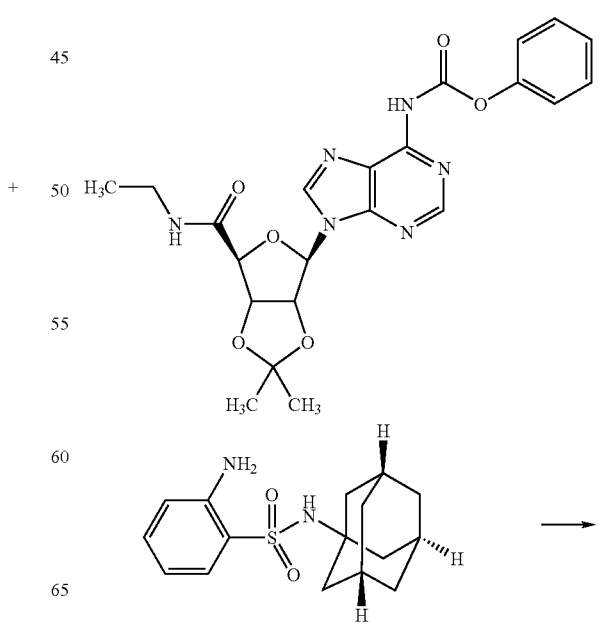

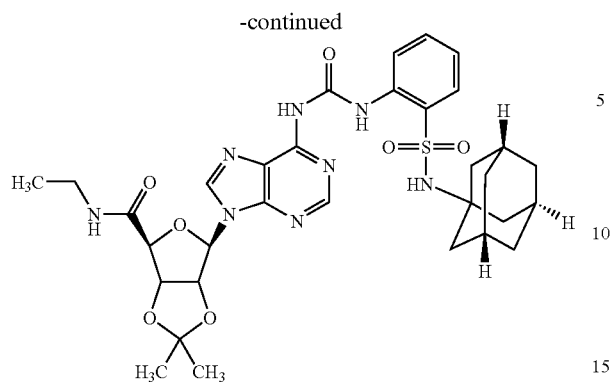

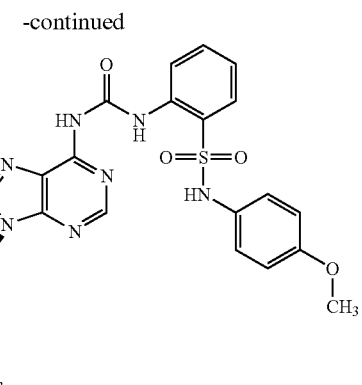

2',3'-O-Isopropylidene-N$^6$-(phenyloxycarbonyl)-adenosine-5'-ethyluronamide (Example 84, 0.188 g, 0.4 mmol) and N-(adamantan-1-yl)-2-aminobenzenesulfonamide (Example 97, 0.8 mmol) were added to a vial containing THF (4 mL, anhydrous) and heated at 50° C. overnight, at which time TLC indicated complete reaction. The solvent was removed under reduced pressure and the desired product was purified by flash chromatography on silica gel, eluting with 95:5/dichloromethane:methanol. Yield: 60 mg, 22%. White solid. m.p. 132-134° C. LC/MS: m/z 681.4 [C$_{32}$H$_{40}$N$_8$O$_7$S+H]$^+$. $^1$H-NMR CDCl$_3$: δ 0.90 (t, 3H, J=7.2 Hz); 1.41-1.69 (m, 19H), 1.95 (s, 3H); 3.08-3.17 (m, 2H); 4.74 (s, 1H); 5.42 (s, 2H); 5.55 (s, 1H); 6.18 (s, 1H); 6.63 (t, 1H, J=4.8 Hz); 7.59 (t, 1H, J=7.8 Hz); 8.05 (d, 1H, J=7.9 Hz); 8.20 (s, 1H); 8.30 (d, 1H, J=8.2 Hz); 8.58 (s, 1H); 8.70 (s, 1H); 11.67 (s, 1H).

Example 109

Synthesis of 1-Deoxy-N-ethyl-2,3-O-(isopropylidene)-1-[[6-[[[2-N-(4-methoxyphenyl)-sulfonamidophenyl]amino]carbonyl]amino]-9H-purin-9-yl]-β-D-ribofuranuronamide 2',3'-O-Isopropylidene-N$^6$-(phenyloxycarbonyl)-adenosine-5'-ethyluronamide (Example 84, 0.188 g, 0.4 mmol) and N-(4-methoxyphenyl)-2-aminobenzenesulfonamide (Example 98, 0.8 mmol) were added to a vial containing THF (4 mL, anhydrous) and heated at 50° C. overnight, at which time TLC indicated complete reaction. The solvent was removed under reduced pressure and the desired product was purified by flash chromatography on silica gel, eluting with 95:5/dichloromethane:methanol. Yield: 55 mg, 21%. White solid. m.p. 125-127° C. LC/MS: m/z 653.2 [C$_{29}$H$_{32}$N$_8$O$_8$S+H]$^+$. $^1$H-NMR CDCl$_3$: δ 0.84 (t, 3H, J=7.2 Hz); 1.40 (s, 3H); 1.62 (s, 3H); 3.03-3.12 (m, 2H); 3.65 (s, 3H,); 4.69 (s, 1H); 5.40 (s, 1H); 6.23 (bs, 2H); 6.44 (s, 1H); 6.62 (d, 2H, J=8.8 Hz); 6.76 (t, 1H, J=5.7 Hz); 6.94 (d, 2H, J=8.8 Hz); 7.103 (t, 1H, J=7.6 Hz); 7.72 (d, 1H, J=7.8 Hz); 7.96 (s, 1H); 8.17 (d, 1H, J=8.2 Hz); 8.45 (s, 1H); 8.66 (s, 1H); 9.68 (s, 1H); 12.09 (s, 1H).

Example 110

Synthesis of 1-Deoxy-N-ethyl-2,3-O-(isopropylidene)-1-[[6-[[[2-(2,5-dihydropyrrol-1-yl)sulfonylphenyl]amino]carbonyl]amino]-9H-purin-9-yl]-β-D-ribofuranuronamide

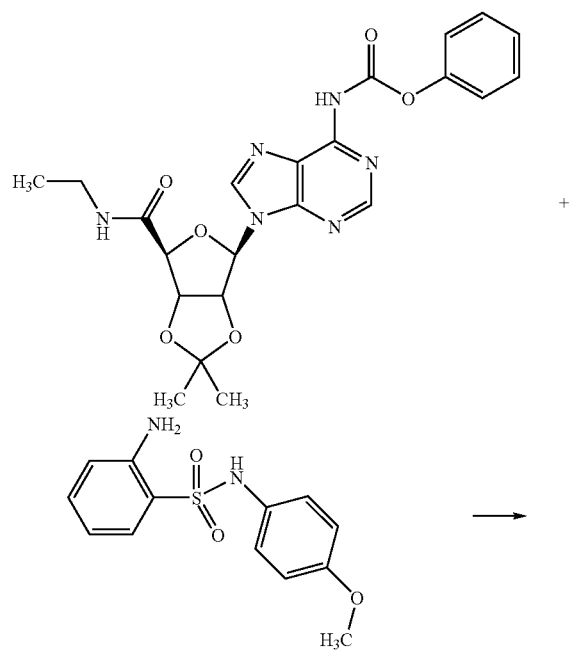

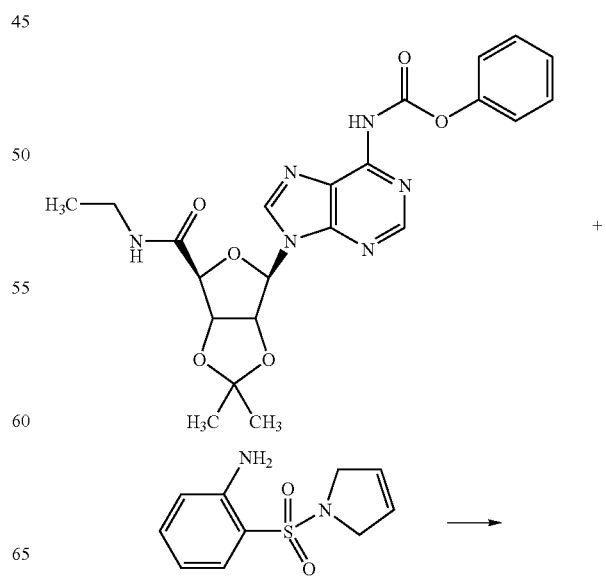

91

-continued

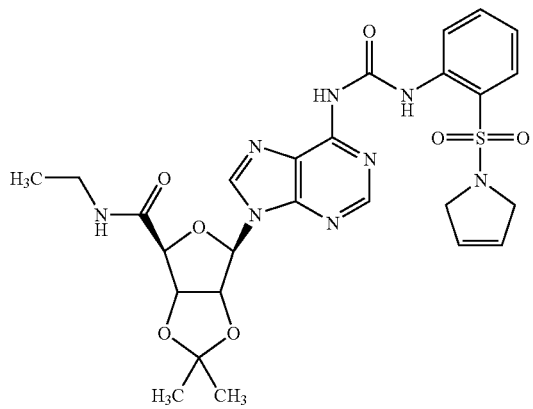

2',3'-O-Isopropylidene-N[6]-(phenyloxycarbonyl)-adenosine-5'-ethyluronamide (Example 84, 0.188 g, 0.4 mmol) and 2-(2,5-Dihydropyrrol-1-yl-sulfonyl)-aniline (Example 103, 0.8 mmol) were added to a vial containing THF (4 mL, anhydrous) and heated at 50° C. overnight, at which time TLC indicated complete reaction. The solvent was removed under reduced pressure and the desired product was purified by flash chromatography on silica gel, eluting with 95:5/dichloromethane:methanol. Yield: 55 mg, 23%. White solid. m.p. 130-132° C. LC/MS: m/z 599.2 $[C_{26}H_{30}N_8O_7S+H]^+$. $^1$H-NMR CDCl$_3$: δ 0.84 (t, 3H, J=7.3 Hz); 1.41 (s, 3H); 1.64 (s, 3H); 3.03-3.12 (m, 2H); 4.15 (bs, 4H); 4.73 (s, 1H); 5.46 (s, 2H); 5.68 (s, 2H); 6.22 (s, 1H); 6.72-6.76 (t, 1H, J=5.4 Hz); 7.24 (t, 1H, J=7.7 Hz); 7.60 (t, 1H, J=7.7 Hz); 7.88 (d, 1H, J=7.9 Hz); 8.35 (d, 1H, J=8.3 Hz); 8.44 (s, 1H); 8.71 (s, 1H); 9.54 (s, 1H); 12.69 (s, 1H).

Example 111

Synthesis of 1-Deoxy-N-ethyl-2,3-O-(isopropylidene)-1-[[6-[[(3-sulfonamidophenyl)amino]carbonyl]amino]-9H-purin-9-yl]-β-D-ribofuranuron-amide

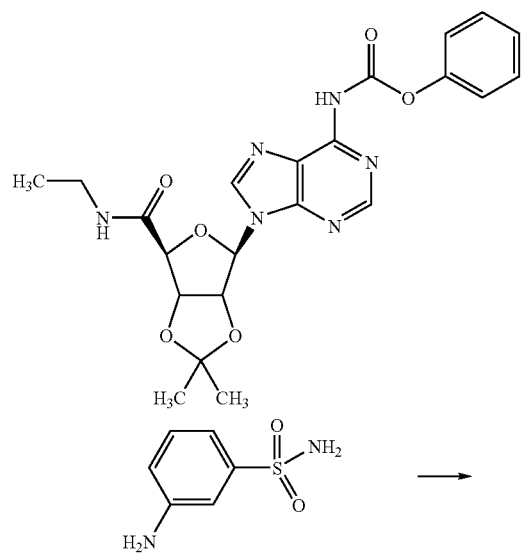

92

-continued

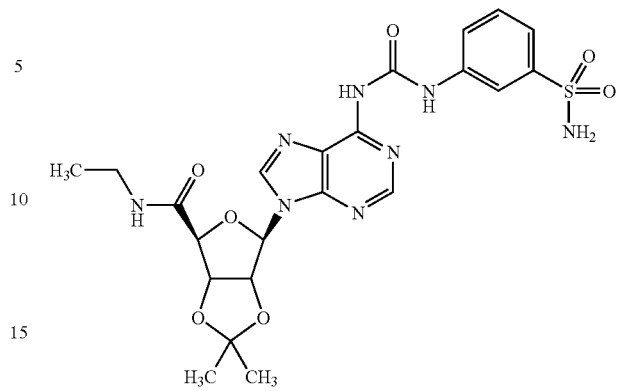

2',3'-O-Isopropylidene-N[6]-(phenyloxycarbonyl)-adenosine-5'-ethyluronamide (Example 84, 0.188 g, 0.4 mmol) and 3-aminobenzenesulfonamide (Aldrich, 0.8 mmol) were added to a vial containing THF (4 mL, anhydrous) and heated at 50° C. overnight, at which time TLC indicated complete reaction. The solvent was removed under reduced pressure and the desired product was purified by flash chromatography on silica gel, eluting with 95:5/dichloromethane:methanol. Yield: 60 mg, 27%. White solid. m.p. 179-181° C. (decomp.). LC/MS: m/z 547.3 $[C_{22}H_{26}N_8O_7S+H]^+$. $^1$H-NMR (CDCl$_3$): δ 0.87 (t, 3H, J=7.3 Hz); 1.44 (s, 3H); 1.67 (s, 3H); 3.01-3.19 (m, 2H); 4.73 (d, 1H, J=2.0 Hz); 5.41 (m, 1H,); 5.48 (m, 3H); 6.25 (d, 1H, J=3.0 Hz); 6.51 (m, 1H); 7.42 (m, 1H,); 7.49 (m, 1H); 7.61 (m, 1H); 8.48 (s, 1H); 8.55 (s, 1H); 8.57 (bs, 1H); 9.77 (bs, 1H); 12.11 (bs, 1H).

Example 112

Synthesis of 1-Deoxy-N-ethyl-2,3-O-(isopropylidene)-1-[[6-[[[3-N-(isopropyl)-N-(methyl)sulfonamidophenyl]amino]carbonyl]amino]-9H-purin-9-yl]-β-D-ribofuranuronamide

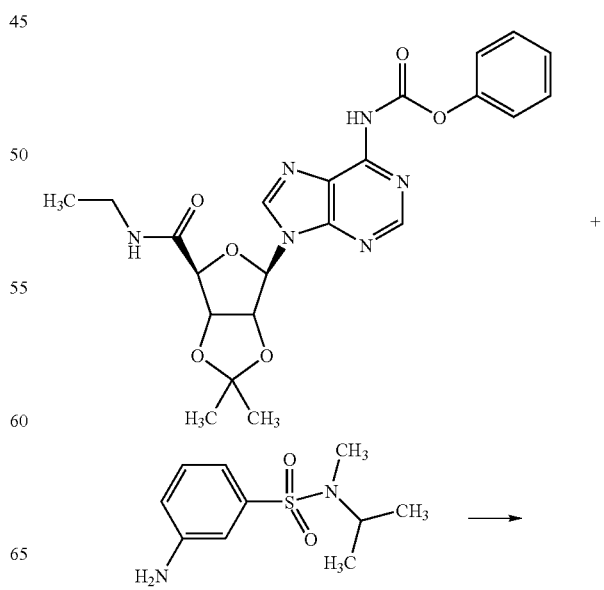

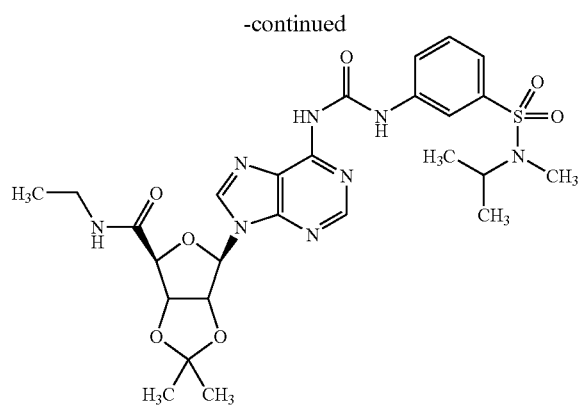

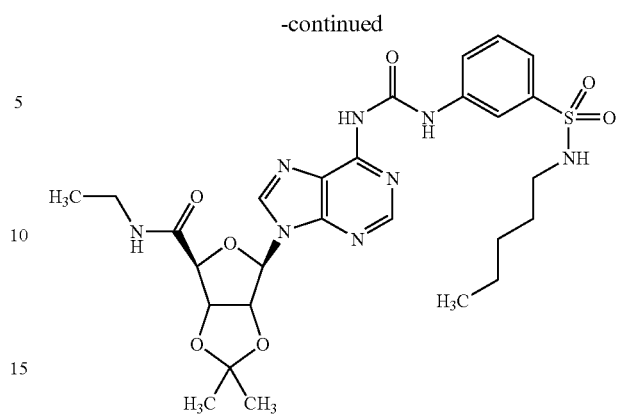

2',3'-O-Isopropylidene-N⁶-(phenyloxycarbonyl)-adenosine-5'-ethyluronamide (Example 84, 0.188 g, 0.4 mmol) and N-(isopropyl)-N-(methyl)-3-aminobenzenesulfonamide (Example 99, 0.8 mmol) were added to a vial containing THF (4 mL, anhydrous) and heated at 50° C. overnight, at which time TLC indicated complete reaction. The solvent was removed under reduced pressure and the desired product was purified by flash chromatography on silica gel, eluting with 95: 5/dichloromethane:methanol. Yield: 91 mg, 38%. White solid. m.p. 149-151° C. LC/MS: m/z 603.6 [$C_{26}H_{34}N_8O_7S$+H]⁺. ¹H-NMR (CDCl₃): δ 0.86 (t, 3H, J=7.3 Hz); 1.03 (d, 6H, J=6.7 Hz); 1.41 (s, 3H); 1.64 (s, 3H); 2.77 (s, 3H); 3.0-3.15 (m, 2H); 3.49 (d, 2H, J=4.8 Hz); 4.25-4.35 (m, 1H); 4.74 (d, 1H, J=1.7 Hz); 5.45-5.48 (m, 1H,); 6.19 (d, 1H, J=2.4 Hz); 7.50-7.55 (m, 2H); 7.95-8.05 (m, 2H); 8.16 (s, 1H); 8.48 (s, 1H); 8.65 (s, 1H).

Example 113

Synthesis of 1-Deoxy-N-ethyl-2,3-O-(isopropylidene)-1-[[6-[[[3-N-(pentyl)-sulfonamidophenyl]amino]carbonyl]amino]-9H-purin-9-yl]-β-D-ribofuranuronamide 2',3'-O-Isopropylidene-N⁶-(phenyloxycarbonyl)-adenosine-5'-ethyluronamide (Example 84, 0.188 g, 0.4 mmol) and N-(pentyl)-3-aminobenzenesulfonamide (Example 100, 0.8 mmol) were added to a vial containing THF (4 mL, anhydrous) and heated at 50° C. overnight, at which time TLC indicated complete reaction. The solvent was removed under reduced pressure and the desired product was purified by flash chromatography on silica gel, eluting with 95:5/dichloromethane:methanol. Yield: 101 mg, 41%. White solid. m.p. 130-132° C. LC/MS: m/z 617.4 [$C_{27}H_{36}N_8O_7S$+H]⁺. ¹H-NMR (CDCl₃): δ 0.83 (m, 6H); 1.23 (m, 4H); 1.42 (s, 3H); 1.50 (m, 2H); 1.65 (s, 3H); 2.90-3.20 (m, 4H); 3.50 (d, 1H, J=4.3 Hz); 4.70 (d, 1H, J=2.8 Hz); 5.40-5.55 (m, 3H,); 6.28 (d, 1H, J=2.5 Hz); 6.55 (m, 1H); 7.55 (m, 1H); 7.65 (m, 2H); 8.38 (s, 1H); 8.53 (s, 1H); 8.58 (s, 1H); 9.75 (bs, 1H).

Example 114

Synthesis of 1-Deoxy-N-ethyl-2,3-O-(isopropylidene)-1-[[6-[[[3-N-(adamantan-1-yl)-sulfonamidophenyl]amino]carbonyl]amino]-9H-purin-9-yl]-β-D-ribofuranuronamide

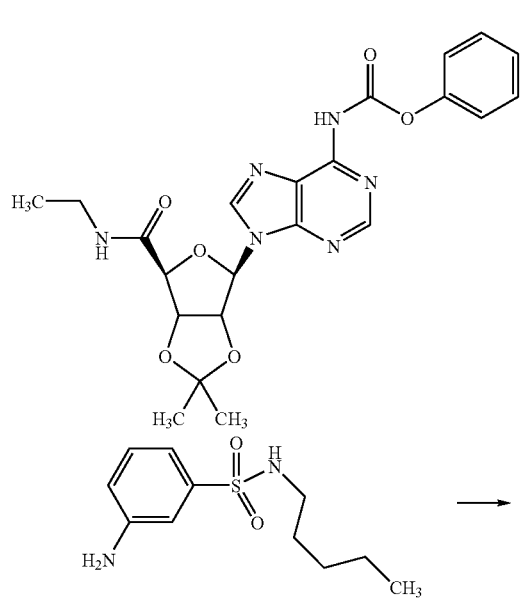

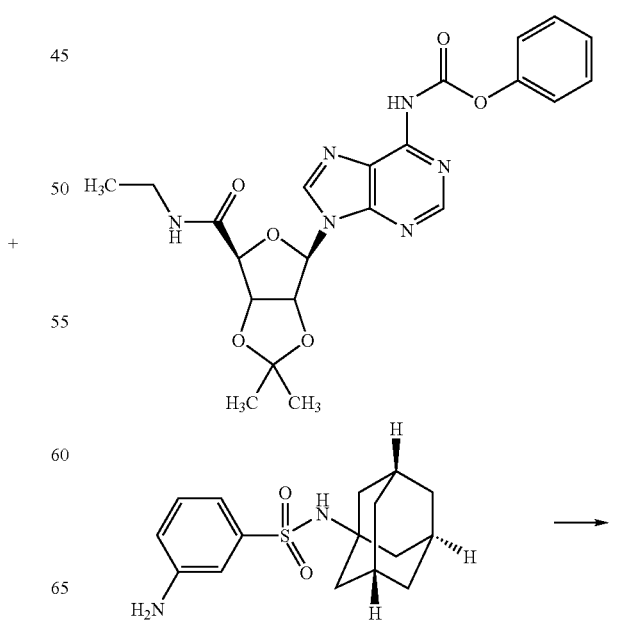

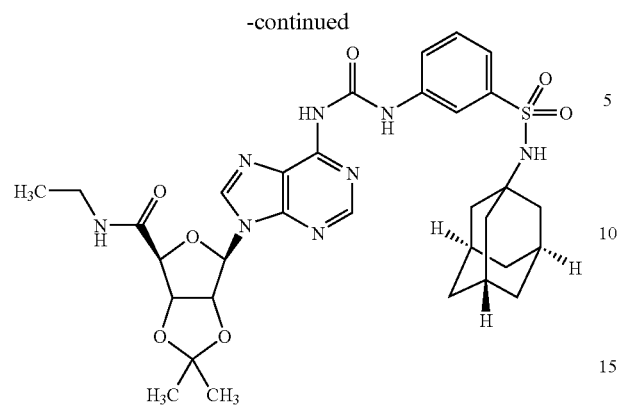

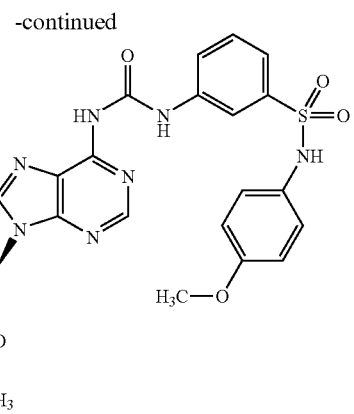

2',3'-O-Isopropylidene-N⁶-(phenyloxycarbonyl)-adenosine-5'-ethyluronamide (Example 84, 0.188 g, 0.4 mmol) and N-(adamantan-1-yl)-3-aminobenzenesulfonamide (Example 101, 0.8 mmol) were added to a vial containing THF (4 mL, anhydrous) and heated at 50° C. overnight, at which time TLC indicated complete reaction. The solvent was removed under reduced pressure and the desired product was purified by flash chromatography on silica gel, eluting with 95:5/dichloromethane:methanol. Yield: 74 mg, 27%. White solid. m.p. 175-177° C. LC/MS: m/z 681.4 [$C_{32}H_{40}N_8O_7S$+H]⁺. ¹H-NMR (CDCl₃): δ 0.83 (t, 3H, J=7.3 Hz); 1.42 (s, 3H); 1.57 (bs, 6H), 1.65 (s, 3H); 1.83 (bs, 6H); 2.0 (bs, 3H); 2.95-3.20 (m, 2H); 3.49 (d, 2H, J=4.5 Hz); 4.74 (d, 1H, J=1.8 Hz); 5.15 (bs, 1H,); 5.50 (m, 1H); 5.60 (m, 1H); 6.25 (d, 1H, J=1.8 Hz); 6.45 (m, 1H); 7.46 (m, 1H); 7.62-7.80 (m, 2H); 8.32 (bs, 1H); 8.39 (bs, 1H); 8.63 (s, 1H).

Example 115

Synthesis of 1-Deoxy-N-ethyl-2,3-O-(isopropylidene)-1-[[6-[[[3-N-(4-methoxyphenyl)-sulfonamidophenyl]amino]carbonyl]amino]-9H-purin-9-yl]-β-D-ribofuranuronamide 2',3'-O-Isopropylidene-N⁶-(phenyloxycarbonyl)-adenosine-5'-ethyluronamide (Example 84, 0.188 g, 0.4 mmol) and N-(4-methoxyphenyl)-3-aminobenzenesulfonamide (Example 102, 0.8 mmol) were added to a vial containing THF (4 mL, anhydrous) and heated at 50° C. overnight, at which time TLC indicated complete reaction. The solvent was removed under reduced pressure and the desired product was purified by flash chromatography on silica gel, eluting with 16:3:1/ethyl acetate:dichloromethane:methanol. Yield: 66 mg, 25%. White solid. m.p. 128-130° C. LC/MS: m/z 653.2 [$C_{29}H_{32}N_8O_8S$+H]⁺. ¹H-NMR (CDCl₃): δ 0.87 (t, 3H, J=8.0 Hz); 1.41 (s, 3H); 1.66 (s, 3H); 3.0-3.20 (m, 2H); 3.71 (s, 3H); 4.66 (d, 1H, J=2.0 Hz); 5.31 (m, 1H,); 5.44 (m, 1H); 6.26 (d, 1H, J=3.0 Hz); 6.72 (d, 2H, J=9.0 Hz); 7.12 (d, 3H, J=9.0 Hz); 7.24-7.32 (m, 3H); 7.95 (bs, 1H); 8.53 (s, 1H); 8.58 (bs, 1H); 8.71 (bs, 1H); 10.3 (bs, 1H); 12.1 (bs, 1H).

Example 116

Synthesis of 1-Deoxy-N-ethyl-2,3-O-(isopropylidene)-1-[[6-[[[3-(2,5-dihydropyrrol-1-yl)sulfonylphenyl]amino]carbonyl]amino]-9H-purin-9-yl]-β-D-ribofuranuronamide

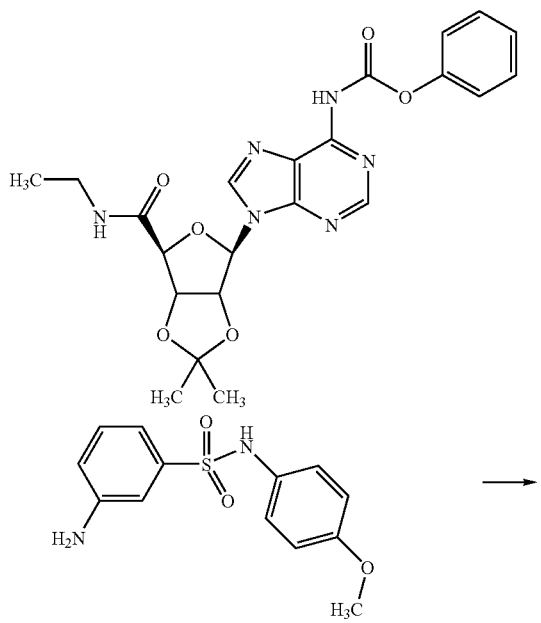

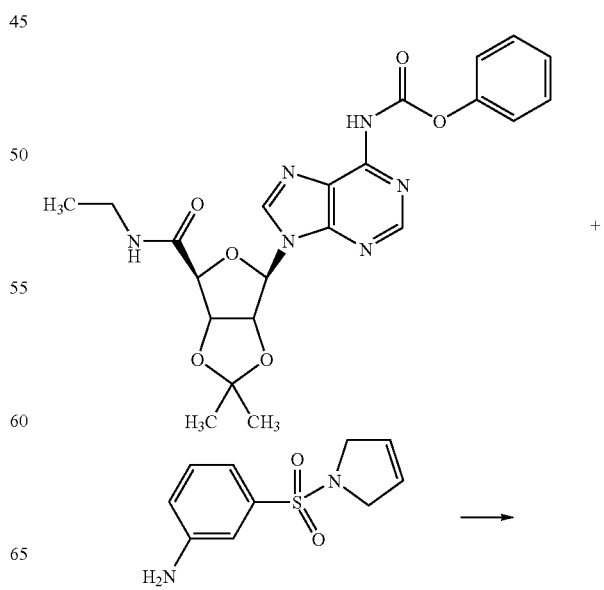

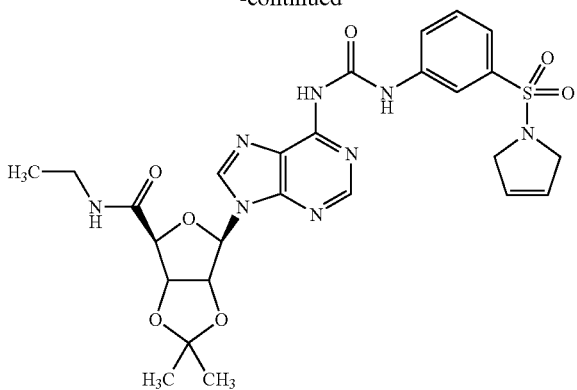

2',3'-O-Isopropylidene-N⁶-(phenyloxycarbonyl)-adenosine-5'-ethyluronamide (Example 84, 0.188 g, 0.4 mmol) and 3-(2,5-Dihydropyrrol-1-yl-sulfonyl)-aniline (Example 104, 0.8 mmol) were added to a vial containing THF (4 mL, anhydrous) and heated at 50° C. overnight, at which time TLC indicated complete reaction. The solvent was removed under reduced pressure and the desired product was purified by flash chromatography on silica gel, eluting with 95:5/dichloromethane:methanol. Yield: 86 mg, 36%. White solid. m.p. 127-129° C. LC/MS: m/z 599.2 $[C_{26}H_{30}N_8O_7S+H]^+$. $^1$H-NMR (CDCl$_3$): δ 0.86 (t, 3H, J=7.3 Hz); 1.41 (s, 3H); 1.64 (s, 3H); 3.04-3.10 (m, 2H); 3.49 (d, 2H, J=4.8 Hz); 4.19 (s, 4H); 4.73 (d, 1H, J=1.7 Hz); 5.46-5.48 (m, 2H); 5.68 (s, 2H); 6.19 (s, 1H); 7.53-7.57 (m, 2H); 8.04 (m, 2H); 8.17 (s, 1H); 8.51 (bs, 1H); 8.65 (s, 1H).

Example 117

Synthesis of 1-Deoxy-N-ethyl-1-[[6-[[[2-N-(4-methoxyphenyl)-sulfonamidophenyl]amino]carbonyl]amino]-9H-purin-9-yl]-β-D-ribofuran-uronamide

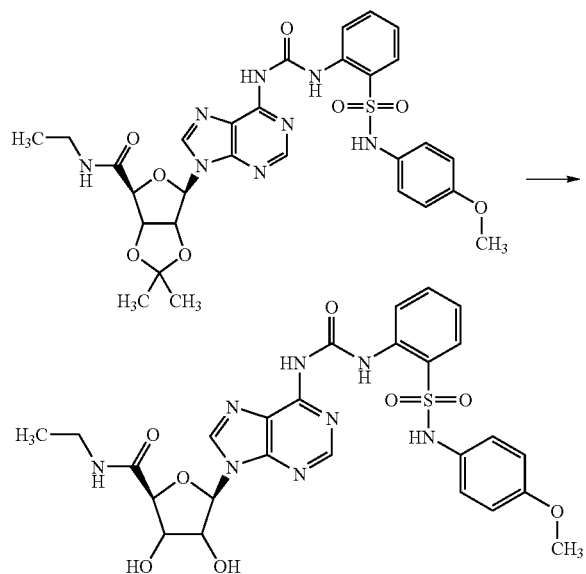

1-Deoxy-N-ethyl-2,3-O-(isopropylidene)-1-[[6-[[[2-N-(4-methoxyphenyl)-sulfonamido-phenyl]amino]carbonyl]amino]-9H-purin-9-yl]-β-D-ribofuranuronamide (Example 109, 0.066 g, 0.1 mmol) was dissolved in 1 N HCl (1.5 mL) and 1,4-dioxane (1.5 mL). The solution thus obtained was heated to 65° C. for 1 hour. After the reaction was complete by TLC (ethyl acetate:dichloromethane:methanol/80:15:5), the 1,4-dioxane was removed under reduced pressure. After adjusting the pH to neutrality with 2 N NaOH, the precipitated product is collected by filtration. The white solid was dissolved in methanol and purified by chromatography with dichloromethane: methanol (90:10). Fractions containing the desired product were combined and evaporated to dryness, affording the compound as a white solid. Yield: 41 mg, 79%. m.p. 168-170° C. LC/MS: m/z 613.2 $[C_{26}H_{28}N_8O_8S+H]^+$. $^1$H-NMR (CD$_3$OD): δ 1.25 (t, 3H, J=7.3 Hz); 3.40 (q, 2H, J=7.2 Hz); 3.55 (s, 3H); 4.39 (dd, 1H, J=1.8 Hz, J=4.8 Hz); 4.52 (d, 1H, J=1.7 Hz); 6.15 (d, 1H, J=7.3 Hz); 6.49 (d, 2H, J=8.9 Hz); 6.89 (d, 2H, J=8.9 Hz); 7.24 (t, 1H, J=7.6 Hz); 7.58 (t, 1H, J=7.8 Hz); 7.89 (dd, 1H, J=1.3 Hz, J=7.9 Hz); 8.07 (d, 1H, J=8.2 Hz); 8.58 (s, 1H); 8.62 (s, 1H).

Example 118

Synthesis of 1-Deoxy-N-ethyl-1-[[6-[[[3-N-(pentyl)-sulfonamido-phenyl]amino]carbonyl]amino]-9H-purin-9-yl]-β-D-ribofuranuronamide

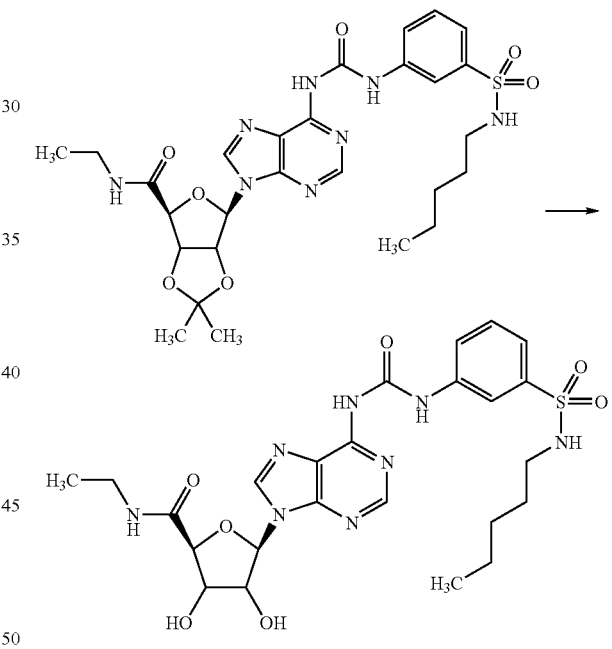

1-Deoxy-N-ethyl-2,3-O-(isopropylidene)-1-[[6-[[[3-N-(pentyl)-sulfonamidophenyl]-amino]carbonyl]amino]-9H-purin-9-yl]-β-D-ribofuranuronamide (Example 113, 0.066 g, 0.1 mmol) was dissolved in 1 N HCl (1.5 mL) and 1,4-dioxane (1.5 mL). The solution thus obtained was heated to 65° C. for 1 hour. After the reaction was complete by TLC (ethyl acetate:dichloromethane:methanol/80:15:5), the 1,4-dioxane was removed under reduced pressure. The pH to was adjusted to neutrality with 2 N NaOH and the precipitated product collected by filtration. The white solid was dissolved in methanol and purified by chromatography, eluting with dichloromethane:methanol (90:10). Fractions containing the desired product were combined and evaporated to dryness, affording the product as a white solid. Yield: 77 mg, 82%. m.p. 158-159° C. LC/MS: m/z 577.4 $[C_{24}H_{32}N_8O_7S+H]^+$. $^1$H-NMR (CD$_3$OD): δ 0.86 (t, 3H, J=7.0 Hz); 1.21 (t, 3H, J=7.3 Hz); 1.28 (m, 3H); 1.46 (m, 2H); 2.89 (t, 2H, J=7.0 Hz); 3.37 (q, 2H, J=7.4 Hz); 4.39 (dd, 1H, J=1.8 Hz, J=4.8 Hz); 4.49 (d, 1H, J=1.9 Hz); 6.14 (d, 1H, J=7.2 Hz); 7.57 (m, 2H); 7.82 (td, 1H, J=2.0 Hz, J=7.2 Hz); 8.24 (s, 1H); 8.57 (s, 1H); 8.73 (d, 1H).

Example 119

Synthesis of 1-Deoxy-N-ethyl-1-[[6-[[[3-N-(4-methoxyphenyl)-sulfonamidophenyl]amino]carbonyl]amino]-9H-purin-9-yl]-β-D-ribofuran-uronamide

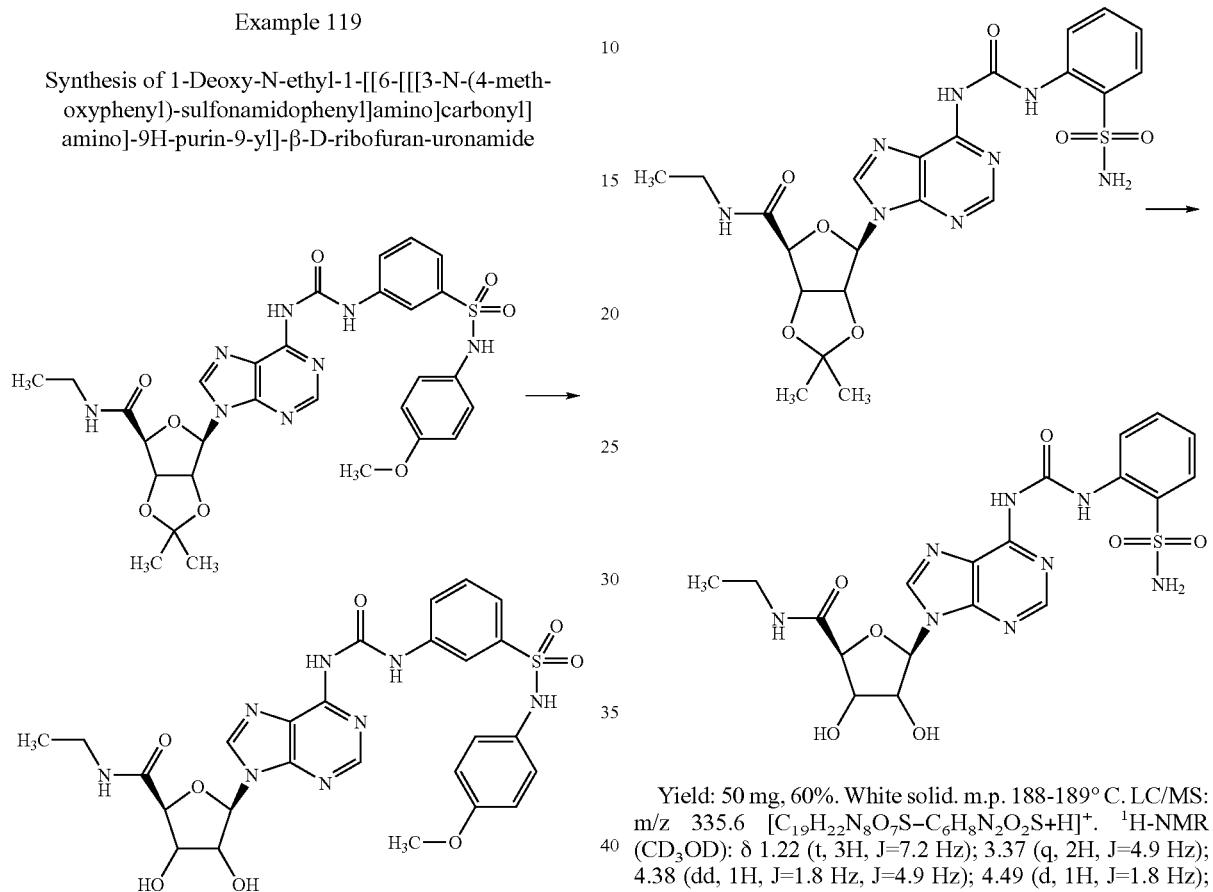

1-Deoxy-N-ethyl-2,3-O-(isopropylidene)-1-[[6-[[[3-N-(4-methoxyphenyl)-sulfonamido-phenyl]amino]carbonyl]amino]-9H-purin-9-yl]-β-D-ribofuranuronamide (Example 115, 0.066 g, 0.1 mmol) was dissolved in 1 N HCl (1.5 mL) and 1,4-dioxane (1.5 mL). The solution was heated to 65° C. for 1 hour. After the reaction was complete by TLC (ethyl acetate:dichloromethane:methanol/80:15:5), the 1,4-dioxane was removed under reduced pressure. After adjusting the pH to neutrality with 2 N NaOH, the precipitated product was collected by filtration. The white solid was dissolved in DMF (1 mL), followed by the addition of diethyl ether (20 mL) affording the desired product which was collected by filtration as a white solid. Yield: 45 mg, 74%. m.p. 206-208° C. (decomp.). LC/MS: m/z 613.2 $[C_{26}H_{28}N_8O_8S+H]^+$. $^1$H-NMR (DMSO-$d_6$): δ 1.08 (t, 3H); 3.22 (m, 2H); 3.65 (s, 3H); 4.18 (s, 1H); 4.36 (s, 1H); 4.63 (m, 1H); 5.65 (m, 1H); 5.74 (s, 1H); 6.11 (m, 1H); 6.80 (d, 2H, J=8.0 Hz); 7.01 (d, 2H, J=8 Hz); 7.37 (m, 1H); 7.50 (m, 1H); 7.73 (m, 1H); 8.16 (s, 1H); 8.45 (bs, 1H); 8.71 (s, 1H); 8.80 (s, 1H); 9.98 (bs, 1H); 9.40 (bs, 1H).

In a similar manner to Examples 117, 118, and 119, the following compounds were prepared:

Example 120

Synthesis of 1-Deoxy-N-ethyl-1-[[6-[[(2-sulfonamidophenyl)amino]-carbonyl]amino]-9H-purin-9-yl]-β-D-ribofuranuronamide

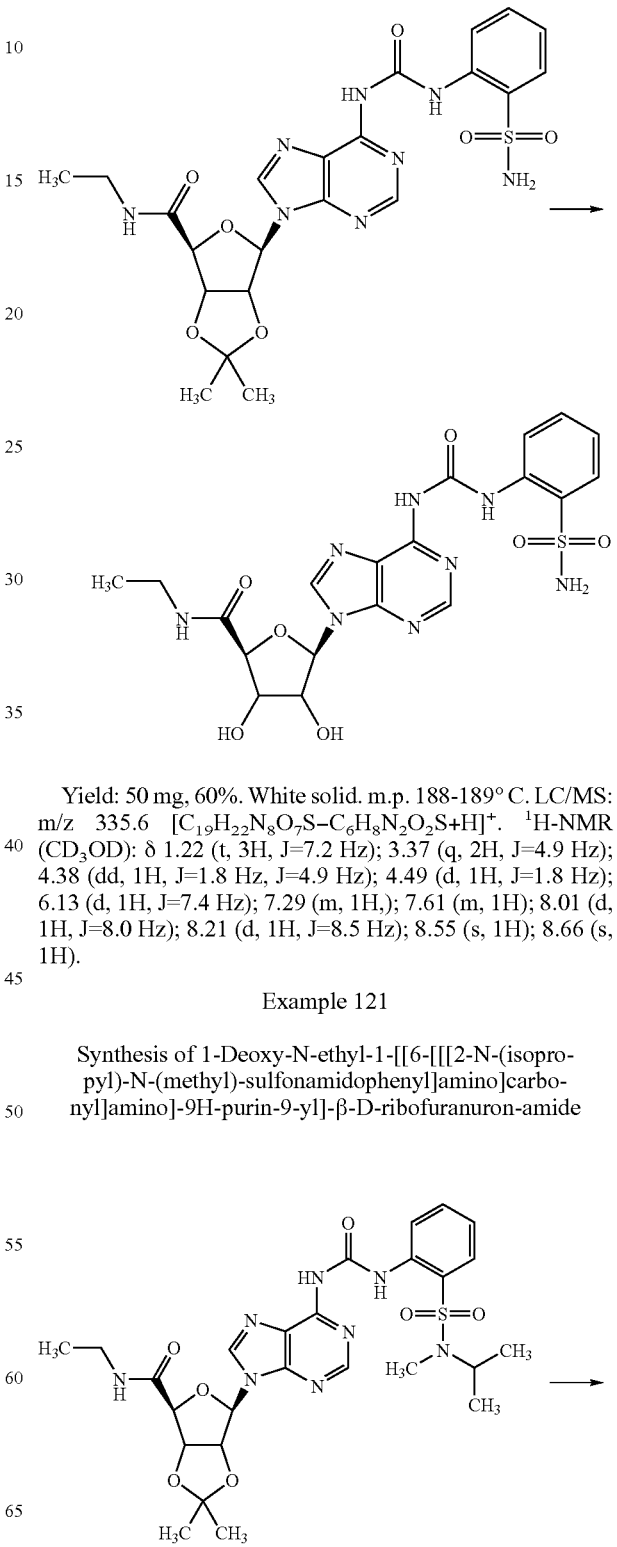

Yield: 50 mg, 60%. White solid. m.p. 188-189° C. LC/MS: m/z 335.6 $[C_{19}H_{22}N_8O_7S-C_6H_8N_2O_2S+H]^+$. $^1$H-NMR (CD$_3$OD): δ 1.22 (t, 3H, J=7.2 Hz); 3.37 (q, 2H, J=4.9 Hz); 4.38 (dd, 1H, J=1.8 Hz, J=4.9 Hz); 4.49 (d, 1H, J=1.8 Hz); 6.13 (d, 1H, J=7.4 Hz); 7.29 (m, 1H,); 7.61 (m, 1H); 8.01 (d, 1H, J=8.0 Hz); 8.21 (d, 1H, J=8.5 Hz); 8.55 (s, 1H); 8.66 (s, 1H).

Example 121

Synthesis of 1-Deoxy-N-ethyl-1-[[6-[[[2-N-(isopropyl)-N-(methyl)-sulfonamidophenyl]amino]carbonyl]amino]-9H-purin-9-yl]-β-D-ribofuranuron-amide -continued

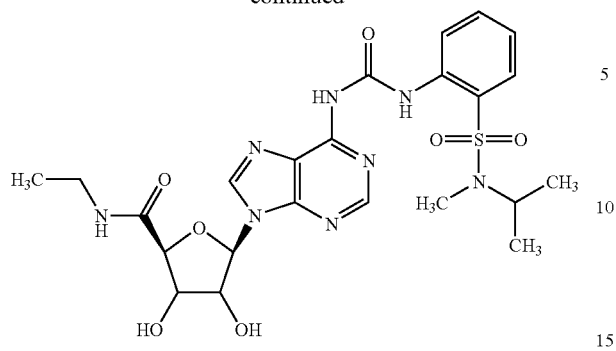

Yield: 24 mg, 57%. White solid. m.p. 142-144° C. LC/MS: m/z 563.2 $[C_{23}H_{30}N_8O_7S+H]^+$. $^1$H-NMR (CD$_3$OD): δ 0.97 (d, 6H, J=6.7 Hz); 1.21 (t, 3H, J=7.3 Hz); 2.67 (s, 3H); 3.38 (q, 2H, J=7.3 Hz); 4.10 (m, 1H); 4.39 (dd, 1H, J=1.8 Hz, J=4.8 Hz); 4.49 (d, 1H, J=1.8 Hz); 6.14 (d, 1H, J=7.3 Hz); 7.32 (t, 1H, J=7.7 Hz); 7.64 (t, 1H, J=7.8 Hz); 7.96 (dd, 1H, J$_1$=1.4 Hz, J$_2$=8.0 Hz); 8.10 (d, 1H, J=8.2 Hz); 8.57 (s, 1H); 8.69 (s, 1H).

Example 122

Synthesis of 1-Deoxy-N-ethyl-1-[[6-[[[2-N-(pentyl)-sulfonamido-phenyl]amino]carbonyl]amino]-9H-purin-9-yl]-β-D-ribofuranuronamide

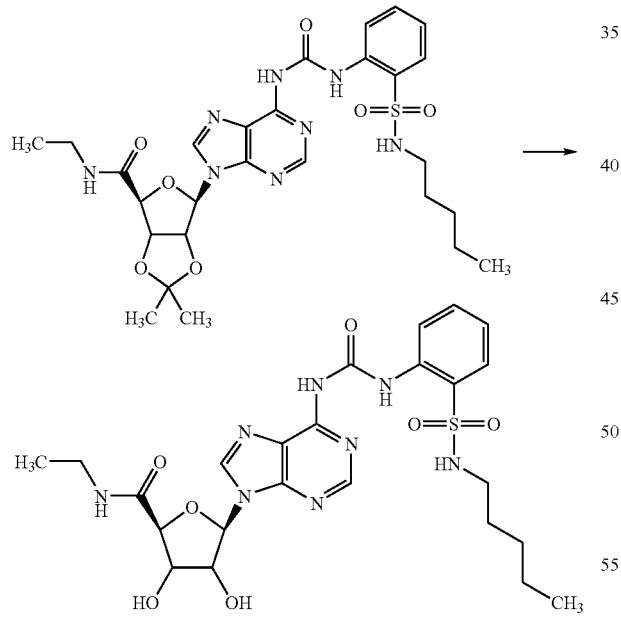

Yield: 46 mg, 98%. White solid. m.p. 155-157° C. LC)/MS: m/z 577.2 $[C_{24}H_{32}N_8O_7S+H]^+$. $^1$H-NMR (CD$_3$OD): δ 0.78 (t, 3H, J=6.8 Hz); 1.14 (m, 4H); 1.23 (t, 3H, J=7.3 Hz); 1.36 (m, 2H); 2.89 (t, 3H, J=7.1 Hz); 3.38 (q, 2H, J=6.7 Hz); 4.37 (dd, 1H, J$_1$=1.7 Hz, J$_2$=4.8 Hz); 4.49 (d, 1H, J=1.8 Hz); 6.13 (d, 1H, J=7.3 Hz); 7.32 (t, 1H, J=7.7 Hz); 7.63 (t, 1H, J=7.8 Hz); 7.95 (dd, 1H, J$_1$=1.5 Hz, J$_2$=8.0 Hz); 8.19 (d, 1H, J=7.5 Hz); 8.56 (s, 1H); 8.66 (s, 1H).

Example 123

Synthesis of 1-Deoxy-N-ethyl-1-[[6-[[[2-N-(adamantan-1-yl)-sulfonamidophenyl]amino]carbonyl]amino]-9H-purin-9-yl]-β-D-ribofuran-uronamide

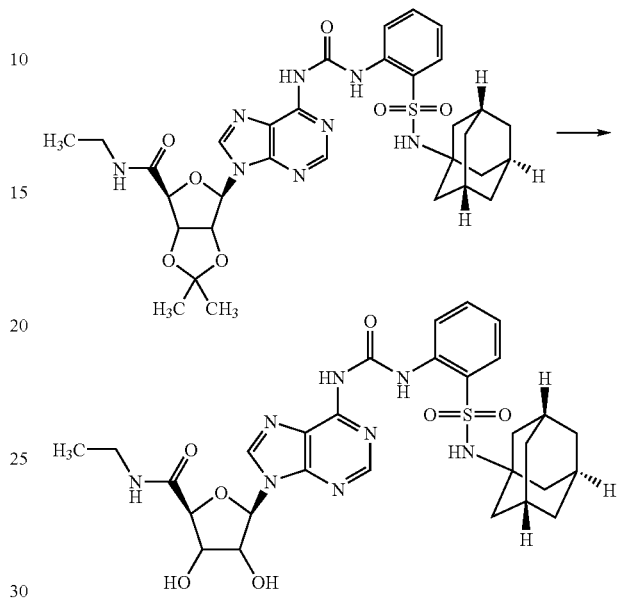

Yield: 22 mg, 39%. White solid. m.p. 159-161° C. LC/MS: m/z 641.4 $[C_{29}H_{36}N_8O_7S+H]^+$. $^1$H-NMR (CD$_3$OD): δ 1.22 (t, 3H, J=7.2 Hz); 1.56 (q, 6H, J=12.3 Hz); 1.74 (s, 6H); 1.91 (s, 3H); 3.37 (q, 2H, J=7.3 Hz); 4.38 (dd, 1H, J$_1$=1.9 Hz, J$_2$=4.9 Hz); 4.49 (d, 1H, J=1.8 Hz); 6.14 (d, 1H, J=7.3 Hz); 7.32 (t, 1H, J=7.7 Hz); 7.63 (t, 1H, J=7.8 Hz); 8.01 (dd, 1H, J$_1$=1.4 Hz, J$_2$=8.0 Hz); 8.09 (d, 1H, J=8.2 Hz); 8.56 (s, 1H); 8.66 (s, 1H).

Example 124

Synthesis of 1-Deoxy-N-ethyl-1-[[6-[[[2-(2,5-dihydropyrrol-1-yl)sulfonylphenyl]amino]carbonyl]amino]-9H-purin-9-yl]-β-D-ribofuranuronamide

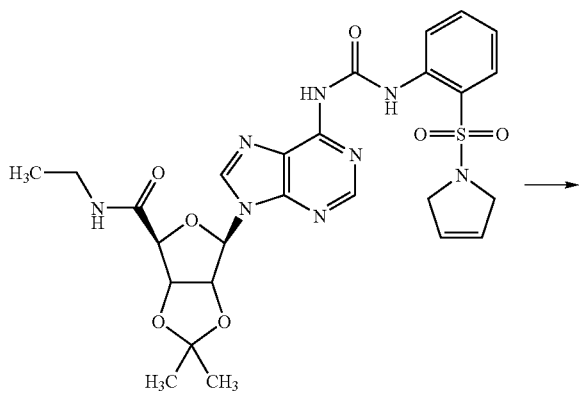

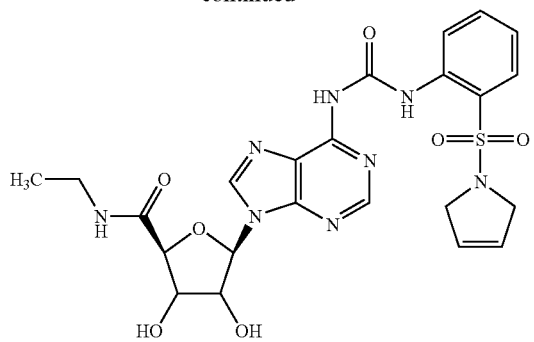

Yield: 26 mg, 51%. White solid. m.p. 149-151° C. LC/MS: m/z 559.2 $[C_{23}H_{26}N_8O_7S+H]^+$. $^1$H-NMR (CD$_3$OD): δ 1.21 (t, 3H, J=7.3 Hz); 3.37 (q, 2H, J=7.3 Hz); 4.11 (s, 4H); 4.39 (dd, 1H, J$_1$=1.8 Hz, J$_2$=4.8 Hz); 4.49 (d, 1H, J=1.8 Hz); 5.48 (s, 1H); 5.73 (s, 2H); 6.14 (d, 1H, J=7.3 Hz); 7.33 (t, 1H, J=7.3 Hz); 7.65 (t, 1H, J=7.8 Hz); 7.90 (dd, 1H, J$_1$=1.3 Hz, J$_2$=7.9 Hz); 8.20 (d, 1H, J=8.1 Hz); 8.56 (s, 1H); 8.67 (s, 1H).

Example 125

Synthesis of 1-Deoxy-N-ethyl-1-[[6-[[(3-sulfonamidophenyl)-amino]carbonyl]amino]-9H-purin-9-yl]-β-D-ribofuranuronamide

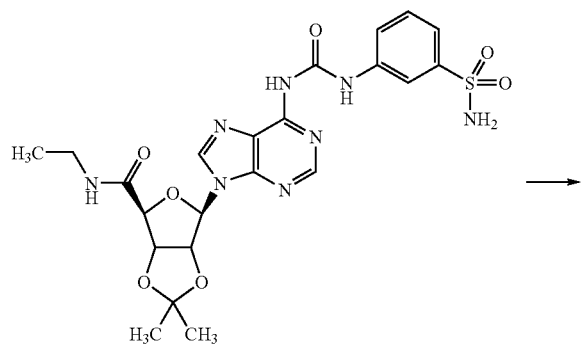

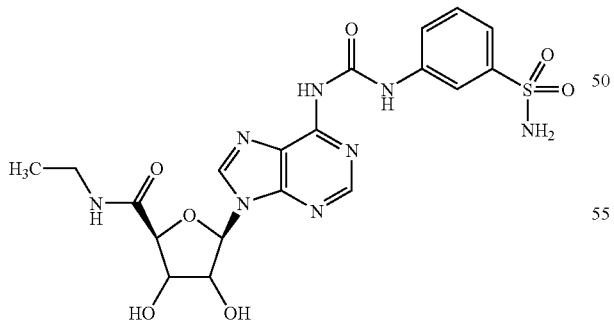

Yield: **m.p. **LC/MS: m/z 507.2 $[C_{19}H_{22}N_8O_7S+H]^+$. $^1$H-NMR (CD$_3$OD): δ 1.23 (t, 3H, J=7.2 Hz); 2.76 (s, 3H); 3.35 (m, 2H,); 4.21 (m, 1H); 4.38 (dd, 1H, J=1.9 Hz, J=4.6 Hz); 4.49 (d, 1H, J=1.5 Hz); 4.78 (m, 1H); 6.14 (d, 1H, J=7.3 Hz); 7.55 (t, 1H, J=8.0 Hz); 7.64 (d, 1H, J=7.7 Hz); 7.82 (d, 1H, J=7.1 Hz); 8.26 (s, 1H); 8.57 (s, 1H); 8.73 (s, 1H).

Example 126

Synthesis of 1-Deoxy-N-ethyl-1-[[6-[[[3-N-(isopropyl)-N-(methyl)-sulfonamidophenyl]amino]carbonyl]amino]-9H-purin-9-yl]-β-D-ribofuranuron-amide

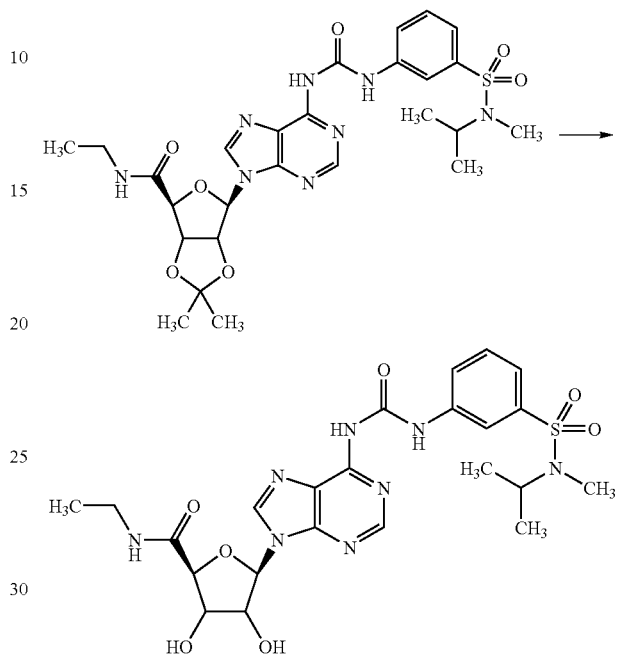

Yield: 82 mg, 96%. White solid. m.p. 147-148° C. LC/MS: m/z 563.2 $[C_{23}H_{30}N_8O_7S+H]^+$. $^1$H-NMR (CD$_3$OD): δ 1.01 (d, 6H, J=6.7 Hz); 1.21 (t, 3H, J=7.3 Hz); 2.76 (s, 3H); 3.38 (q, 2H, J=7.2 Hz); 4.21 (m, 1H); 4.39 (dd, 1H, J=1.9 Hz, J=4.8 Hz); 4.49 (d, 1H, J=1.8 Hz); 6.14 (d, 1H, J=7.3 Hz); 7.55 (bs, 2H); 7.78 (m, 1H); 8.28 (s, 1H); 8.56 (s, 1H); 8.74 (s, 1H).

Example 127

Synthesis of 1-Deoxy-N-ethyl-1-[[6-[[[3-N-(adamantan-1-yl)-sulfonamidophenyl]amino]carbony]amino]-9H-purin-9-yl]-β-D-ribofuran-uronamide

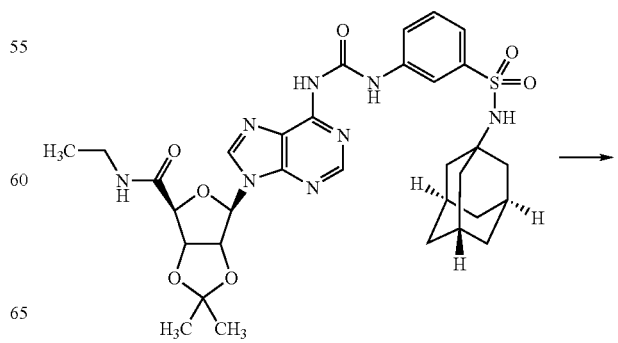

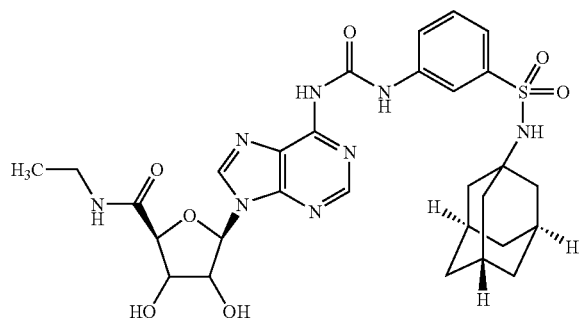

Yield: 60 mg, 86%. White solid. m.p. 188-189° C. LC/MS: m/z 641.0 $[C_{29}H_{36}N_8O_7S+H]^+$. $^1$H-NMR (CD$_3$OD): δ 1.21 (t, 3H, J=7.3 Hz); 1.61 (s, 6H); 1.84 (d, 6H, J=2.7 Hz); 1.97 (s, 3H); 3.37 (q, 2H, J=7.3 Hz); 4.39 (dd, 1H, J=1.9 Hz, J=4.8 Hz); 4.49 (d, 1H, J=1.9 Hz); 6.14 (d, 1H, J=7.2 Hz); 7.51 (t, 1H, J=7.9 Hz); 7.63 (d, 1H, J=6.9 Hz); 7.78 (d, 1H, J=8.0 Hz); 8.30 (t, 1H, J=1.9 Hz); 8.57 (s, 1H); 8.73 (s, 1H).

Example 128

Synthesis of 1-Deoxy-N-ethyl-1-[[6-[[[3-(2,5-dihydropyrrol-1-yl)sulfonylphenyl]amino]carbonyl]amino]-9H-purin-9-yl]-β-D-ribofuranuronamide

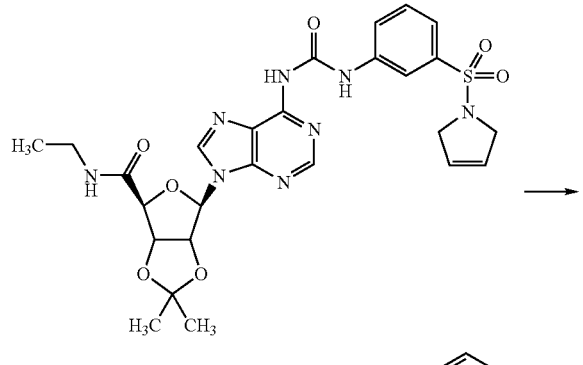

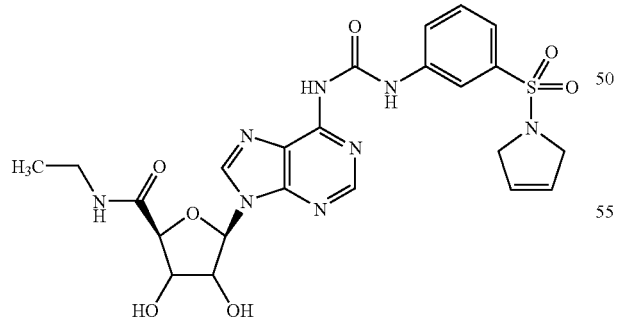

Yield: 78 mg, 97%. White solid. m.p. 145-146° C. LC/MS: m/z 559.0 $[C_{23}H_{26}N_8O_7S+H]^+$. $^1$H-NMR (CD$_3$OD): δ 1.21 (t, 3H, J=7.3 Hz); 3.36 (q, 2H, J=7.3 Hz); 4.14 (s, 4H); 4.38 (dd, 1H, J=1.8 Hz, J=4.8 Hz); 4.48 (d, 1H, J=1.8 Hz); 5.71 (s, 2H); 6.11 (d, 1H, J=7.3 Hz); 7.54 (d, 2H, J=5.1 Hz); 7.78 (m, 1H); 8.27 (s, 1H); 8.55 (s, 1H); 8.69 (s, 1H).

What is claimed is:

1. A compound selected from the group consisting of compounds of the following formulae:

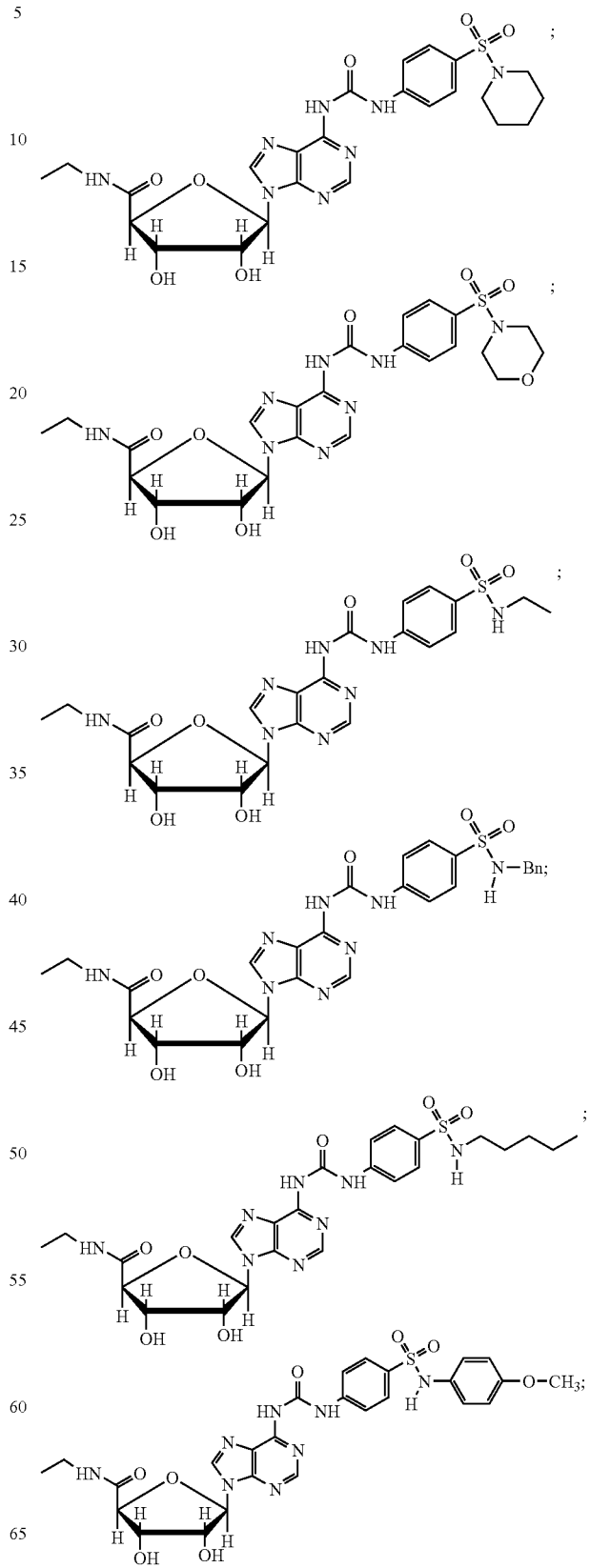

107
-continued
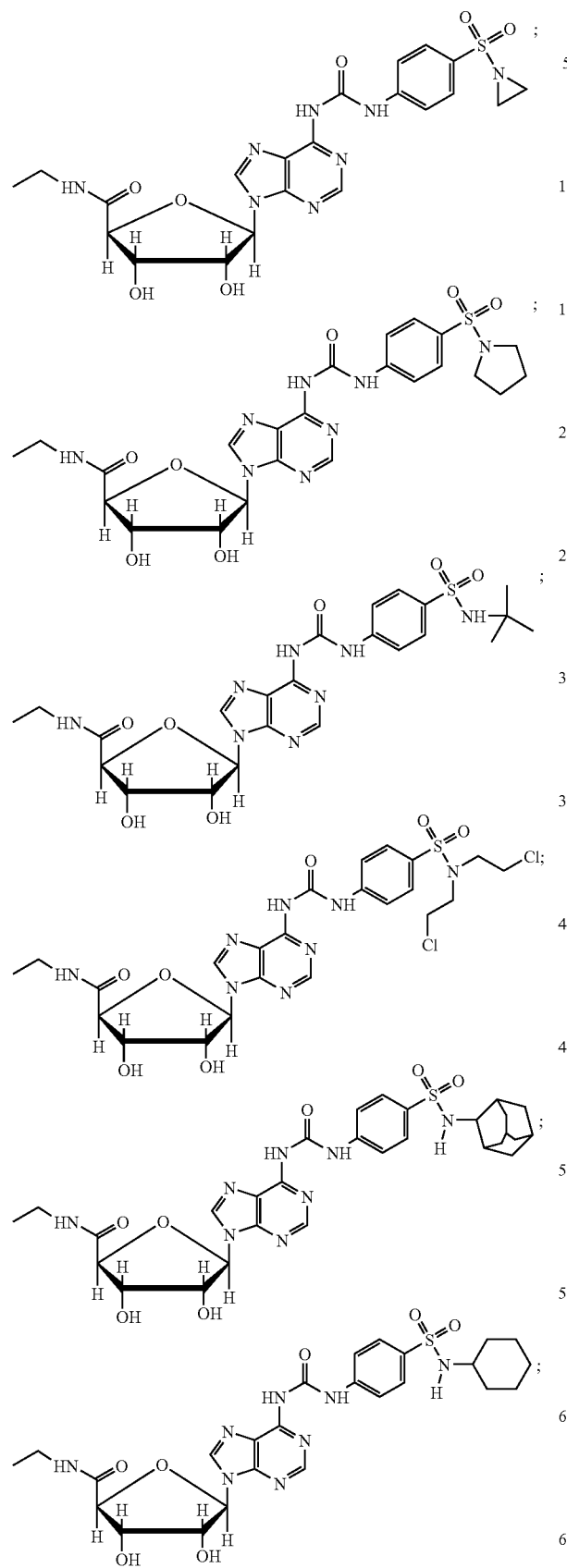
108
-continued
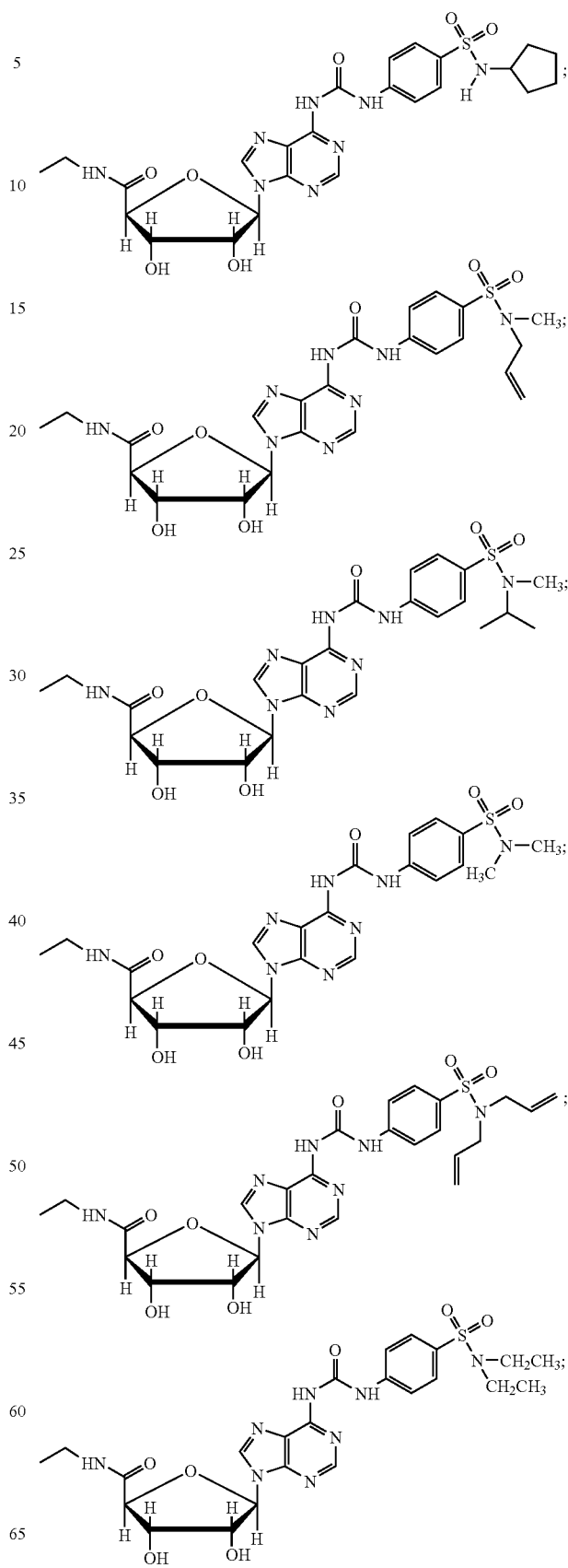

109 110
-continued
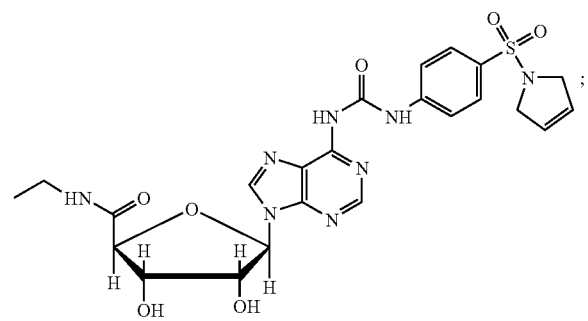
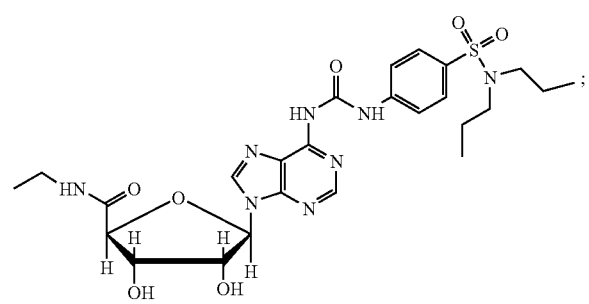
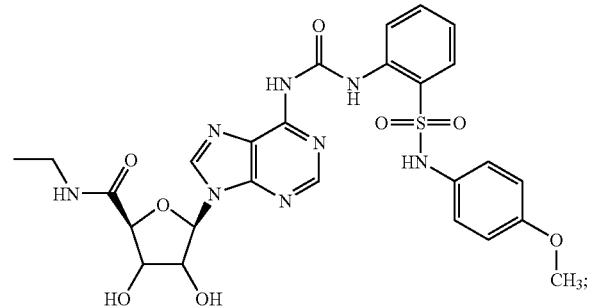
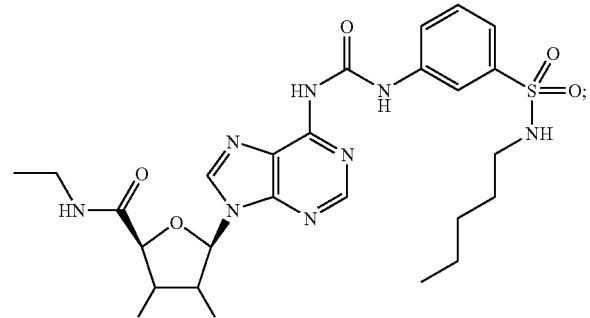
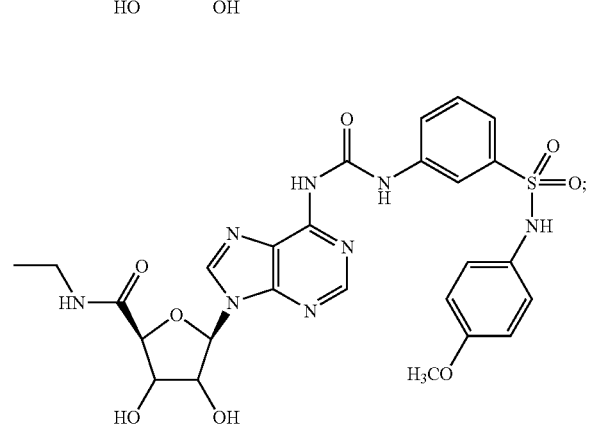
-continued
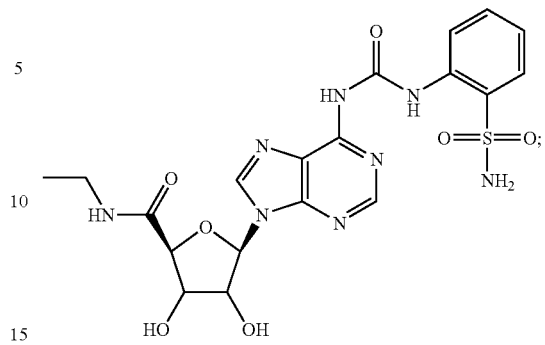
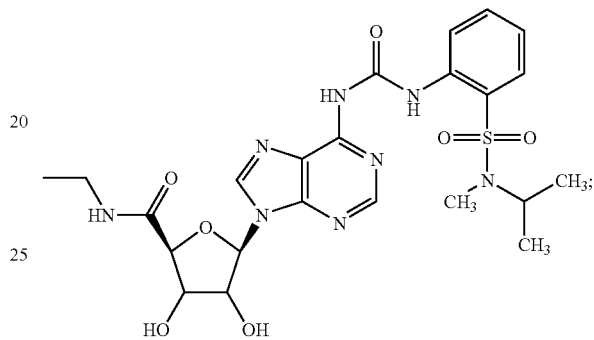
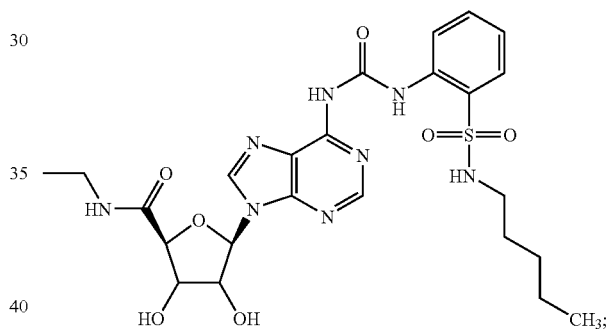
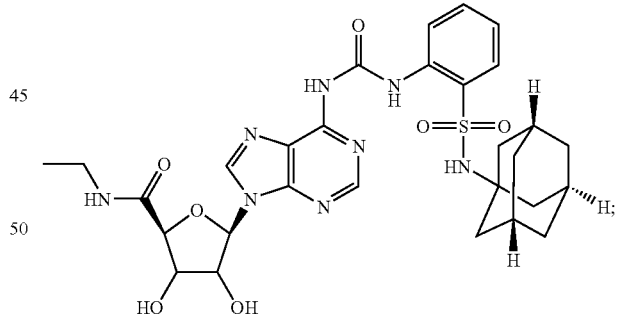
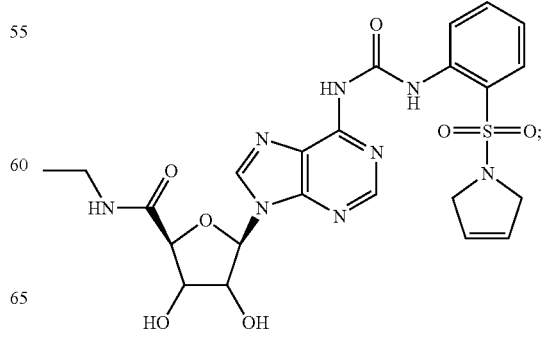

111
-continued
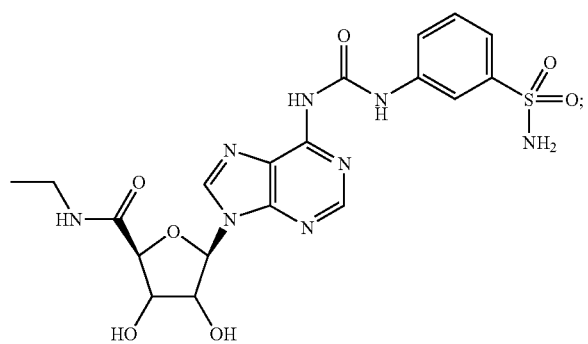
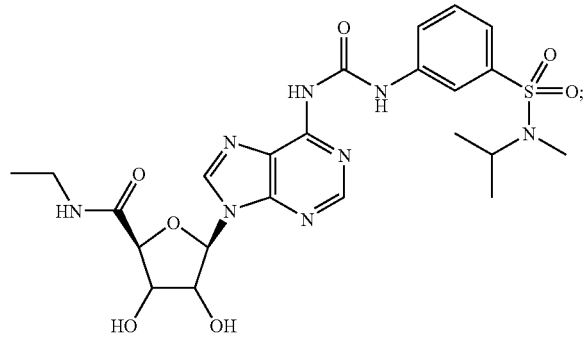
112
-continued
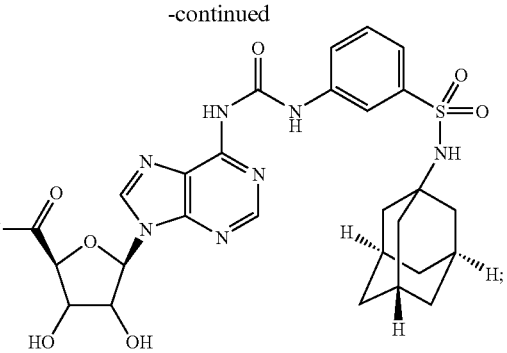
and
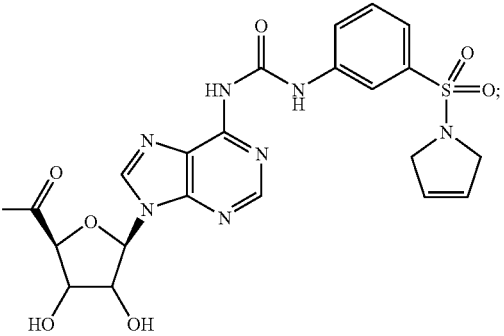
or a pharmaceutically acceptable salt thereof.
* * * * *